US012622724B2

(12) United States Patent
Mathis

(10) Patent No.: US 12,622,724 B2
(45) Date of Patent: *May 12, 2026

(54) DEVICES, METHODS, AND SYSTEMS TO TREAT CHRONIC BRONCHITIS

(71) Applicant: Free Flow Medical, Inc., Fremont, CA (US)

(72) Inventor: Mark L. Mathis, Fremont, CA (US)

(73) Assignee: Free Flow Medical, Inc., Fremont, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 17/642,128

(22) PCT Filed: Sep. 14, 2020

(86) PCT No.: PCT/US2020/050660
§ 371 (c)(1),
(2) Date: Mar. 10, 2022

(87) PCT Pub. No.: WO2021/051051
PCT Pub. Date: Mar. 18, 2021

(65) Prior Publication Data
US 2022/0346828 A1     Nov. 3, 2022

Related U.S. Application Data

(60) Provisional application No. 62/899,200, filed on Sep. 12, 2019.

(51) Int. Cl.
*A61B 17/3207* (2006.01)
*A61B 17/00* (2006.01)
*A61B 17/32* (2006.01)

(52) U.S. Cl.
CPC ................ *A61B 17/320758* (2013.01); *A61B 17/320725* (2013.01); *A61B 2017/00566* (2013.01);
(Continued)

(58) Field of Classification Search
CPC .... A61B 17/320725; A61B 17/320758; A61B 2017/00566; A61B 2017/00809; A61B 2017/320008; A61B 2217/005
See application file for complete search history.

(56) References Cited

U.S. PATENT DOCUMENTS 4,214,877  A     7/1980  Pemrick
4,540,404  A     9/1985  Wolvek
(Continued)

FOREIGN PATENT DOCUMENTS

JP          2000508954 A     7/2000
JP          2003504090 A     2/2003
(Continued)

OTHER PUBLICATIONS

European Search Report from counterpart EP App. No. 20862481.7 dated Jul. 19, 2023, 9 pages.
(Continued)

*Primary Examiner* — Katherine M Shi
*Assistant Examiner* — Mohammed S Adam
(74) *Attorney, Agent, or Firm* — Acuity IP, LLC; Nathan S. Cassell

(57)          ABSTRACT
Systems and methods involve abrading a patient lung airway wall to reduce mucus production therein. Exemplary techniques include rotationally and/or linearly oscillating an abrasive material against the airway wall so as to damage mucus producing tissues, for example by removing goblet cells, while destroying less than the entire airway wall. The abrasive material may be present on the surface of an expandable balloon body or another expandable device, which can be delivered to the patient treatment site via a bronchoscope. In some cases, the abrasion techniques can cause cell damage or death at a controlled or predetermined tissue depth.

57 Claims, 20 Drawing Sheets

(52) U.S. Cl.
CPC .............. *A61B 2017/00809* (2013.01); *A61B 2017/320008* (2013.01); *A61B 2217/005* (2013.01)

(56) References Cited

U.S. PATENT DOCUMENTS

| | | | |
|---|---|---|---|
| 4,828,582 A | 5/1989 | Frushour |
| 4,916,869 A | 4/1990 | Oliver |
| 5,066,335 A | 11/1991 | Lane et al. |
| 5,094,672 A | 3/1992 | Giles, Jr. et al. |
| 5,163,911 A | 11/1992 | Sirimanne et al. |
| 5,334,147 A | 8/1994 | Johnson |
| 5,336,184 A | 8/1994 | Teirstein |
| 5,367,024 A | 11/1994 | Neckermann |
| 5,382,234 A | 1/1995 | Cornelius et al. |
| 5,383,853 A | 1/1995 | Jung et al. |
| 5,413,560 A | 5/1995 | Solar |
| 5,458,613 A | 10/1995 | Gharibadeh et al. |
| 5,470,315 A | 11/1995 | Adams |
| 5,514,091 A | 5/1996 | Yoon |
| 5,620,417 A | 4/1997 | Jang et al. |
| 5,690,642 A | 11/1997 | Osborne et al. |
| 5,738,667 A | 4/1998 | Solar |
| 5,814,061 A | 9/1998 | Osborne et al. |
| 5,891,110 A | 4/1999 | Larson et al. |
| 5,951,568 A | 9/1999 | Schatz |
| 6,096,054 A | 8/2000 | Wyzgala et al. |
| 6,171,279 B1 | 1/2001 | Hilaire et al. |
| 6,371,940 B1 | 4/2002 | Valencia et al. |
| 6,371,961 B1 | 4/2002 | Osborne et al. |
| 6,488,673 B1 * | 12/2002 | Laufer .................. A61M 29/02 604/516 |
| 6,610,068 B1 | 8/2003 | Yang |
| 7,815,600 B2 | 10/2010 | Marashi et al. |
| 8,043,256 B2 | 10/2011 | Hansen et al. |
| 8,372,054 B2 | 2/2013 | Duffy et al. |
| 8,758,325 B2 | 6/2014 | Webster et al. |
| 9,972,082 B2 | 5/2018 | Holsing et al. |
| 10,245,410 B2 | 4/2019 | Aggerholm |
| 2004/0047855 A1 | 3/2004 | Ingenito |
| 2004/0158270 A1 * | 8/2004 | Wyzgala ........ A61B 17/320725 606/170 |
| 2006/0047291 A1 | 3/2006 | Barry |
| 2008/0249553 A1 | 10/2008 | Gruber et al. |
| 2011/0082483 A1 | 4/2011 | Diamant et al. |
| 2012/0101428 A1 * | 4/2012 | Springmeyer ... A61B 17/12104 604/506 |
| 2013/0225943 A1 * | 8/2013 | Holsing ............. A61B 10/0283 600/409 |
| 2013/0253387 A1 | 9/2013 | Bonutti |
| 2015/0119850 A1 * | 4/2015 | Seward ................... A61P 35/00 604/514 |
| 2016/0199093 A1 * | 7/2016 | Cambronne ... A61B 17/320758 606/159 |
| 2017/0224363 A1 | 8/2017 | Watanabe et al. |
| 2019/0183587 A1 | 6/2019 | Rafii-Tari |
| 2019/0380737 A1 * | 12/2019 | Kallok .......... A61B 17/320758 |

FOREIGN PATENT DOCUMENTS

| | | | |
|---|---|---|---|
| JP | 2011522598 A | 8/2011 |
| JP | 2014508580 A | 4/2014 |
| JP | 2017140110 A | 8/2017 |
| WO | 9834674 A1 | 8/1998 |
| WO | 9944513 A2 | 9/1999 |
| WO | 2009148807 A1 | 12/2009 |
| WO | 2012099974 A2 | 7/2012 |
| WO | 2019108901 A1 | 6/2019 |

OTHER PUBLICATIONS

International Search Report and Written Opinion from PCT/US2020/050660 dated Dec. 21, 2020, 8 pages.

Office action dated Mar. 26, 2024 with translation from JP Application No. 2022-516430, 7 pages.

* cited by examiner

DEVICES, METHODS, AND SYSTEMS TO TREAT CHRONIC BRONCHITIS

CROSS-REFERENCES TO RELATED APPLICATIONS

This application is a 35 U.S.C. § 371 U.S. National Stage of International Patent Application No. PCT/US2020/050660 filed Sep. 14, 2020, which claims the benefit of U.S. Provisional Patent Application No. 62/899,200 filed Sep. 12, 2019, the disclosures of which are incorporated herein by reference.

BACKGROUND OF THE INVENTION

The airways of the lung are comprised of various layers, each with one or several types of cells. The inner-most cellular layer of the airway wall is the epithelium or epithelial layer which includes pseudostratified columnar epithelial cells PCEC, goblets cells and basal cells. Goblet cells are responsible for the secretion of mucus, which lines the inner wall of the airways forming a mucus blanket. The pseudostratified columnar epithelial cells include cilia which extend into the mucus blanket. Cilia that are attached to the epithelium migrate towards the nose and mouth, propelling mucus up the airway in order for it to be expelled.

The basal cells attach to the basement membrane, and beneath the basement membrane resides the submucosal layer or lamina propria. The lamina propria includes a variety of different types of cells and tissue, such as smooth muscle. Smooth muscle is responsible for bronchoconstriction and bronchodilation. The lamina propria LP also include submucosal glands. Submucosal glands are responsible for much of the inflammatory response to pathogens and foreign material. Likewise, nerves are present. Nerve branches of the vagus nerve are found on the outside of the airway walls or travel within the airway walls and innervate the mucus glands and airway smooth muscle, connective tissue, and various cell types including fibroblasts, lymphocytes, mast cells, in addition to many others. And finally, beneath the lamina propria resides the cartilaginous layer. Pseudostratified columnar epithelial cells and goblet cells are connected to each other by tight junctions and adherens junctions. The pseudostratified columnar epithelial cells and goblet cells are connected to the basal cells by desmosomes. The basal cells are connected to the basement membrane by hemidesmosomes.

Pulmonary Disorders

Chronic bronchitis is characterized by a persistent airflow obstruction, chronic cough, and sputum production for at least three months per year for two consecutive years. The airway inflammation is consistent with a thickened epithelial layer.

A variety of pulmonary disorders and diseases lead to airway obstruction. A few of these disorders and diseases will be described briefly herein.

Chronic Obstructive Pulmonary Disease (COPD)

Chronic obstructive Pulmonary Disease (COPD) is a common disease characterized by chronic irreversible airflow obstruction and persistent inflammation as a result of noxious environmental stimuli, such a cigarette smoke or other pollutants. COPD includes a range of diseases with chronic bronchitis primarily affecting the airways; whereas, emphysema affects the alveoli, the air sacs responsible for gas exchange. Some individuals have characteristics of both.

In chronic bronchitis, the airway structure and function is altered. In chronic bronchitis, noxious stimuli such as cigarette smoke or pollutants are inhaled and recognized as foreign by the airways, initiating an inflammatory cascade. Neutrophils, lymphocytes, macrophages, cytokines and other markers of inflammation are found in the airways of people with prolonged exposure, causing chronic inflammation and airway remodeling. Goblet cells can undergo hyperplasia, in which the cells increase in number, or hypertrophy, in which the goblet cells increase in size. Overall, the goblet cells produce more mucus as a response to the inflammatory stimulus and to remove the inhaled toxins. The excess mucus causes further airway luminal narrowing, leading to more obstruction. Cilia are damaged by the noxious stimuli, and therefore the excess mucus remains in the airway lumen, obstructing airflow from proximal to distal during inspiration, and from distal to proximal during the expiratory phase. Smooth muscle can become hypertrophic and thicker, causing bronchoconstriction. Submucosal glands can also become hyperplastic and hypertrophic, increasing the overall thickness of the airway wall and, which further constricting the diameter of the lumen.

In addition to a reduction in the luminal diameter of the airway, mucus hypersecretion can also lead to an exacerbation, or general worsening of health. As a consequence of the excess mucus and damaged cilia, pathogens such as bacteria (e.g., *Haemophilus influenzae, Streptococcus pneumoniae, Moraxella catarrhalis, Staphylococcus aureus, Pseudomonas aeruginosa, Burkholderia cepacia*, opportunistic gram-negatives, *Mycoplasma pneumoniae*, and *Chlamydia pneumoniae*), viruses (rhinoviruses, influenze parainfluenza viruses, respiratory syncytial virus, coronaviruses, herpes simplex virus, adenoviruses), and other organisms (e.g., fungi) can flourish, causing an exacerbation, resulting in a set of symptoms. These include worsening cough, congestion, an increase in sputum quantity, a change in sputum quality, and/or shortness of breath. Treatment for an acute exacerbation can include oral or intravenous steroids, antibiotics, oxygen, endotracheal intubation and the need for mechanical ventilation via a ventilator.

Chronic obstructive pulmonary disease (COPD) is a common progressive, debilitating lung disease that is often fatal. COPD patients are diagnosed with either Emphysema, Chronic Bronchitis or more commonly, a combination of both. The symptoms of COPD include a persistent cough, particularly one that produces a lot of mucus; shortness of breath, especially during exercise; a wheezing sound while breathing; a barrel-chest deformity; tightness in the chest muscles due to expansion of the chest with the barrel-chest deformation and late stages manifests in symptoms that relate more closely to slow persistent suffocation as the disease eventually nearly totally obstructs any outflow of gas from the lungs. Such symptoms may start as a minor impediment to daily life, but they often lead to difficulty in talking or basic breathing. COPD reduces oxygen and carbon dioxide gas exchange which leads to circulatory problems, such as low oxygen levels in the blood, brain and heart muscles. This negatively affects mental alertness and contributes to a very rapid heartbeat, due to increased strain on the heart.

According to the National Institutes of Health, COPD is the third leading cause of death in the United States. The American Lung Association reports that more than 12 million people in the United States have been diagnosed with COPD. However, about 24 million more people may have the disease and not know it. Globally, COPD affects approximately 65 million people.

COPD can occur in people suffering from an inherited genetic condition called Alpha-1 Antitrypsin Deficiency (A1AT Deficiency) and from breathing air in environmental conditions such as air pollution, contaminated air, in work environments that are not ideal etc. However, COPD most commonly occurs in people who are over age 40 and who have a history of smoking. Cigarette smoke is composed of over 4000 different chemicals, many of which are toxic. Both smoke that the smoker inhales (through the filter) and the smoke from the burning end are toxic. There are three main components that are hazardous to health: tar, nicotine and carbon monoxide. Tar settles in the lungs and stimulates a series of changes that lead to obstructive lung disease and lung cancer. Nicotine is an addictive element in cigarettes and also stimulates the nervous system to reduce arteriole diameter and release adrenaline, increasing heart rate and blood pressure. Nicotine also causes increased stickiness of blood platelets, which increases the risk of blood clotting. Carbon monoxide combines irreversibly with hemoglobin so that oxygen cannot bind effectively. This causes a strain on the heart muscle because it must pump more to provide the same amount of oxygen.

Tobacco smoke and secondhand smoke travel down through the windpipe and into the bronchial tubes. The toxic smoke then moves into the bronchioles, which contain the small clusters of air sacs known as alveoli. Within the alveoli are the capillaries. In a healthy person, oxygen moves through the alveoli and into the capillaries and bloodstream during inhalation, allowing oxygen rich blood to be distributed to the rest of the body via the arterial system. Simultaneously, carbon dioxide is transported from blood along venous pathways to the capillaries and into the alveoli so it can be removed from the body during exhalation. This process is known as gas exchange. The elasticity of healthy air sacs enables this exchange to occur during lung volume change with breathing cycles. However, the inhalation of smoke ultimately destroys this elasticity and lung tissue itself.

Chronic Obstructive Pulmonary Disease; hereinafter, COPD is a disease of the lungs wherein the airways become narrowed which leads to a restriction in the flow of air into and out of the lungs causing shortness of breath. COPD includes both chronic emphysema and chronic bronchitis and is mainly caused by noxious particles or gases, most commonly from smoking or polluted air, which initiates an abnormal inflammatory response in the lung. Other causes of COPD are intense or prolonged exposure to workplace dusts and particles found in coal and gold mining, in the cotton textile industry with chemicals such as cadmium and isocyanates, fumes from welding, and non-smokers being exposed to the noxious particles and gases emitted from smokers. Lung damage, inflammation of the lung airways (alveoli), and passages clogged with mucus in the bronchial tubes are conditions associated with bronchitis and emphysema.

A COPD lung typically presents with enlarged bronchus and alveoli which are microscopic grape-like clusters of air sacs at the end of the smallest bronchiole airways. The alveoli are where gas exchange takes place, and are regarded as the primary functional units of the lungs. Alveoli are densely covered with capillaries that are extensions to the capillaries about the bronchus wherein blood is brought to the capillaries by the pulmonary artery and carried away by the pulmonary vein. When the alveoli inflate with inhaled air, oxygen diffuses into the blood in the capillaries to the tissues of the body, and carbon dioxide diffuses out of the blood into the lungs, where it is exhaled.

Asthma

Asthma is a disease of the airways characterized by airway hyper-responsiveness. In asthma, the epithelium can be thickened, mucus hypersecretion can be present as a result of excess production from goblet cells and submucosal glands, and smooth muscle can be thickened. As discussed herein, mucus hypersecretion or excess mucus can allow pathogens to flourish, leading to an infection.

Interstitial Pulmonary Fibrosis

Interstitial pulmonary fibrosis is thought to be initiated with acute injury to the lung tissue that leads to chronic and aberrant inflammation. Fibroblasts are activated in response to the inflammation, which causes pulmonary fibrosis, scarring, and worsening lung function. Only 20 to 30% of patients are alive at five years after the diagnosis.

Cystic Fibrosis

Cystic Fibrosis is a systemic disease with pulmonary manifestations defined by a genetic defect, wherein the Cystic Fibrosis Transmembrane Conductance Regulator (CFTR) gene is mutated, leading to thickened secretions that cannot be expelled. Chronic inflammation leads to airway remodeling and hypersecretion via the goblet cells and submucosal glands, which lead to airway constriction and infections that are difficult to full resolve.

Bronchiectasis

Bronchiectasis is a condition that leads to the airways to dilate, become thickened and scarred. It usually occurs due to an infection or other condition that injures the airway walls, prevents the airway from clearing mucus, or both. With this condition, the airways lose their ability to clear mucus, which can lead to repeated infections. Each infection causes additional damage, eventually leading to moderate airflow obstruction. Bronchiectasis can be caused by genetic disorders such as primary ciliary dyskinesia or can be of idiopathic origin.

Pulmonary Treatments

In some instances, the most effective treatment for a pulmonary disorder is a lifestyle change, particularly smoking cessation. This is particularly the case in COPD. However, many patients are unable or unwilling to cease smoking. A variety of treatments are currently available to reduce symptoms of pulmonary disorders.

Medication

COPD can be managed with one or several medications, such as Short Acting Beta Agonists (SABAs), Long Acting Beta Agonists (LABAs), Long Acting Muscarinic Antagonists (LAMAs), steroids, chronic antibiotic therapy, or PDE4 inhibitors such as Roflumilast. SABAs and LABAs act on the beta receptor of smooth muscle in the airway to cause bronchodilation. LAMAs act via anticholinergic pathways, inhibiting the release of acetylcholine causing bronchodilation. LABAs and LAMAs have been demonstrated to decrease breathlessness, reduce frequency of exacerbations and improve quality of life but have not been shown to decrease mortality. Tiotropium, a LAMA, can slow the rate of decline of lung function and increase the time until an exacerbation. Inhaled corticosteroids directly target inflammation. Inhaled corticosteroids have been demonstrated to decrease exacerbations but have little effect on lung function and mortality. Combinations of LABAs, LAMAs and inhaled corticosteroid drugs have been formulated. Inhaled oxygen is known to decrease breathlessness and improve mortality but these results are only associated with advanced disease represented by strict criteria and require chronic administration via nasal cannula or alternative apparatuses.

COPD can also be managed with one or several oral medications, such as PDE4 inhibitors, steroids, and antibiotics. Roflumilast is an oral medication that is a selective long acting inhibitor of the enzyme PDE4. It has very strong anti-inflammatory effects but is not well tolerated, with adverse effects including diarrhea, weight loss, nausea, decreased appetite and abdominal pain among others. Oral steroids such as prednisone can be prescribed to a patient in order to treat acute inflammation during an exacerbation. Patients have been known to continue on oral steroids for long periods of time if withdrawal leads to another exacerbation. Oral steroids have many side effects such as weight gain, insomnia, thyroid dysfunction, and osteoporosis, among others. Azithromycin or long-term administration of antibiotics has been shown to reduce the frequency of COPD exacerbations. Antibiotics can achieve this via an antimicrobial effect by killing the pathogens responsible for the exacerbation or by other mechanisms such as a reduction in mucus secretion as has been shown with macrolide antibiotics. Side effects of long-term administration of antibiotics include hearing loss and antibiotic resistance.

Oftentimes patients are non-compliant with prescribed respiratory medications. Inhaled therapies require deep inspiration as well as synchronization with inspiration, which many patients, especially the elderly, cannot perform. Patients can skip doses secondary to cost, experience side effects, or both. Together, all of these factors contribute to inadequate and inconsistent dosing.

Asthma can range in severity in adults, from mild disease to persistent. Milder disease can be adequately managed with trigger avoidance and Short Acting Beta Agonists (SABAs) whereas the mainstay of therapy for persistent asthma is inhaled glucocorticoids. Regular use of inhaled glucocorticoids has been shown in clinical trials to reduce the need for rescue inhalers, improve lung function, decrease symptoms, and prevent exacerbations. Some patients benefit from the addition of a leukotriene modifying agent or LABA. Tiotropium can be another option to improve lung function, more so than inhaled glucocorticoids alone. Very severe cases can require temporary or long-term treatment with oral corticosteroids.

There is no known cure for interstitial pulmonary fibrosis (IPF). The mainstay of treatment is supplemental oxygen when required and preventive measures, such as vaccination. Pirfenidone is an anti-fibrotic agent that is approved for IPE, attempting to slow the fibroblast foci, collagen disposition and inflammatory cell infiltration of the disease. In clinical trials, Pirfenidone has been shown to reduce the decline in vital capacity (a measure of pulmonary function) and demonstrated a reduction in all-cause mortality. Nintedanib is another agent approved for IPF and acts via a receptor blocker for multiple tyrosine kinases that mediate elaboration of fibrogenic growth factors (e.g., platelet-derived growth factor, vascular endothelial growth factor, fibroblast growth factor). It appears to slow the rate of disease progression in IPF. No device therapy is approved for IPF.

Treatment for cystic fibrosis has rapidly evolved from chest physiotherapy and supplemental oxygen to therapies that target the underlying defect in the CFTR gene. Ivacaftor is a CFTR potentiator, improving the transport of chloride through the ion channel, which is FDA approved for several CFTR gene mutations. In clinical trials it has been shown to improve FEV1 and reduce the frequency of exacerbations. It also improves mucociliary and cough clearance. It does not, however, improve outcomes when used alone in patients with the most common delta F508 deletion. Other targeted therapies are in clinical trials. Chronic antibiotics are commonly prescribed for CF, including azithromycin, which likely has anti-inflammatory benefits, and inhaled tobramycin to treat *Pseudomonas aeruginosa*. As with other obstructive diseases, CF patients benefit from bronchodilators including LAB As and LAMAs. Agents to promote airway secretion clearance include inhaled DNasc to decrease the viscosity of mucus, inhaled hypertonic saline to draw water from the airway in the mucus, and inhaled N-acetylcysteine that cleaves disulfide bonds within mucus glycoproteins. Guidelines recommend against chronic use of inhaled corticosteroids although oral steroids can be used in cases of exacerbations.

Bronchiectasis is the anatomic manifestation of a host injury response resulting in the excess dilatation of airway luminal caliber and thus therapy is often directed at the cause of the primary disease. These can be non-tuberculous mycobacteria infection, primary immunodeficiencies, allergic bronchopulmonary and aspergillosis among others. Treatment of acute exacerbation is focused on treating the offending bacterial pathogens with antibiotics. Macrolide and non-macrolide antibiotics have been shown to reduce the frequency of exacerbations. The use of inhaled antibiotics in the absence of CF is unclear as are the use of mucolytic agents. Bronchodilators can be used in patients with signs of airway obstruction on spirometry.

Primary Ciliary Dyskinesia (PCD) interventions aim to improve secretion clearance and reduce respiratory infections with daily chest physiotherapy and prompt treatment of respiratory infections. The role of nebulized DNase and other mucolytic drugs is less clear.

Respiratory tract infections caused by pathogens in the airway can occur with any of these maladies, and are typically treated with antibiotics. Unfortunately, drug development in this area is in decline and current therapies have significant limitations. One issue is that there is no one agent capable of treating the spectrum of pathogens found in these patients. While sputum testing can be performed to determine the resident pathogen or pathogens, this sometimes requires that specimens be obtained by bronchoscopy with special techniques to avoid sample contamination that typically effect other methods and modalities of collection. Another issue is that currently-available medicines are not always effective, due to pathogens developing a resistance to these therapies.

Bronchitis is an inflammation of the bronchial tubes, or bronchi, that bring air into the lungs. When the cells lining the bronchi are irritated, the tiny hairs (cilia) that normally trap and eliminate particulates from the air stop working. Formation of material (mucus and phlegm) associated with irritation (inflammation) also increases; causing the passages to become clogged. Mucus/phlegm and the inflamed bronchial lining constrict the airways causing them to become smaller and tighter which makes it difficult to get air into and out of the lungs. As an attempt to rid the constricted airways of the mucus/phlegm, the body responds with persistent, intense and severe coughing spells. Chronic bronchitis is often either misdiagnosed or neglected until it is in advanced stages.

In comparison to a normal bronchus, the inner bronchial wall of the bronchus affected by chronic bronchitis has an increased thickness which creates the decreased lumen diameter in the airway. The inner bronchial wall becomes enlarged or swollen due to irritants within the air when air is taken in. Once the inner bronchial wall is irritated, the small hairs (cilia) that normally protect the bronchus from foreign matter stop working. As, a result, (mucus and phlegm) associated with irritation (inflammation) forms; thereby decreasing the diameter of the airway and causing the passages to become clogged and restricted. The decreased lumen diameter of the airway prevents the proper flow of air into and out of the lung inhibiting the natural functions of the lung.

With repeated irritation events, the epithelium of the lung produces an increased numbers of goblet cells that produce increased volumes of mucus. The cilia in the lung transports mucus out to central airways where it may be coughed out. This is the lungs main mechanism to repel noxious particles and contaminants. After a number of inflammation events, the airway walls become scarred, the cilia fail to regenerate which eliminates the main means to transport mucus out of the lung. With a reduction of mucus transport, mucus accumulates in the airways and that collects and harbors bacteria that culminates in repeated infections. The infections cause coughing and the coughing further inflames the airways. This cycle continues until body generates an abundant of goblet and other cells in the airway walls to fight back the encroachment of foreign materials, inflammation and infections. This cycle continues until the patient is coughing for long periods or possibly continuously. The cycle causes the classic tissue wound healing in the airway walls that is constantly remodeled with additional goblet cells and other cells that produce mucus and the airways walls gradually thicken and restrict air flow.

Emphysema is defined as a breakdown or destruction in the walls of the alveoli causing them to become abnormally enlarged. A lung affected by emphysema has enlarged and engorged alveoli. The breakdown or destruction of the alveoli reduces the surface area available for the exchange of oxygen and carbon dioxide during breathing resulting in poor oxygenation (low oxygen and high carbon dioxide levels within the body). Also, elasticity of the lung itself is decreased leading to the loss of support of the airway embedded in the lung which often times leads to collapse of the airway thereby further limiting airflow.

With emphysema, as the alveoli deteriorates or is destroyed, the surrounding tissue loses its elasticity thereby causing the individual alveolus to expand and become engorged. Due to the inelasticity of the surrounding tissue, the abnormally enlarged alveoli fill easily with air during inhalation/inspiration, but lose the ability to empty the lung during exhalation/expiration.

In both cases of COPD, chronic bronchitis and emphysema, the greatest reduction in airflow occurs when breathing out (exhalation/expiration) because the air pressure in the lungs tends to compress rather than expand the airways. A person with COPD may not be able to completely finish breathing out before needing to take another breath. A small amount of the air from the previous breath remains within the lungs when the next breath is started. Easy filling and poor emptying of the lungs leads to progressive hyper-expansion or dynamic hyperinflation of the lungs resulting in inefficient breathing mechanics. Hyper-expansion/hyper-inflation of the lungs, in addition to the poor oxygenation capability, makes it progressively difficult to breathe.

In order to compensate for the breathing deficiencies, some people with advanced COPD manage to breathe faster; however, as a result, they usually develop dyspnea (chronic shortness of breath). Others, who may be less short of breath, tolerate the low oxygen and high carbon dioxide levels in their bodies, but eventually develop headaches, drowsiness, high blood pressure and even heart failure. Advanced COPD can lead to complications beyond the lung such as depression, muscle loss, weight loss, pulmonary hypertension, osteoporosis and heart disease.

Currently, there is no cure available for chronic bronchitis; most treatment is focused on making the symptoms less severe and trying to prevent further damage. The most common types of treatment involve changes in lifestyle, medication and supplemental oxygen supply. Examples of medications are bronchodilators to open airways; corticosteroids to reduce inflammation, swelling and phlegm production; and expectorants to stop the cough that often accompanies chronic bronchitis.

Lung Volume Reduction Surgery (LVRS), is a treatment option for patients with severe emphysema. In LVRS, a physician removes approximately 20-35% of the damaged lungs or of the poorly functioning space occupying the lung tissue from each lung. By reducing the lung size, the remaining lung and surrounding muscles are able to work more efficiently, making breathing easier.

LVRS is typically performed by techniques such as thoracoscopy, sternotomy and thoracotomy. Thoracoscopy is a minimally invasive technique where three small (approximately 1 inch) incisions are made in each side, between the ribs. A video-assisted thoracic surgery (VATS) or videoscope is placed through one of the incisions which allows the surgeon to see the lungs. A special surgical stapler/grasper is inserted in the other incisions and is used to cut away the damaged areas of the lung, reseal the remaining lung from leaking blood and air, and dissolvable sutures are used to close the incisions. Thoracoscopy can be used to operate on either one or both lungs and allows for assessment and resection of any part of the lungs. Thoracoscopic laser treatment of portions of the lung can also be performed using this technique. In contrast, thoracoscopic laser treatment, although capable of ablating emphysematous tissue only at the lung surface, prohibits simultaneous bilateral lung applications.

Sternotomy or open chest surgery involves an incision being made through the breastbone to expose both lungs. Both lungs are reduced in this procedure, one after the other. The chest bone is wired together and the skin is closed. This is the most invasive technique and is used when thoracoscopy is not appropriate. This approach is usually used only for upper lobe disease of the lung.

Thoracotomy is a technique often used when the surgeon is unable to see the lung clearly through the thoracoscope or when dense adhesions (scar tissue) are found. A 5 to 12-inch-long incision is made between the ribs; and the ribs are separated, but not broken, to expose the lungs. With this procedure only one lung is reduced and the muscle and skin are closed by sutures.

Although the goal of surgical therapy of COPD is to prolong life by relieving shortness in breath, preventing secondary complications, and enhancing quality of life by improving functional status, LVRS for COPD has higher surgical risks than heart surgery. Other risks associated with LVRS involve, but are not limited to: air leakage from the lung tissue at the suture line and into the chest cavity, pneumonia, bleeding, stroke, heart attack and death (resulting from worsening of any of the aforementioned complications). Because of the dangers associated with LVRS and despite advances in medical therapy, a significant number of patients with advanced COPD face a worsening quality of life and are at extremely high risk of death. Over the years, a number of minimally invasive methods have been developed to address the concerns related to LVRS and to focus on the selective destruction of specific areas of undesirable tissue as an alternative to LVRS. Some of these methods include cryosurgery, non-selective chemical ablation, and ablation through radiofrequency or (RF), ultrasound, microwave, laser and thermal electric methods. However, these developments are associated, as well, with a fair amount of surgically related setbacks including complications such as large and difficult to manipulate operating mechanisms and the inability to control therapy to the affected area. This is due to the fact that ablation techniques used historically have been non-selective in that they mediate cell death with methods such as extreme heat or cold temperatures. The aforementioned methods of focal destruction of affected areas have been proven to non-selectively and adversely affect blood vessels, nerves, and connective structures adjacent to the ablation zone. Disruption of the nerves locally impedes the body's natural ability to sense and regulate homeostatic and repair processes at and surrounding the ablation region. Disruption of the blood vessels prevents removal of debris and detritus. This also prevents or impedes repair systems, prevents homing of immune system components, and generally prevents normal blood flow that could carry substances such as hormones to the area. Without the advantage of a steady introduction of new materials or natural substances to a damaged area, reconstruction of the blood vessels and internal airway linings becomes retarded as redeployment of cellular materials is inefficient or even impossible. Therefore, historical ablation treatments do not leave tissue in an optimal state for self-repair in regenerating the region.

Improvements in medical devices and techniques have rekindled interest in the surgical treatment of COPD, wherein the effects highly resemble that of LVRS but without much of the associated risks and complications of conventional LVRS techniques. These recent developments offer an opportunity to advance the regenerative process following treatments. Irreversible Electroporation or (IRE) is one such technique that is pioneering the surgical field with improved treatment of tissue ablation. IRE has the distinct advantage of non-thermally inducing cell necrosis without raising/lowering the temperature of the ablation zone, which avoids some of the adverse consequences associated with temperature changes of ablative techniques such as radiofrequency (RF) ablation, microwave ablation, or even cryo-ablation. IRE also offers the ability to have a focal and more localized treatment of an affected area. The ability to have a focal and more localized treatment is beneficial when treating the delicate intricacies of organs such as the lung. However, these techniques require delivery of extremely high voltage to the lung in very close proximity to the heart. This presents the threat of potentially interrupting the signals that actuate heart muscle and interfering with pace makers or other sensitive electronic devices that may reside in the patient.

Clearly there is a need for non-thermal, non-cryo-ablation and non-electromagnetically energized devices and methods to induce cell necrosis in lung tissue and airway lumen. The devices and methods should be easy to deliver and deploy in lung tissues. These devices and methods should efficiently kill mucus producing cells and cause wound healing in lung tissues so tissue is regenerated with a reduced number of mucus producing cells as compared to the tissue that is being replaced.

SUMMARY OF THE INVENTION

Embodiments of the present invention relate to devices and methods to perform ERS (Epithelium Replacement Surgery), a minimally invasive technique in which devices with abrasive surfaces or features are pressed against target lung tissue or undesirable tissue and force is applied to cause device motion, relative to the tissue or point of contact with the tissue, to produce abrasive cell necrosis in the targeted tissue without destroying critical structures in target tissue such as complete airway walls, ducts, blood vessels and nerves. More precisely, these devices and methods enable ERS treatment to create defects in cell membranes, cell death and possibly bulk removal of epithelial and mucus or phlegm producing cells that lead to a disruption of homeostasis and autoregulation of lung epithelium while sparing connective and scaffolding structures and tissue. Thus, destruction of undesirable tissue is accomplished in a controlled and localized region while surrounding healthy tissue, organs, etc. are spared. By damaging or removing epithelial cells using these devices and methods, the epithelium may be replaced, healed or restored in a configuration comprising normal healthy replacement tissue or abnormal scar tissue. Regardless, the new tissue comprises a reduced number of mucus producing cells. This is different from other devices and methods that deliver light, thermal ablation, cryo-ablation or electro-magnetic energy which are known for totally destroying the cells and other important surrounding organs and bodily structures.

Described herein are embodiments of apparatuses, systems and methods for treating or manipulating pulmonary tissues and/or treating pulmonary diseases or disorders such as or associated with COPD (e.g., chronic bronchitis, emphysema), asthma, interstitial pulmonary fibrosis, cystic fibrosis, bronchiectasis, primary ciliary dyskinesia (PCD), acute bronchitis and/or other pulmonary diseases or disorders, wherein one or more features from any of these embodiments can be combined with one or more features from one or more other embodiments to form a new embodiment within the scope of this disclosure. Example pulmonary tissues include, without limitation, the epithelium (the goblet cells, ciliated pseudostratified columnar epithelial cells, and basal cells), lamina propria, submucosa, submucosal glands, basement membrane, smooth muscle, cartilage, nerves, pathogens resident near or within the tissue, or a combination of any or all of the foregoing.

The methods, apparatuses, and systems disclosed herein can treat pulmonary tissues via delivery of energy, generally characterized by manually applied motion, linear or rotary pulses, and combinations of these motions to target tissue using an abrasive device or surfaces with abrasive media to remove target tissue without causing a clinically significant inflammatory healing response, while in other embodiments, some inflammatory healing response is considered acceptable. This further allows for regeneration of healthy new target tissue within days of the procedure. In other embodiments, the nature of the energy delivery and abrasive action allows for removal of pathogens resident in the airway, such as by destruction, without substantially impacting or injuring any other airway structures.

In some embodiments, selectively treatments comprise selectively removing the particular cells from the airway wall. In some embodiments, removal comprises cell detachment. For example, cell detachment may be achieved by abrading the inner lumen of the diseased airway. In some embodiments, removal comprises cell death. For example, cell death may be achieved by fracturing the cellular wall of the epithelial cells. Or, cell death may occur by other mechanisms. Likewise, removal may comprise a combination of abrading, stripping off, damaging or other mechanisms.

In some embodiments, the particular cells comprise epithelial cells and not basal cells. For example, the epithelial cells may comprise abnormal or hyperplastic goblet cells.

Or, the epithelial cells may comprise abnormal ciliated pseudostratified columnar epithelial cells.

In some embodiments, the particular cells comprise cells of a basement membrane, and wherein selectively treats comprises modifying the cells of the basement membrane so as to modify the permeability of the basement membrane. In some embodiments, the particular cells comprise submucosal glands, and wherein selectively treats comprises causing cell death of the submucosal glands. In some embodiments, the particular cells comprise pathogens, and wherein selectively treats comprises causing cell death of the pathogens. In some embodiments, selectively treats comprises selectively modifies the particular cells to alter mucus production.

In some embodiments, the cells comprise epithelial cells and not basal cells. For instance, the epithelial cells may comprise abnormal or hyperplastic goblet cells. Or, the epithelial cells may comprise abnormal ciliated pseudostratified columnar epithelial cells.

In some embodiments, the cells comprise lymphocytes, macrophages, eosinophils, fibroblasts, plasma cells, mast cells, leukocytes or a combination of these. In some embodiments, the cells comprise submucosal glands, and wherein removal comprises causing cell death of the submucosal glands. In other embodiments, the cells comprise pathogens.

Embodiments of the present invention encompass novel medical devices, methods of use, systems, methods to select patients, methods to determine if retreatment is recommended and measures to evaluate patient health and for improving the quality and length of life of individuals suffering from Chronic Obstructive Pulmonary Disease (COPD). More particularly, embodiments of the present invention relate to devices and methods to damage, kill and/or remove epithelium and mucus producing cells in specific ways that allow these tissues to regenerate with less mucus producing cells. These devices described in this specification may scuff, scrape, cut, skive, slice, microtome or otherwise abrade using a blade, a sharp corner, an edge, agitate rough surfaces against tissue, employ bumpy material, bristles, spicules, brush tips or other geometry's that cause abrasive destruction of living cells. These same devices may also aspirate the tissues from the patient to enhance regeneration of tissue, improve lung function and reduce complications associated with other procedures that deliver low temperature fluid or procedures that deliver thermal or electro-magnetic energy.

In an aspect of the present invention, a therapy device is provided that makes abrasive contact with an animal or human lung airway wall to reduce mucus production.

In some aspects of the invention, abrasive contact can be provided by an abrasive media, an abrasive mesh, and/or an abrasive geometrical feature such as a blade, an edge, an triangle, a square, or a circle.

In another aspect of the present invention, a device is provided that may scuff, scrape, cut, skive, slice, microtome or otherwise abrade using a blade, a sharp corner, an edge, rough material, bumpy material, bristles, spicules, brush tips or other geometries that cause abrasive destruction of living cells.

In another aspect of the present invention, a therapy device is provided that makes abrasive contact with an animal or human lung airway lumen wall to harm mucus producing tissues or connective tissues that provide an attachment point for mucus producing tissues.

In another aspect of the present invention, a therapy device is provided that makes abrasive contact with an animal or human lung airway wall to harm mucus producing tissues while destroying less than the entire airway wall.

In another aspect of the present invention, a therapy device is provided that makes abrasive contact with the inner lumen wall of an animal or human lung airway to harm mucus producing tissues while destroying less than the entire airway wall.

In another aspect of the present invention, a therapy device is provided that makes abrasive contact with the inner wall of an animal or human lung airway lumen to harm mucus producing tissues while destroying less than the entire airway wall thickness.

In another aspect of the present invention, a therapy device is provided that makes abrasive contact with at least a portion of an animal or human lung airway lumen wall to produce one or more of the following changes in the treated patient:

i. Reduce symptoms caused by bronchitis in patients
    ii. Reduce the thickness of the airway wall in treated tissue
    iii. Reduce the level of inflammation in a patient's airway walls
    iv. Reduce the frequency of coughing in a bronchitis patient
    v. Reduce the frequency of coughing episodes in a bronchitis patient
    vi. Reduce the number of times the bronchitis patient has coughing episodes per year
    vii. Reduce the amount of phlegm production in a bronchitis patient
    viii. Reduce the frequency of lung infections in a bronchitis patient
    ix. Reduce the number of bacteria infected locations in a patient's airways or lungs
    x. Reduce the volume of bacteria production in the patient's sputum
    xi. Modify the composition of a patient's mucus, phlegm or sputum
    xii. Reduce the amount of mucus production that is produced in the treated lung
    xiii. Reduce the flow, rate of production, volume, volume as a function of time, nature of and mass of mucus that is produced in the treated lung or lung pair
    xiv. Reduce the level of hydration in the mucus that a patient produces
    xv. Increase the level of hydration in the mucus that a patient produces
    xvi. Reduce the number of goblet cells that remain in the lung
    xvii. Reduce the number of goblet cells that regenerate in the lung
    xviii. Reduce the number of goblet cells that can regenerate in the lung over the next 30, 60, 120, 180, 360 or 540 days
    xix. Reduce the density of goblet cells remaining in the lung
    xx. Reduce the thickness of the airway epithelium lining
    xxi. Reduce the volume of airway epithelium lining
    xxii. Degrade or kill connective tissue that maintains epithelium and/or goblet cell health
    xxiii. Degrade or kill tissues that provides nutrition to airway epithelium and/or goblet cells
    xxiv. Lift the diaphragm with respect to a reference rib location
    xxv. Measure diaphragm lift with respect to a reference rib location while the patient maintains expiration, as a result of treatment xxvi. Elevate the base of at least one lung towards the patient's upper chest xxvii. Reduce coughing xxviii. Reduce mucus production xxix. Reduce coughing caused by trapped air and mucus xxx. Reduce glottis closure sensitivity xxxi. Increase the patient's ability to clear mucus from the lungs xxxii. Increase arterial blood oxygen levels in the blood stream xxxiii. Increase arterial blood oxygen percent in the blood stream xxxiv. Decrease arterial $CO_2$ levels in the blood stream xxxv. Decrease arterial $CO_2$ percentage in the blood stream xxxvi. Increase mobility as measured by the currently standard 6-minute walk test xxxvii. Increase the number of meters a patient can walk in 6 minutes xxxviii. Increase lung airway caliber as measured using high resolution CT xxxix. Increase airway diameter xl. Increase lung emptying volume during expiration xli. Increase airway lumen diameter xlii. Provide radial outward support to airways xliii. Assist reduction of lung volume during exhalation xliv. Reduce the volume of at least one lung xlv. Reduce the volume of a lobe xlvi. Reduce the volume of both lungs xlvii. Reduce the volume of a lung pair xlviii. Reduce TLC of a lung pair xlix. Perform tissue compression l. Compress tissue in a lobe li. Remove slack in the lung tissue lii. Restore lung tissue elastic recoil back to a physiologic performance between 2 and 200 cm of H2O of pressure to expand the lung liii. Increase lung elastic recoil liv. Decrease lung compliance lv. Change the shape of the pressure volume curve generated by measuring patient breathing lvi. Increase the area within a pressure vs. volume curve describing a patient's breathing lvii. Displace fissures as seen using CT image post processed images comparing inspiration and expiration data lviii. Delay airway closure during expiration, by using post processed CT image data to compare pre-treatment versus post treatment airway volumes of a similar region in the lung lix. Cause a volume of the lung to be reduced lx. Reduce airway resistance lxi. Reduce the volume of one or more lungs in a patient lxii. Reduce inspiratory effort using pulse transit time or respiratory inductance plethysmography methods lxiii. Reduce dynamic hyperinflation as measured by CT or 6-minute walk testing or plethysmography lxiv. Reduce end-expiratory lung volume lxv. Reduce functional residual capacity lxvi. Reduce the incidence of respiratory failure lxvii. Increase time between COPD exacerbation events lxviii. Increase time that airways stay open during expiration lxix. Increase the forced expiratory volume in the first second (FEV1)

lxx. Increase the forced vital capacity volume (FVC)

lxxi. Increase the ratio FEV1/FVC lxxii. Reduce dysthymia lxxiii. Reduce pressure on the heart lxxiv. Reduce pressure on coronary arteries lxxv. Reduce blood hypertension lxxvi. Reduce hypertension in the lungs lxxvii. Reduce hypertension in blood vessels that supply the heart muscle lxxviii. Reduce systolic and/or diastolic blood pressure lxxix. Reduce heart rate lxxx. Reduce systolic blood pressure lxxxi. Increase the heart's ejection fraction lxxxii. Reduce pulmonary artery pressure lxxxiii. Reduce lung tissue density (from 800 to 810-1000 HU, that's Hounsfield units)

lxxxiv. Make lung tissue density more uniform (adjust the difference between lobes of average lobar density between 1-200 Hounsfield Units)

lxxxv. Increase forced expiratory volume during expiration lxxxvi. Reduce residual volume that is left in the lung during or after expiration (RV)

lxxxvii. Reduce the volume of gas that is trapped in the lung during or after expiration lxxxviii. Reduce the volume of gas that is trapped in a lobe during or after expiration lxxxix. Increase tidal expiratory volume change during tidal breathing at rest xc. Increase the inspiratory reserve volume during tidal breathing at rest xci. Decrease the patient's breathing rate xcii. Decrease the patient's heart rate xciii. Increase the patient's cardiac blood ejection fraction xciv. Decrease the patient's total lung capacity xcv. Decrease lung compliance xcvi. Decrease compliance in lobes or regions of lung tissue xcvii. Increase lung tissue compliance uniformity between upper versus lower lobes xcviii. Increase lung tissue compliance uniformity between lung lobes in a patient xcix. Increase lung tissue compliance uniformity between lobar segments c. Decrease inspiratory effort ci. Decrease the total lung capacity (TLC)

cii. Reduce the RV/TLC ratio ciii. Increase the volume of airways in a lobe during inspiration civ. Increase the volume of airways in a lobe during expiration cv. Reduce the difference in volume of lung airways in a lobe during breathing cvi. Increase the total blood volume in a patient's lung or lobe by performing a treatment cvii. Reduce regional blood volume in severely compromised lung tissue to reduce the volume of reduced oxygenated blood being mixed with normal blood in emphysema patients cviii. Increase the change in lobar volume between an inspiration and expiration breathing cycle cix. Reduce the volume of trapped air in a lobe after expiration cx. Reduce expiratory volume of lungs after treatment cxi. Increase volume of one or more lobes during inspiration cxii. Increase the volume within distal airways in one or more lobes cxiii. Increase the volume within central airways in one or more lobes cxiv. Reduce impedance of central airways in one or more lobes cxv. Reduce impedance in one or both lungs cxvi. Reduce resistance to flow in one or more lobes cxvii. Reduce resistance to flow in one or more lungs cxviii. Increase blood vessel density in one or more lobes cxix. Increase the number of blood vessels per liter of lobar volume cxx. Increase the volume of airway wall in one or more lobes cxxi. Increase the volume of airway wall in central airways of one or more lobes cxxii. Decrease the percentage of damaged tissue per liter of lung volume in one or more lobes cxxiii. Hold airways open longer to increase the rate of aerosol transport in one or more lobes cxxiv. Hold airways open longer to increase regional concentration of aerosol delivered drugs in one or more lobes cxxv. Measure one or more fissures that have moved more than 2 mm to indicate lobar volume has changed cxxvi. Measure one or more fissures that have moved with respect to a chest wall rib more than 2 mm to indicate lung volume has changed cxxvii. Reduce the percentage of low attenuation lung tissue in one lobe or more cxxviii. Reduce the volume of low attenuation lung tissue in one lobe or more cxxix. Reduce the percentage of low-density tissue that is 950 HU or higher in one lobe or more cxxx. Reduce the volume of low-density tissue that is 950 HU or higher in one lobe or more.

In another aspect of the present invention, a therapy device is provided that may be delivered directly to a treatment location without the assistance of a delivery system.

In another aspect of the present invention, a therapy device is provided that may be delivered to a treatment location being guided by a guidewire.

In another aspect of the present invention, a therapy device is provided that may be delivered directly to a treatment location through the lumen of a catheter.

In another aspect of the present invention, a therapy device is provided that may be delivered directly to a treatment location through the lumen of an endoscope.

In another aspect of the present invention, a therapy device is provided that may be delivered directly to a treatment location through the lumen of a bronchoscope.

In another aspect of the present invention, a therapy device is provided that may be delivered directly to a treatment location using any combination of delivery system components described in this specification.

In another aspect of the present invention, a therapy device is provided that may provide therapy while expanding the device in a fixed position relative to a point along the longitudinal axis of the airway.

In another aspect of the present invention, a therapy device is provided that may provide therapy while advancing the device relative to a point along the longitudinal axis of the airway.

In another aspect of the present invention, a therapy device is provided that may provide therapy delivered while moving the device from a position within an airway in the lung along the airway longitudinal axis more towards the trachea.

In another aspect of the present invention, a therapy device is provided that may provide therapy while rotating the device within the lumen of the airway.

In another aspect of the present invention, a therapy device is provided that may provide therapy while rotating the device about the airway longitudinal axis within the lumen of the airway.

In another aspect of the present invention, a therapy device is provided that may provide therapy while linearly translating an abrasive surface against the airway wall in an oscillatory manor that may be driven by the physician or by an electromagnetic motor or transducer within the lumen of the airway.

In another aspect of the present invention, a therapy device is provided that may provide therapy while moving an abrasive surface against the airway wall in a rotational orientation to produce abrasion in a circumferential direction inside the airway lumen that may be provided in an oscillatory manner. The oscillation may be driven by the physician or by an electromagnetic motor or transducer to produce steady constant motions while the physician or a robot closed loop system controls the positioning in the airway tree and area of treatment within the airway system.

In another aspect of the invention, devices are provided that cause tissue contact, abrasion and cell death at a controlled depth of between 0.1 and 3 mm, and in some embodiments more preferentially between 0.5 and 0.68 mm depth into the airway inner lumen wall. In some cases, the controlled depth is about 0.02 mm, or about 20 microns. In some cases, the controlled depth is between 1 micron and 500 microns. In some cases, the controlled depth is between 10 and 100 microns. In some cases, the controlled depth is between 10 and 50 microns.

In another aspect of the invention, devices are provided that cause tissue contact, abrasion and cell death at a controlled depth in a way that does not allow continued motions to allow continued erosion into the airway lumen wall as a function of time. One example of such a device is a large balloon that is fixed to the distal end of a catheter. The balloon may be expanded against the airway lumen to make continuous contact around the entire airway lumen inner circumference. The balloon may be rotated, moved linearly along the airway axis or both motions may be conducted simultaneously. The motions may be oscillatory in nature at frequencies of between 1 and 500 million hertz, and in some embodiments more preferably between 40 and 300 cycles per second. In some cases, the operational frequency is selected such that grabbing of the tissue by an abrasion feature is avoided or minimized, and gliding of the abrasion feature along the tissue is facilitated. The motions may be powered by an electromechanical driver such as a speaker motor or a rotational motor. The motor may be powered using a power source such as alternating current from a power station or it may be powered using a direct current battery that may be rechargeable. An abrasive media may be permanently attached to the outside surface of the balloon in a configuration that allows it to protrude radially outward from the balloon outer surface a discrete distance to present a specific rough surface. The amount may be 0.5 to 0.68 mm or it may protrude more to clear accumulated biologic material and still provide abrasion to a depth of 0.5 to 0.68 mm in the airway wall. As the balloon is inflated and expanded against the tissue and motion is provided, the abrasive surface may abrade the surface of the tissue to cause cell death. This would provide a device and means to cause cell death. Additionally, the abrasive media may be attached to the balloon outer surface in a specific pattern or area ratio so that only a portion of the exterior of the balloon provides abrasive contact with the airway wall tissue. The ratio may be between 0.1 and 99 percent of the exterior surface area of the balloon may be coated with abrasive media. More preferably, 2 to 50 percent of the balloon exterior surface may be coated with abrasive media. The rest of the balloon outer surface should be smooth and possibly lubricated. By providing a device in this configuration, the smooth portions of the balloon may bear against the tissue in the form of a bearing or depth limiting element and these portions of the balloon will not erode lung tissue. The adjacent regions on the surface of the balloon that have abrasive media attached, may erode the tissue to only a limited depth. This is an example of a device that may provide depth-controlled erosion in lung tissue. The abrasive material may be attached to the balloon in the form of a continuous circumferential stripe so the entire circumference of the airway lumen or inner wall sees abrasive action. As the device is advanced or retracted along the axis of the airway, the complete circumference and length along the path the device is moved will be completely treated. This is important as the goal of the treatment is to induce complete airway epithelium death to eliminate mucus producing cells and to promote remodeling. If local regions are left untreated, local remaining mucus producing cells may regenerate and proliferate and this could exacerbate the original problem. This example provides a device that may cause complete cell death along lengths of lung airway epithelial surfaces without causing destruction of lung airway basement structures or membranes.

In another aspect of the present invention, a therapy device is provided that may provide therapy while performing any combination of the motions described in this specification.

In another aspect of the present invention, a therapy device is provided that may be expanded to make contact with at least a portion of the circumference of an airway lumen wall and/or to move the device in the ways described in this specification to cause abrasion and cell death to reduce mucus production in the lung.

In another aspect of the present invention, a therapy device is provided that makes abrasive contact with lung tissue by providing expansion and/or motion that may be driven by pneumatic or hydraulic pressure.

In another aspect of the present invention, a therapy device is provided that makes abrasive contact with lung tissue by providing expansion and/or motion that may be driven using elastic strain energy stored in materials, such as those used to make spring elements including one or more of the following: nitinol, steel, ferrous or non-ferrous metals, polymers, elastomers, ceramics such as carbon and carbon fiber or CMC materials (ceramic matrix composites).

In another aspect of the present invention, a therapy device is provided that makes abrasive contact with lung tissue by providing expansion and/or motion that may be driven by mechanical means using a linkage, a torque drive cable or wire or a push or pull rod or tether.

In another aspect of the present invention, a therapy device is provided that makes abrasive contact with lung tissue by providing expansion and/or motion that may be driven using pneumatic, hydraulic, stored strain energy or mechanical actuation means and the expansion or motion may be driven by or controlled using heat, pressure, force, light, voltage, electrical current, stored strain energy, friction, optically coupled sensors or actuators, electrically actuated sensors or drivers that may use components such as a piezo crystal driver, linear or rotational magnetic actuator, linear or rotational motor, a capacitor, inductor, crystal, fluid, element or combination of elements found on the periodic chart table of chemical elements that may be modified by exposure to voltage, electrical current, a magnetic field, light, pressure, sound, heat or other stimulus to affect actuation of a device to make contact with a lung airway wall or to move the device to enable abrasive destruction of cells.

In another aspect of the present invention, a therapy device is provided that makes abrasive contact with lung tissue by providing expansion and/or motion of a brush device that makes full circumferential contact with an airway wall to abrade surface cells, damage goblet cells, cause deliberate remodeling of lung airway interior wall and/or cause other destruction to reduce mucus production as a treatment for chronic bronchitis and COPD.

In another aspect of the present invention, a therapy device is provided that makes abrasive contact with lung tissue by providing expansion and/or motion of a brush that may be mechanically actuated to expand to make contact with more than one portion of the circumference of a lung airway.

In another aspect of the present invention, a therapy device is provided that provides abrasive contact with lung tissue comprising a brush that may be mechanically actuated to expand or move in a way that maintains a constant pressure against the lung tissue.

In another aspect of the present invention, a therapy device is provided that provides abrasive contact with lung tissue comprising an inflated structure that may be pneumatically actuated to expand or move in a way that maintains a constant pressure against the lung tissue.

In another aspect of the present invention, a therapy device is provided that provides abrasive contact with lung tissue comprising an inflated structure that may be pneumatically actuated to expand or move in a way that maintains a constant pressure against the lung tissue even if the diameter of expansion changes during the treatment.

In another aspect of the present invention, a therapy device is provided that provides abrasive contact with lung tissue comprising an inflated structure that may be pneumatically actuated to expand or move in a way that maintains a constant pressure against the lung tissue even if the diameter of expansion changes during the treatment and pneumatic pressure or pressure relief must be provided to maintain the constant pressure against the lung tissue.

In another aspect of the present invention, a therapy device is provided that makes abrasive contact with lung tissue by providing expansion and/or motion that may be driven by pneumatic or hydraulic pressure or by using elastic strain energy, utilizing materials that can store elastic strain energy (nitinol, steels, metals, polymers, elastomers, ceramics such as carbon and carbon fiber, CMC materials (ceramic matrix composites).

In another aspect of the present invention, a therapy device is provided that makes abrasive contact with lung tissue by providing expansion and/or motion that may be driven mechanically using linkages, a torque drive, push or pull tethers, optically coupled sensors and actuators, electrically actuated sensors and drivers such as components comprising piezo, magnetic, motor, capacitor and inductor components that may rotate or translate to expand the abrasive element so it may come in contact with at least a portion of the airway wall to cause cell death.

In another aspect of the present invention, a therapy device is provided that makes abrasive contact with lung tissue by providing expansion and/or motion comprising a brush system may be configured so bristles are arranged as a spiral or staggered so no portion of the circumference of the airway is not affected as the brush is dragged longitudinally along the airway axis.

In another aspect of the present invention, a therapy device is provided that makes abrasive contact with lung tissue by providing expansion and/or motion that may be driven by a balloon that can be inflated to bear against the airway wall and be dragged proximally so abrasive materials that are attached to the outside of the balloon surfaces, comprising any abrasive media that is used in sand paper and industrial applications such as alumina, carbide, sand, quartz, glass, metals, ceramics, plastics, forms of carbon including diamond, oxides, silicon carbide particles, metallic particles, polymeric particles, particles with a diameter between 2-3000 um and generally abrasive biocompatible materials may make contact with the airway wall to kill mucus producing cells. Abrasive grit and other abrasive materials which can be used with embodiments of the present invention are disclosed in U.S. Pat. Nos. 4,214,877; 4,828,582; 4,916,869; 5,066,335; 5,094,672; and 5,367,024. The content of each of these patents is incorporated herein by reference. Exemplary abrasive grit or other abrasive materials may include silicon carbide, aluminum oxide, co-fused alumina zirconia, garnet, flint, diamond, cubic boron nitride, glass, tungsten carbide, cobalt, alumina, glass-like polysaccharides, sintered sol-gels, styrene acrylonitrile co-polymers, silicon carbide, alumina-zirconia, garnet, emery, chromium(III) oxide, and the like. In some embodiments, grit sizes may range from 5 microns in average particle diameter to 2000 microns in average particle diameter.

In another aspect of the present invention, a therapy device is provided that makes abrasive contact with lung tissue by providing expansion and/or motion that may be driven by the release of stored strain energy to bear against the airway wall so abrasive materials that are attached to the tissue contacting surfaces, comprising any abrasive media that is used in sand paper and industrial applications such as alumina, carbide, sand, quartz, glass, metals, ceramics, plastics, forms of carbon, oxides, silicon carbide particles, particles with a diameter between 2-3000 μm and generally abrasive biocompatible materials may make contact with the airway wall to kill mucus producing cells.

In another aspect of the present invention, a therapy device is provided that makes abrasive contact with lung tissue comprising a balloon that may expand blade elements that are attached to the balloon exterior to that act as scrapers during expansion or while the balloon is dragged along a longitudinal axis of the airway.

In another aspect of the present invention, a therapy device is provided that makes abrasive contact with lung tissue comprising a balloon that may expand to press specifically sized abrasive grit into lung tissue so it penetrates only a pre-determined and controlled distance into tissue.

In another aspect of the present invention, a therapy device is provided that makes abrasive contact with lung tissue comprising a balloon that may expand abrasive mesh material such as abrasive grit impregnated polymer, metallic, or composite mesh materials into the airway wall.

In another aspect of the present invention, a therapy device is provided that makes abrasive contact with lung tissue by providing expansion and/or motion to a balloon that expands to drive abrasive brush fiber materials into the airway wall.

In another aspect of the present invention, a therapy device is provided that makes abrasive contact with lung tissue by providing expansion and/or motion using a balloon that may be made from highly elastic polymers to allow the balloon to conform to various airway diameters within the airway as it's moved along the airway longitudinal axis.

In another aspect of the present invention, a therapy device is provided that makes abrasive contact with lung tissue by providing expansion and/or motion of a balloon that is expanded using a fixed volume of fluid or gas and the balloon inflated using an open loop system that maintains a constant pressure or utilizes a closed loop system that feeds back volume or pressure data to maintain one or the other while the device is providing therapy in the patient.

In another aspect of the present invention, a therapy device is provided that makes abrasive contact with lung tissue by providing expansion and/or motion comprising an aspiration catheter with an open distal end and a distal protruding stylet with abrasive materials attached. The device may be configured so that suction pulls the airway down to the sides of the distal stylet and it can be dragged proximally to abrade epithelium and aspirate material out of the patient at the same time.

In another aspect of the present invention, a therapy device is provided that makes abrasive contact with lung tissue by providing expansion and/or motion using a closed loop or open loop system that may be used to control suction pressure, volume or both, as the treatment is performed.

In another aspect of the present invention, a therapy device is provided that makes abrasive contact with lung tissue comprise a catheter with a plugged distal tip and at least one open side port that communicates suction to pull the airway to come into contact with at least a portion of a side of the catheter and abrasive material or an abrasive edge that may scrape to cause cell death to reduce mucus production.

In another aspect of the present invention, a therapy device is provided that makes abrasive contact with lung tissue by providing catheter with outer surfaces that may be impregnated or coated with abrasive material to cause cell death as the abrasive material is brought into contact with a point located on the wall of an airway lumen as the device is moved to different locations in the lung in a way that maintains contact between the abrasive material and the airway wall.

In another aspect of the present invention, a therapy device is provided that makes abrasive contact with lung tissue by providing at least one abrasive surface comprising a mixture of abrasive materials that may be attached to a portion of the surface of the device that makes contact to lung tissue to enhance the abrasive effect.

In another aspect of the present invention, a therapy device is provided that makes abrasive contact with lung tissue by providing a catheter comprising a variation of diameters so tissue may be sucked into a preferential diameter to control the depth of penetration of the abrasive material in contact with tissue.

In another aspect of the present invention, a therapy device is provided that makes abrasive contact with lung tissue by providing Large differences in catheter outside diameter step sizes such as diametral steps that represent a difference of between 0.2 and 20 mm of diameter but preferentially the difference is between 0.5 and 3 mm.

In another aspect of the present invention, a therapy device is provided that makes abrasive contact with lung tissue by providing a catheter, mechanical structure or a balloon that provides an abrasive surface, the abrasive surface being the largest diameter portion of the device to increase the pressure of penetration that the abrasive surface bears against tissue and to increase the speed and efficiency with which the therapy is provided.

In another aspect of the present invention, a therapy device is provided that makes abrasive contact with lung tissue by providing a catheter, mechanical structure or a balloon that provides an abrasive surface, the abrasive surface not being the largest diameter portion of the device to reduce the pressure of penetration that the abrasive surface bears against tissue and to limit the speed and efficiency with which the therapy is provided.

In another aspect of the present invention, a therapy device is provided that makes abrasive contact with lung tissue by providing a catheter, mechanical structure or a balloon that provides an abrasive surface, the abrasive surface not being the largest diameter portion of the device to limit the depth of penetration that the abrasive surface bears against tissue and to limit the speed and efficiency with which the therapy is provided.

In another aspect of the present invention, a therapy device is provided that makes abrasive contact with lung tissue by providing a catheter, mechanical structure or a balloon that provides an abrasive surface, the abrasive surface is brought into contact with the tissue using a low-pressure source such as pneumatic suction or vacuum.

In another aspect of the present invention, a therapy device is provided that makes abrasive contact with lung tissue by providing a catheter, one or more balloons that are fixed to the catheter, an abrasive surface whereas the abrasive surface is brought into contact with lung tissue using a low-pressure source such as pneumatic suction or vacuum.

In another aspect of the present invention, a therapy device is provided that makes abrasive contact with lung tissue by providing a catheter, a conduit and port that may communicate low pressure gas or fluid and an abrasive surface at a select location on the catheter whereas a low-pressure source such as pneumatic suction or vacuum is communicated through the conduit and port in the catheter to draw lung tissue into contact with select location that contains the abrasive surface to cause cell death in lung tissue.

In another aspect of the present invention, a therapy device is provided that makes abrasive contact with lung tissue by providing a catheter, mechanical structure or a balloon that is driven to oscillate or rotate using a brushless rotary motor or linear motor driver.

In another aspect of the present invention, a therapy device is provided that makes abrasive contact with lung tissue by providing a catheter, mechanical structure or a balloon that is driven to oscillate or rotate using electrical energy provided by an electrical circuit containing a detachable plug between the device and the source of the electrical energy that drives the device.

In another aspect of the present invention, a therapy device is provided that makes abrasive contact with lung tissue by providing a catheter, mechanical structure or a balloon that is driven to oscillate or rotate using electrical energy provided by an electrical circuit containing a battery.

In another aspect of the present invention, a therapy device is provided that makes abrasive contact with lung tissue by providing a catheter, mechanical structure or a balloon that is driven to oscillate or rotate using electrical energy provided by an electrical circuit containing a rechargeable battery.

In another aspect of the present invention, a therapy device system is provided that makes abrasive contact with lung tissue by providing a catheter, mechanical structure or a balloon providing at least one abrasive surface that may be driven to rotate or oscillate within a lung airway, a rotation or oscillation driver that is powered by electrical energy, an electrical circuit containing a battery and a charger.

In another aspect of the present invention, a therapy device system is provided that makes abrasive contact with lung tissue by providing a catheter, mechanical structure or a balloon providing at least one abrasive surface that may be driven to rotate or oscillate within a lung airway, a rotation or oscillation driver that is powered by pneumatic pressure or vacuum and a pneumatic circuit containing a pneumatic pressure or vacuum source.

In another aspect of the present invention, a therapy device system is provided that makes abrasive contact with lung tissue by providing a catheter, mechanical structure or a balloon providing at least one abrasive surface that may be driven to rotate or oscillate within a lung airway, a rotation or oscillation driver that is powered by dimensional changes of a crystal such as quartz and a crystal.

In another aspect of the present invention, a therapy device system is provided that makes abrasive contact with lung tissue by providing an abrasive surface that can perform an abrading action on the lung tissue. In some cases, the abrading action can be achieved by inflating and/or deflating a balloon upon which an abrasive feature is disposed, or by expanding or contracting a mechanism upon which an abrasive feature is disposed. The abrading action can be the result of inflation/expansion and/or deflation/contraction of the balloon or mechanism as the diameter of the balloon or mechanism increases and/or decreases, and/or as the linear length of the balloon or mechanism increases and/or decreases. Such inflation/expansion and/or deflation/contraction can create relative motion between the abrasive surface and the tissue surface, thus contributing to the abrading action.

In another aspect of the present invention, a therapy device system is provided that makes abrasive contact with lung tissue by providing an abrasive surface that can perform an abrading action on the lung tissue, and the device provides a self-limiting depth of abrading.

In still another aspect, embodiments of the present invention encompass tissue treatment devices having an elongate member, an abrasion feature disposed on or coupled with the elongate member, and a control mechanism in operative association with the elongate member. In some cases, the control mechanism is configured to produce oscillatory motion in the abrasion feature. Such oscillatory motion can operate to abrade tissue along a lumen wall of a patient. In some cases, an elongate element can be provided as or include a balloon catheter shaft, a balloon body, a balloon, a catheter shaft, a catheter, a distal abrader body, an abrader element shaft, and abrasive brush, an elongate element, or the like. In some cases, an abrasion feature can be provided as or include an abrasive grit, an abrasive grit pattern, an abrasive mesh, raised edges, an expanded abrasive surface, a band having abrasive grit, an abrasive material, one or more abrasive edges, strands, abrasive media, raised abrasive edges, abrasive bristles, an expanded or expandable foam, sponge, or ribbon structure or bundle, or the like. In some cases, a control mechanism can be provided as or include a motor assembly, a motion driving handpiece, handpiece, or the like. In some cases, the oscillatory motion includes rotary oscillatory motion. In some cases, the oscillatory motion includes linear oscillatory motion. In some cases, the oscillatory motion includes rotary oscillatory motion and linear oscillatory motion. In some cases, the device is configured to abrade tissue at a controlled depth. In some cases, the controlled depth is about 20 microns. In some cases, the device further includes a vacuum mechanism that operates to draw the tissue toward the abrasion feature. In some cases, the vacuum mechanism is provided as or includes a vacuum source. In some cases, the vacuum mechanism operates to remove abraded tissue from the lumen of the patient. In some cases, the abrasion feature includes an abrasive mesh, an abrasive geometrical feature, or an abrasive media selected from the group consisting of as alumina, carbide, sand, quartz, glass, metal, ceramic, plastic, carbon, diamond, oxide, silicon carbide, polymer, silicon carbide, aluminum oxide, co-fused alumina zirconia, garnet, flint, diamond, cubic boron nitride, tungsten carbide, cobalt, glass-like polysaccharide, sintered sol-gel, styrene acrylonitrile co-polymer, alumina-zirconia, garnet, emery, and chromium(III). In some cases, the abrasive media has a grit size within a range from about 2 microns in average particle diameter to 3000 microns in average particle diameter. In some cases, the elongate member includes an expandable mechanism, and the abrasion feature is disposed on the expandable mechanism.

In yet another aspect, embodiments of the present invention encompass methods for treating a wall of a lumen within a patient. Exemplary methods can include introducing an elongate member of a treatment device into the lumen of the patient, the elongate member having an abrasion feature, and producing oscillatory motion in the abrasion feature, so as to abrade tissue along the wall of the lumen of the patient. In some cases, the oscillatory motion includes rotary oscillatory motion. In some cases, the oscillatory motion includes linear oscillatory motion. In some cases, the oscillatory motion includes rotary oscillatory motion and linear oscillatory motion. In some cases, the abrading step includes abrading the tissue at a controlled depth. In some cases, the controlled depth is about 20 microns. In some cases, methods can include drawing the tissue toward the abrasion feature using a vacuum mechanism. In some cases, methods can include removing the abraded tissue from the lumen using the vacuum mechanism. In some cases, the abrasion feature includes an abrasive mesh, an abrasive geometrical feature, or an abrasive media selected from the group consisting of as alumina, carbide, sand, quartz, glass, metal, ceramic, plastic, carbon, diamond, oxide, silicon carbide, polymer, silicon carbide, aluminum oxide, co-fused alumina zirconia, garnet, flint, diamond, cubic boron nitride, tungsten carbide, cobalt, glass-like polysaccharide, sintered sol-gel, styrene acrylonitrile co-polymer, alumina-zirconia, garnet, emery, and chromium(III). In some cases, the abrasive media has a grit size within a range from about 2 microns in average particle diameter to 3000 microns in average particle diameter. In some cases, the elongate member includes an expandable mechanism, the abrasion feature is disposed on the expandable mechanism, and a method includes expanding the expandable mechanism.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Exemplary systems, devices, and methods as disclosed herein are well suited for use in treating pulmonary airways of a patient. In some cases, the abrasion techniques and systems disclosed herein can be used to treat the peripheral vasculature (e.g. arteries or veins) of a patient, the coronary vasculature (e.g. arteries or veins) of a patient, an organ or lumen wall of a patient, and any undesirable lesion, surface, or growth that may occur on a tissue surface of a patient.

Bronchitis Therapy Delivery Overview

Figure 1:
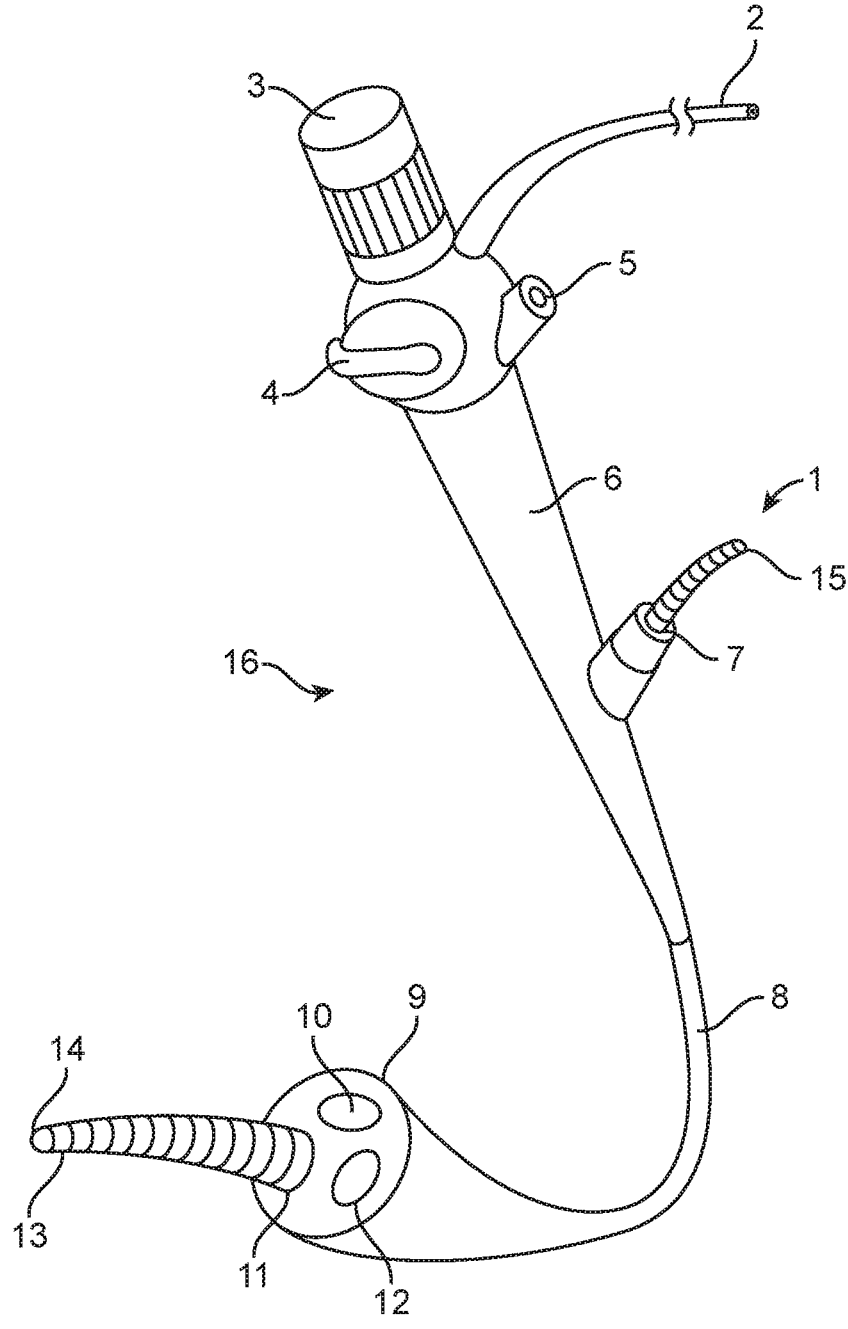
FIG. 1 illustrates a typical bronchoscope.

The pulmonary treatment devices described in this specification are sized and configured to be delivered by a delivery device configured to be inserted into the lung, such as a steerable scope (e.g. bronchoscope 1), such as illustrated in FIG. 1. In some embodiments, the pulmonary treatment device 13 is configured to be delivered through a lumen in the delivery device, such as by pushing the treatment device through a lumen of a scope, catheter, introducer, sheath, sleeve or similar device. In other embodiments, the pulmonary treatment device 13 is configured to be delivered by mounting it on the outside of a delivery device, such as on the outside of a scope, catheter (e.g. a balloon catheter), introducer, sheath, sleeve, guidewire or similar device. In some embodiments, when mounting on the outside of a delivery device, the treatment device 13 freely slide along the length of the delivery device. It may be appreciated that the pulmonary treatment device 13 may be configured to be delivered using a combination of these delivery device components such as mounting the treatment device 13 on a guidewire or balloon catheter shaft and delivering the assembly through the channel of the bronchoscope. It may be appreciated that when using a guidewire, the delivery system may be configured to be Over-The-Wire (OTW) or Rapid Exchange (RX) wherein the guidewire exits the delivery system at a particular location for the configuration. For example, in an OTW design, the guidewire exits the delivery system at its proximal end so that the guidewire that tracks along the full length of the delivery device. In contrast, in the RX design, the guidewire only tracks along a short section (about 25 cm) of the delivery device and then exits at a side port. This design saves time compared with advancing a guidewire through the full length of the delivery device. In some embodiments, a delivery system or device 16 for delivering a treatment device 13 may include a bronchoscope 1, a guidewire, a guide catheter, a handpiece, and or additional elements as described elsewhere herein. Exemplary Over-The-Wire (OTW) features which may be used with systems and method embodiments of the present invention are described in U.S. Pat. Nos. 4,540,404; 5,163, 911; 5,382,234; 5,470,315; 5,891,110; 5,951,568; 6,171, 279; 6,610,068; and 8,372,054, and exemplary Rapid Exchange (RX) features which may be used with systems and method embodiments of the present invention are described in U.S. Pat. Nos. 5,334,147; 5,336,184; 5,383, 853; 5,413,560; 5,458,613; 5,620,417; 5,690,642; 5,738, 667; 5,814,061; 6,371,961; 6,371,940; 7,815,600; 8,043, 256; 8,758,325; and 10,245,410. The content of each of these patents is incorporated herein by reference.

In some embodiments, the treatment device 13 is loaded into a bronchoscope port 7 and the bronchoscope 1 is advanced through the tracheobronchial tree to a target location within the lung. In patients with advanced COPD, lung tissue and airways are inflamed, bleed easily and react to even slight trauma, such as by advancement of a guidewire or catheter. Therefore, unlike conventional endobronchial valves and coils, in these embodiments, the device 13 may be deliverable without the use of a guidewire and/or catheter. In this embodiment, the device 13 is loaded within the bronchoscope port 7 so that the distal end 14 of the device 13 is directed distally through the channel exit port 11 and the proximal end 15 of the device 13 extends proximally through the bronchoscope port 7. The bronchoscope 1 is then steered through the airways atraumatically, without digging its distal tip into the airway walls. The distal end 14 may have a variety of shapes including an end loop, coil, ball, bullet, tear drop, cone or taper shape to minimize tissue trauma. Typically, the distal end of the bronchoscope 1 is advanced into or well beyond the $4^{th}$ generation airways, often into the areas of the lung containing highly damaged tissue. This is easily accomplished when the bronchoscope outer diameter is less than 4.5 mm diameter. This is typically a bronchoscope with a 2.0 mm diameter channel and port. However, the therapy devices described herein may be advanced down small bronchoscopes with an outside diameter of less than 3.0 mm and down channel lumen that may be smaller than 1.5 mm Treatment of larger airways that are more centrally located may be accomplish using larger bronchoscopes comprising a working channel with a 2.5 mm or larger working channel. More typically, however, scopes with working channels in the range of 1.8 to 3.2 mm are most preferable.

Figure 9:
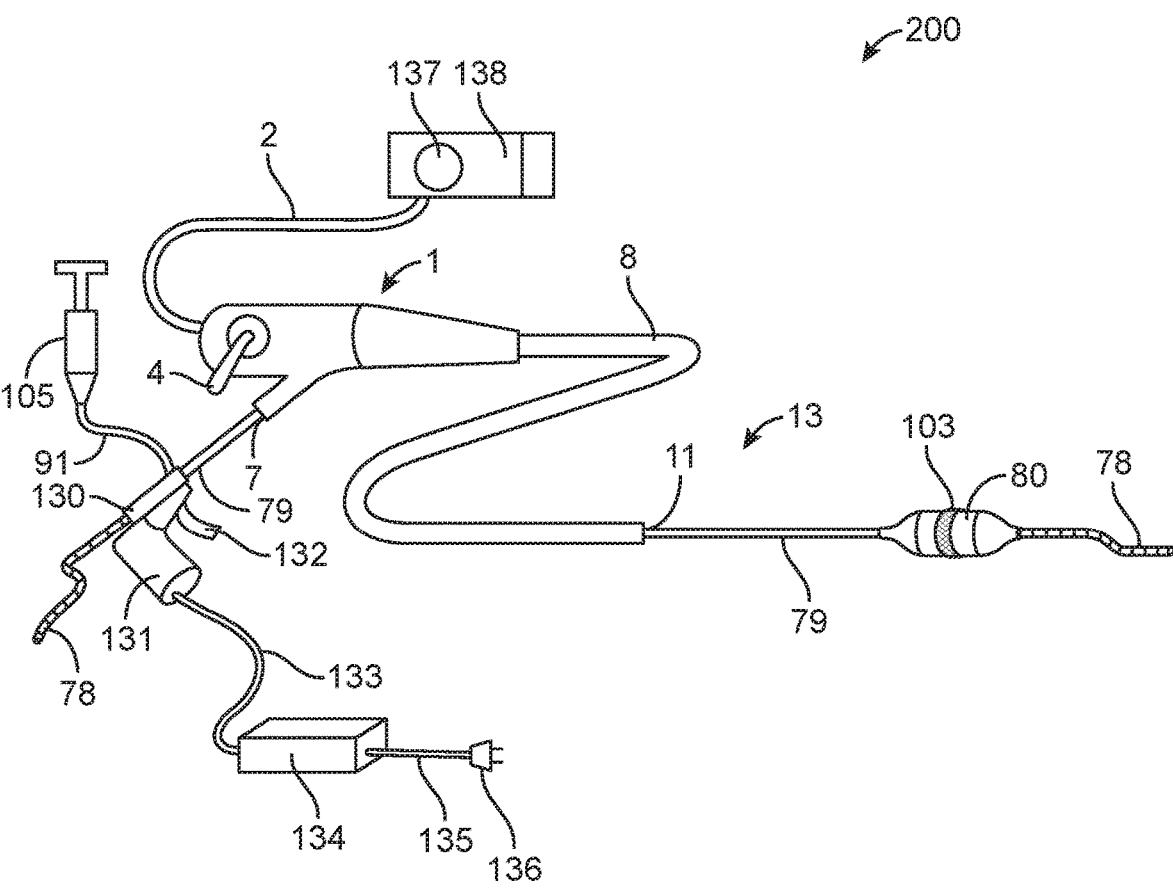
FIG. 9 illustrates the pulmonary treatment system delivered through a bronchoscope with accessories.
Figures 14, 15:
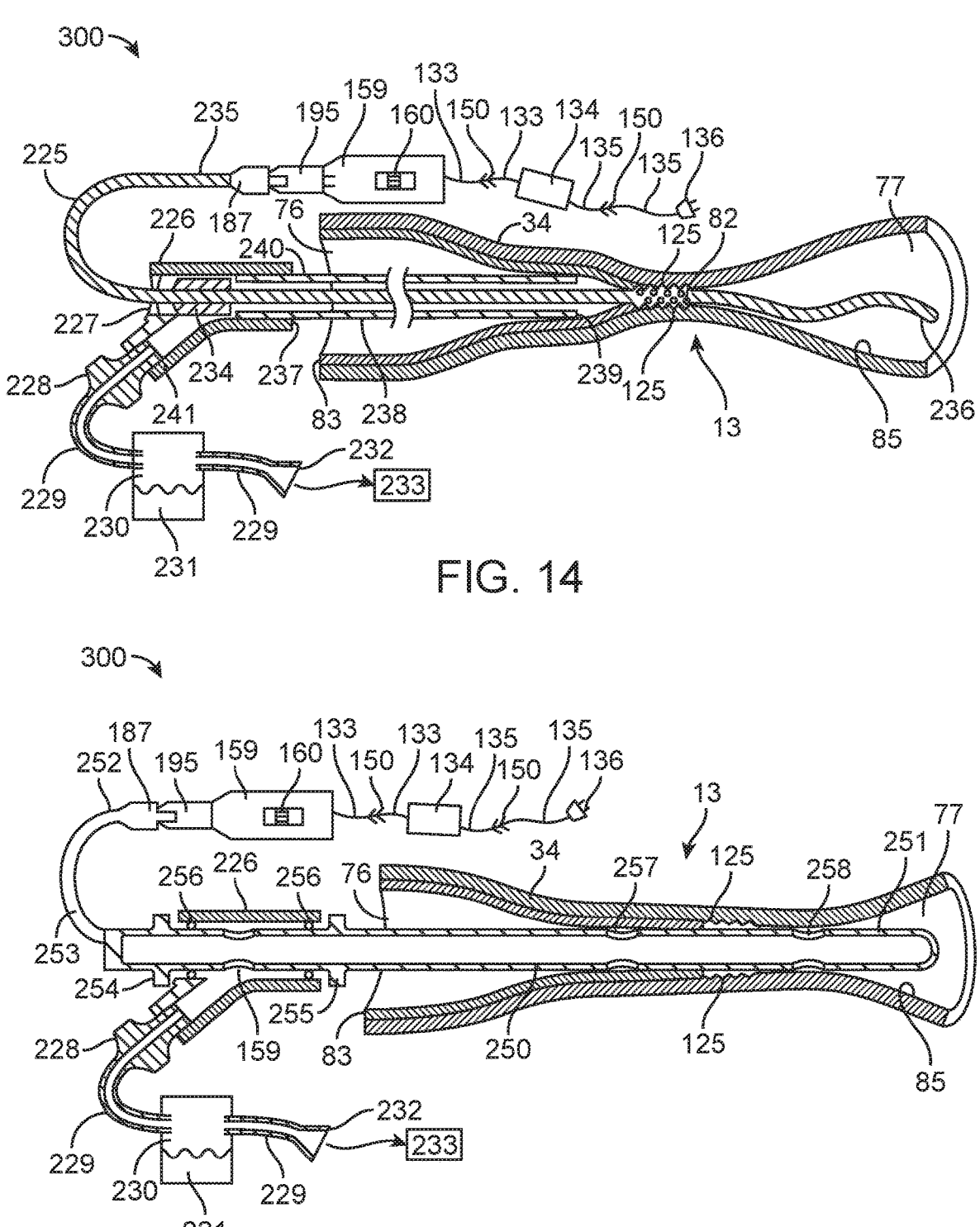
FIG. 14 illustrates a pulmonary treatment system with an abrasive guidewire and suction catheter.
FIG. 15 illustrates a pulmonary treatment system with an abrasive catheter.

The bronchoscope illustrated in FIG. 1 is typically used for delivering therapeutic treatments into the lung. The control handle 4 is actuated up or down by the physician to bend the distal scope tip 9 up or down. If the scope is rotated 90 degrees by grasping and rotating the scope body 6, the actuation of the handle steers the scope left or right. While steering the scope, the user may advance the flexible trunk 8 into the patient's mouth, trachea and lungs. An electronic image data file is captured by a camera 10, processed in the camera head 3 and sent to a monitor 138, as seen in FIG. 9, via the data cable 2. A hose that provides vacuum from the hospital vacuum system may be attached to the suction port 5 to aspirate mucus, bacteria and other foreign materials from the lung airways, into the channel exit port 11, out the suction port 5 and into a filter trap 231, as seen in FIG. 14. At the distal end of the bronchoscope, a scope tip 9 provides a working channel exit port 11, a light source 12 that normally comprises terminated and a polished light transmitting fiber bundle that can transmit light energy. Additionally, the camera 10 is positioned at the scope tip 9 so there is an unobstructed view of the path the scope is taking. When the physician has advanced the flexible trunk 8 in a patient so the scope tip 9 is adjacent or near a treatment sight, the distal tip 14 of a pulmonary treatment device 13 is inserted into the bronchoscope channel insertion port 7. The device 13 is advanced until it exits out the channel exit port 11. The therapy is performed and then the device is removed from the bronchoscope channel and the bronchoscope 1 is removed from the patient. It is understood that the terms "therapy device", "treatment device", "pulmonary treatment device", "tissue treatment device" and the like, can be used interchangeably throughout this disclosure.

Figure 2:
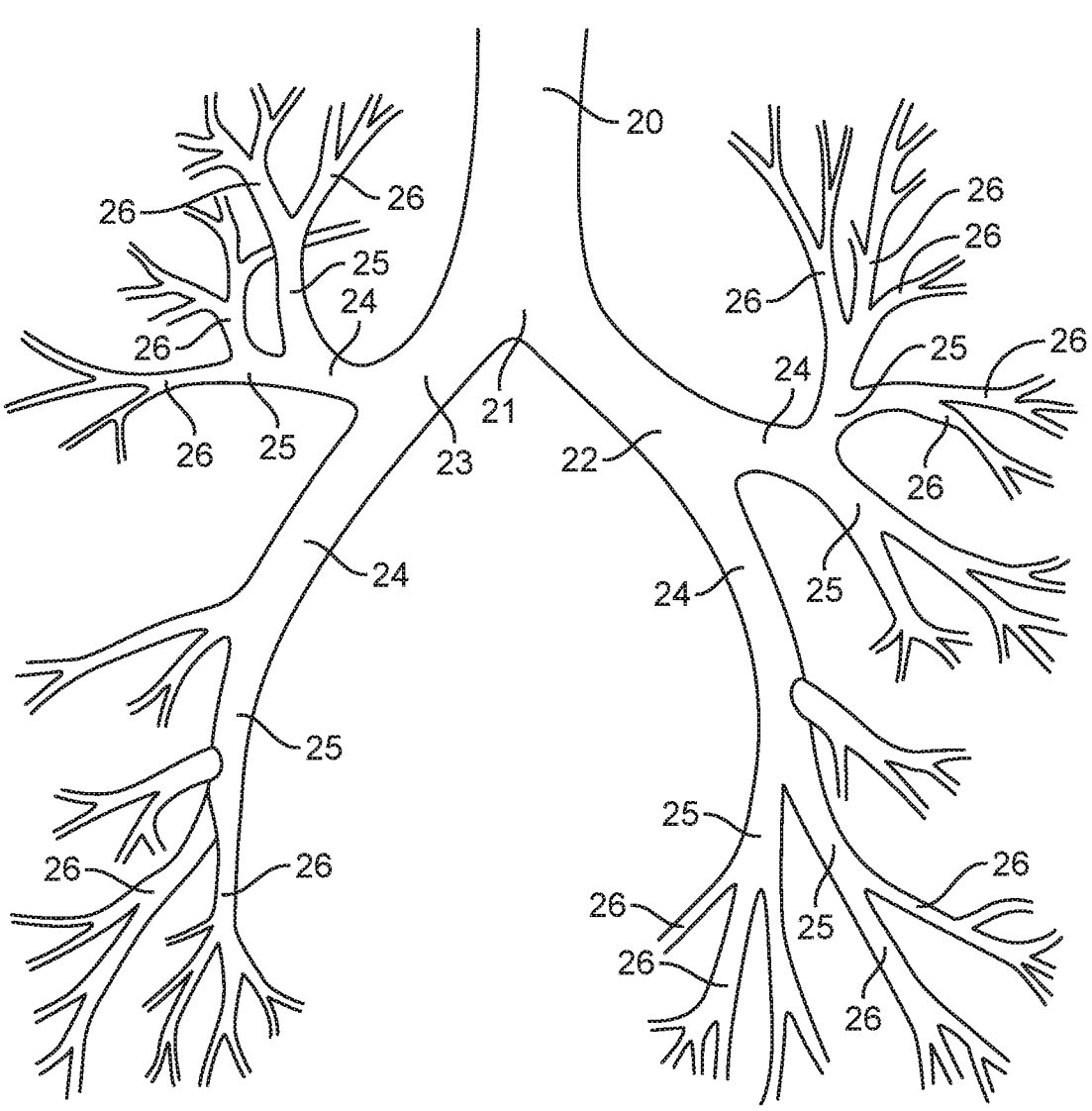
FIG. 2 illustrates the human lung airway tree.

FIG. 2 illustrates an airway tree of a typical human lung. The trachea 20 is the major airway that leads to the lungs. The trachea 20 also referred to as the zero generation of airways. The trachea is typically about 18 to 25 mm in diameter and about 120 mm long. At the carina 21, the trachea bifurcates into the left main bronchus 22 and the right main bronchus 23, referred to as the $1^{st}$ generation airways. The main bronchi 22, 23 typically are between 12 and 15 mm in diameter and are about 50 mm long. The main bronchi 22, 23 branch into lobar airways 24, also referred to as 2<sup>nd</sup> generation airways, which typically are about 8 to 12 mm in diameter and about 20 mm long. The lobar airways branch to the segmental airways 25, also referred to as 3<sup>rd</sup> generation airways, these airways typically are between 5 to 8 mm in diameter and are about 8 mm long. The segmental airways 25 branch into sub-segmental airways 26, referred to as 4<sup>th</sup> generation airways, that are between 4 to 5 mm in diameter and finally, the sub-sub-segmental airways, referred to as the 5<sup>th</sup> generation airways, branch off of the sub-segmental airways. These can be as small as 2 mm in diameter. The treatments described in this specification are intended to treat all of the aforementioned airways including those of the 6<sup>th</sup>, 7<sup>th</sup> and 8<sup>th</sup> generation in the airway tree (which may be referred to as part of the terminal bronchioles, which encompass the 5<sup>th</sup> through 16<sup>th</sup> generation airways). In some cases, treatments can be performed in tissue up to the 30<sup>th</sup> generation airways. In exemplary embodiments, treatments are performed in the 3<sup>th</sup>, 4<sup>th</sup>, 5<sup>th</sup>, and/or 6<sup>th</sup> generation airways. In some embodiments, treatments are performed in airways where goblet cells are located.

The tracheobronchial tree is the anatomical and functional segment of the respiratory system that conducts air from the larger upper airways to the lung parenchyma. It is comprised of the trachea and various intrapulmonary airways, including the bronchi, bronchioles and terminal bronchioles. The trachea and bronchi have cartilaginous walls which makes them thick, fibrous and this allows them to maintain patency during breathing. Bronchi undergo multiple divisions and eventually give rise to the terminal bronchioles, which by definition, lack cartilage. The most distal respiratory bronchioles and alveoli are where gas exchanges into and out of the blood stream.

As bronchi divide into smaller airways, the respiratory epithelium undergoes histological changes and gives rise to terminal bronchioles. The 17th to 19th generations of bronchioles constitute the transitional zone. These bronchioles enter pyramid-shaped pulmonary lobules separated from one another by a thin septum, with the apex directed toward the hilum, comprising 5-7 terminal bronchioles. The last 2-3 generations of bronchioles have some alveoli in their walls and make up the respiratory zone. The area of the lung that is distal to a terminal bronchiole is termed the acinus. The final division is called the respiratory bronchiole, which further branches into multiple alveolar ducts. Alveoli, the functional units of the respiratory system, start appearing at the level of the respiratory bronchioles. This is where the majority of gas is exchanged. It is important to note that the majority of the healthy lung volume is comprised of alveoli tissue. The airway network branches from the trachea through the various portions of the lung to supply a volume of oxygen and to expel carbon dioxide from alveoli that are positioned almost everywhere within the lung. Only a small volume of the lung is occupied by the airway tree and the arterial network that transports blood from the right side of the heart through the lung to the left side of the heart.

Figure 3:
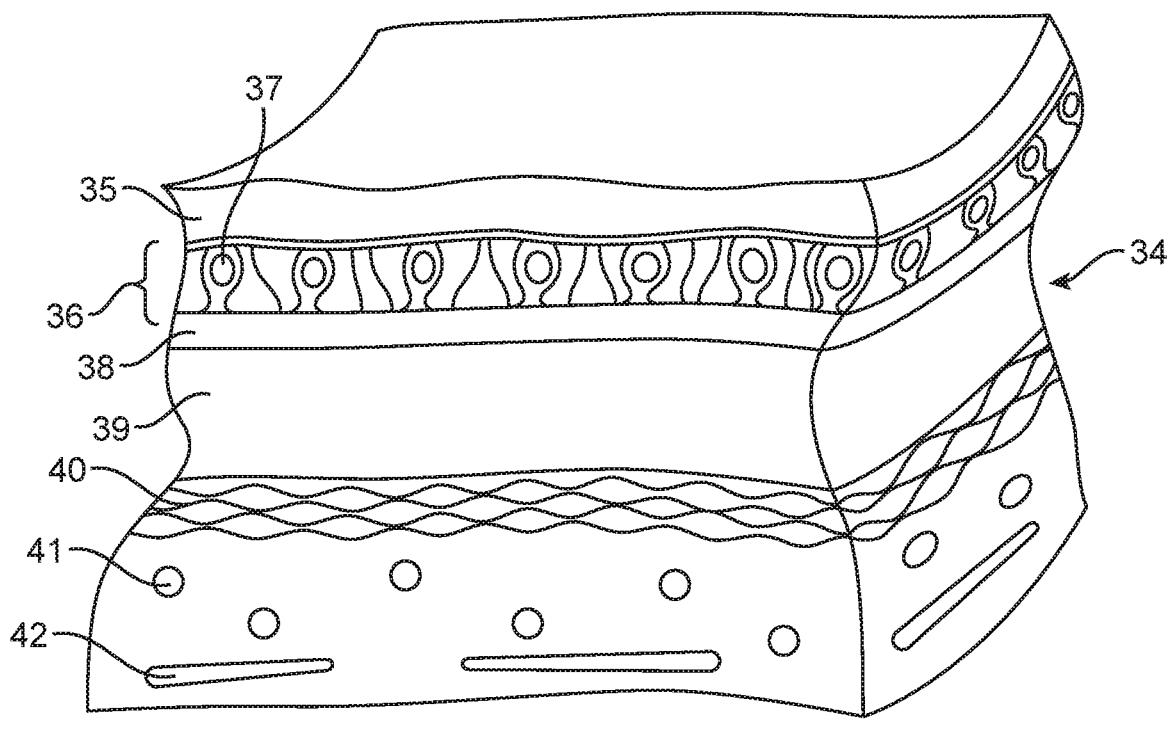
FIG. 3 illustrates a cross-section of a human lung airway wall.

FIG. 3 illustrates a cross-section of a typical airway wall 34. The main structure of airways is supported by cartilage 42 that resides in the less central part of the airway wall, along with glands 41 and a smooth muscle 40 layer. The lamina propria 39 separates the smooth muscle 40 from the basement membrane 38. The inner lumen of the lung airways is lined by mucus 35 and epithelium 36. The epithelium contains goblet cells 37 that produce the mucus 35.

Figure 4:
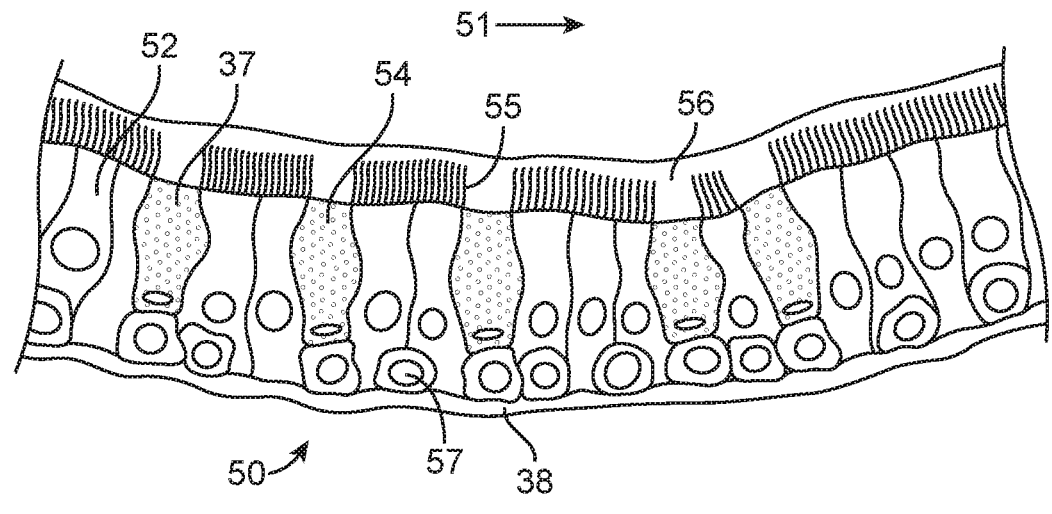
FIG. 4 illustrates a cross-section of healthy human epithelium.

FIG. 4 illustrates a cross-section of a typical healthy epithelium 50. In healthy people, the basement membrane 38, basal cells 57, and ciliate cells 52 form the airway basal lamina. Cilia 55 grows over the surface of the epithelium 50 except where goblet cells 37 are exposed to the airway lumen 51. The goblet cells 37 contain MCV's 54 that produce and secrete a mucus layer 56 on the surface of the airway lumen 51.

Figure 5:
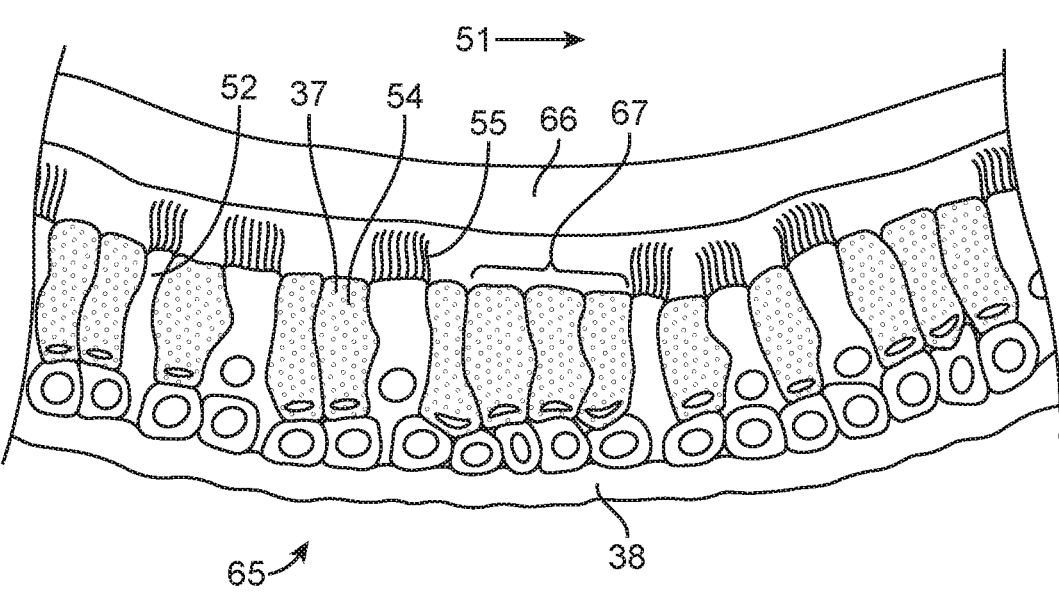
FIG. 5 illustrates a cross-section of human epithelium in a bronchitis patient.

FIG. 5 illustrates a cross-section of bronchitis epithelium 65. With prolonged cigarette smoking, the airways are chronically irritated. With repeated irritation events, the epithelium 65 of the lung produces an increased numbers of goblet cells, goblet cell hyperplasia 67, that produce increased volumes of mucus (e.g. mucus 56 as shown in FIG. 4). FIG. 5 illustrates the added mucus production as an over-production mucus layer 66. The cilia 55 normally works to transport mucus (e.g. mucus 56 as shown in FIG. 4) towards the trachea (e.g. trachea 20 as shown in FIG. 2) where it can be coughed out. This is the lung's main mechanism to repel noxious particles and contaminants. After a number of inflammation events, the airway walls become scarred, the cilia 55 fail to regenerate which eliminates the main means to transport mucus (e.g. mucus 56 as shown in FIG. 4) out of the lung. With a reduction of mucus transport, the mucus (e.g. mucus 56 as shown in FIG. 4) accumulates and collects and harbors bacteria that culminates in repeated infections. The infections cause coughing and the coughing further inflames the airways. This cycle continues until the body generates goblet cell hyperplasia 67 and other cells in the airway walls to fight back the encroachment of foreign materials, inflammation and infections. This cycle continues until the patient is coughing for long periods or possibly continuously. The cycle causes the classic tissue wound healing in the airway walls that is constantly remodeled with additional goblet cell hyperplasia 67 and other cells that produce mucus (e.g. mucus 56 as shown in FIG. 4) and the airways walls gradually thicken and restrict air flow. Cilia 55 coverage, in the airway lumen 51 surface, is compromised due to the goblet cell hyperplasia 67, which further exacerbates the bronchitis problem. These patients remain chronically infected with little means to expectorate the mucus (e.g. mucus 56 as shown in FIG. 4) that is produced. This leaves the patients lungs inflamed and reduces breathing capacity with little chance of normal healing, with added mucus production as an over-production mucus layer 66. A visual inspection of FIGS. 4 and 5 shows that the bronchitis epithelium 65 of FIG. 5 contains much less cilia 55 than the normal, healthy epithelium 50 of FIG. 4.

Figure 6:
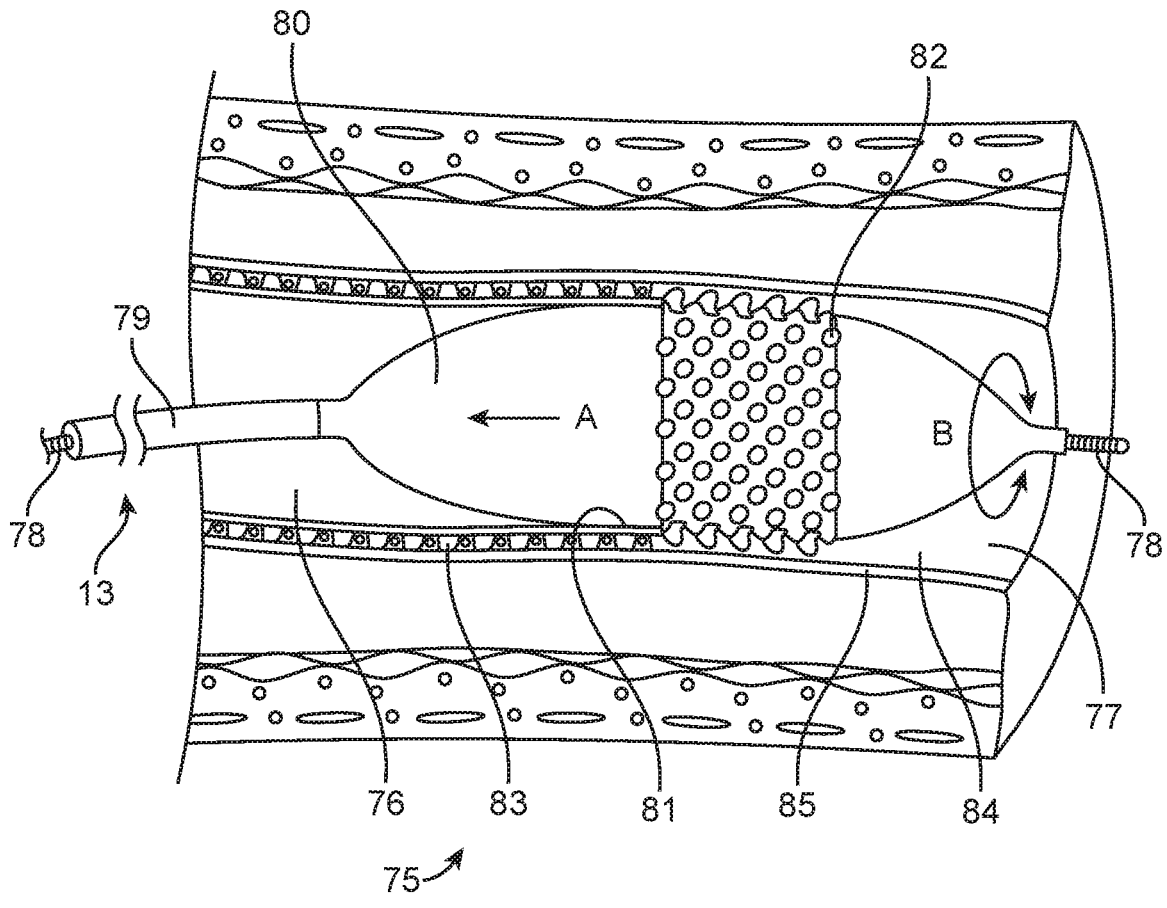
FIG. 6 illustrates an embodiment of a pulmonary treatment device comprising an elongate balloon catheter with abrasive surface contact in tissue.

FIG. 6 illustrates a bronchitis airway cross-section 75 with a pulmonary treatment device 13 deployed in the airway 75. The epithelium layer 83, attached to the proximal airway lumen wall 76, requires treatment as bronchitis has manifested with goblet cell hyperplasia (e.g. hyperplasia 67 as shown in FIG. 5). The pulmonary treatment device 13 comprises a balloon body 80 with abrasive grit 82 that is bonded to the balloon surface 81 of the balloon body 80. The balloon body 80 is bonded to a balloon catheter shaft 79 which has been advanced over a guidewire 78. The pulmonary treatment device 13 may be rotated, advanced distally or proximally along the airway central longitudinal axis, and/or rotationally oscillated or linearly oscillated, inside the airway 75 while it is being advanced or retracted. For example, as depicted in FIG. 6, the pulmonary treatment device 13 is being pulled or retracted proximally (as indicated by arrow A) while being rotationally oscillated (as indicated by arrow B). In some cases, a treatment may include pushing the device 13 distally in a direction opposite of arrow A to produce an abrading action between the abrasive grit 82 and the airway tissue. As shown in FIG. 6, the abrasive grit 82 is abrading off the epithelium layer 83. The distal airway lumen 77 wall has been stripped of the epithelium layer 83. This is shown as abraded airway wall 84 which leaves the exposed basement membrane 85. The pulmonary treatment device 13 abrades off the epithelium layer 83 to cause epithelium layer 83 remodeling in a configuration with a reduced (e.g. normal, healthy) number of goblet cells (e.g. goblet cells 37 as depicted in FIG. 4). By eliminating goblet cells and the goblet cell hyperplasia (e.g. goblet cell hyperplasia 67 as depicted in FIG. 5), the treatment may reduce mucus (e.g. mucus 35 as depicted in FIG. 4) and/or an over-production mucus layer (e.g. over-production mucus layer 66 as depicted in FIG. 5) and associated bacteria to promote drying of the patient's airway tree and promote wound healing. All of this will reduce inflammation in the patient which will produce one or more of the changes in treated patient, listed in the summary of the invention section of this specification. In some cases, a balloon catheter shaft 79 and/or balloon body 80 (e.g. FIGS. 6, 7A-D) may be referred to as an elongate member. In some cases, the abrasive grit 82 can be referred to as an abrasion feature.

Figures 7A, 7B:
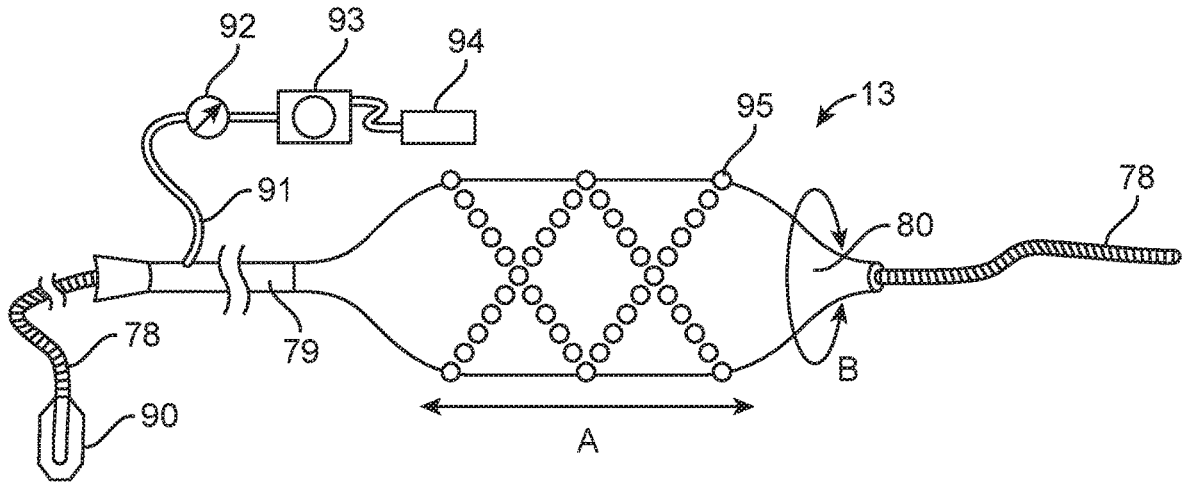
FIGS. 7A-D illustrates embodiments of the pulmonary treatment devices expanded to contact tissue and presenting methods of control and abrasive surfaces.

FIG. 7A illustrates a pulmonary treatment device 13 comprising a balloon body 80 that is bonded to a balloon catheter shaft 79. The pulmonary treatment device 13 is deliverable over a guidewire or guidewire shaft 78 with a guidewire hub 90. The balloon body 80 is inflated by a gas or fluid that include water, saline, silicone or other biocompatible fluid or air, nitrogen, oxygen or other biocompatible gas that is communicated through the balloon inflation hose 91. In this way, hose 91 provides pressurized gas to the balloon. The gas or fluid may be maintained at a constant pressure by adjusting a pressure regulator 92, which may include a pressure gauge. The pressure may also be cycled in pulses to cause the balloon to oscillate between two or more diameters to cause abrasion in a way that minimizes large scale motions and tissue trauma. The change in diameter within each pressure pulse cycle may be as small as 0.01 mm or as large as 28 mm, and in exemplary embodiments may be between 0.1 and 15 mm. The frequency of the pulses may be between 0.25 and 5000 cycles per second, and in exemplary embodiments may be between 1 and 50 Hz. The pressure may be regulated or pulsed between 0.001 and 600 pounds force per square inch. The pressure will be maintained low for compliant balloons and higher for non-compliant balloons. The pressure may be supplied using a pump 93. In some cases, pump 93 is an electric pump. The pump may be powered using direct current energy and the source may be from a battery 94. In some cases, the pump 93 can be operated in a pulsating manner, so that the pressure within the balloon body 80 increases and decreases in a cyclical, oscillatory, or sinusoidal manner. In some cases, the pump 93 can be operated in a manner such that a vibrating motion is produced on the surface of the balloon body 80. The bonded abrasive grit pattern 95 is as a crossing linear abrasive grit pattern 95 to enhance abrasion effect on the lung airway lumen (e.g. airway lumen 51 as depicted in FIG. 5) while the balloon body 80 is being inflated and expanded. The grit pattern 95 can contact the airway wall epithelium layer (e.g. airway wall epithelium layer 83 as depicted in FIG. 6) to abrade the wall so that only the exposed basement membrane (e.g. exposed basement membrane 85 as depicted in FIG. 6) remains. In some cases, an abrasion effect can be created or enhanced by moving the balloon body 80 in a linear fashion as indicated by arrow A, and/or in a rotationally oscillatory fashion as indicated by arrow B. Embodiments of the present invention encompass any of a variety of bonded abrasive grit patterns 95, including rings, stripes, curved lines, straight lines, chevrons, sinusoidal lines, circular spots, non-circular spots, and the like. In some cases, expansion and/or contraction of the balloon body 80 can cause the pattern 95 to move, shift, or otherwise change, and such a changing pattern can contribute to an abrading action of the grit pattern 95. For example, the angles and/or alignment of the crossing linear abrasive grit pattern 95 may change. In some embodiments, sufficient abrading action for a treatment may be achieved by simply inflating and/or deflating the balloon body 80, without otherwise scraping the tissue by linearly and/or rotationally moving the balloon body 80. In some cases, the abrasive grit pattern 95 can be referred to as an abrasion feature.

FIG. 7B illustrates a pulmonary treatment device 13 comprising a balloon body 80 that is bonded to a balloon catheter shaft 79. The pulmonary treatment device 13 is deliverable over a guidewire 78. The balloon body 80 is inflated by a gas or fluid that include water, saline, silicone or other biocompatible fluid or air, nitrogen, oxygen or other biocompatible gas that is communicated through the balloon inflation hose 91. The gas or fluid may be maintained at a constant pressure by adjusting a pressure regulator 92. The pressure may be supplied using a pump 93. The pump may be powered using alternating current energy and the source may be from a power system grid such as the power commonly found at wall outlets. As illustrated in FIG. 7B, the energy is supplied using an electrical cable 135 and electrical wall plug 100. The abrasive media that is bonded to the balloon body 80 is a band comprising abrasive mesh 101 which may be made from any polymer or film that may be expanded and which has abrasive grit 82 properties of material incorporated in the abrasive mesh 101. In some cases, an abrasive mesh 101 may include fine, flexible sharp-edged steel or metallic filaments. The raised edges of abrasive media 125 contact the airway wall epithelium layer (e.g. airway wall epithelium layer 83 as depicted in FIG. 6) to abrade the wall so that only the exposed basement membrane (e.g. exposed basement membrane 85 as depicted in FIG. 6) remains. In some cases, an abrasion effect can be created or enhanced by moving the balloon body 80 in a linear fashion as indicated by arrow A, and/or in a rotationally oscillatory fashion as indicated by arrow B.

As depicted in FIG. 7B, the abrasive mesh 101 occupies a relatively small percentage (e.g. less than 30%) of the surface area of the balloon 80. In some cases, the percentage of surface area of the balloon body 80 which the abrasive mesh 101 occupies can impact the abrading depth of the device 13, for example when the uncovered portion of the balloon body 80 contacts and/or presses against the airway wall and the mesh 101 is stretched or contracted due to inflation/deflation of the balloon body 80. In some instances, the uncovered proximal surface 86 and/or distal surface 87 of the balloon body 80 can operate as a bearing surface against the airway wall. In some cases, the uncovered proximal surface 86 and/or distal surface 87 of the balloon body 80 can operate to limit the depth to which the mesh 101 penetrates into the airway wall. In some cases, the abrasive mesh 101 can be referred to as an abrasion feature.

Figure 7C:
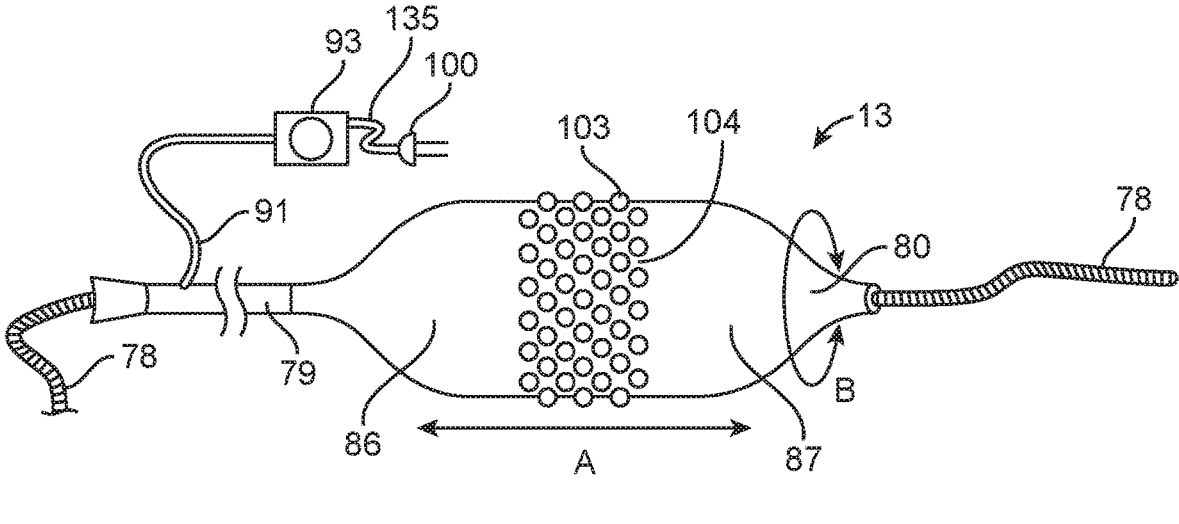

FIG. 7C illustrates a pulmonary treatment device 13 comprising a balloon body 80 that is bonded to a balloon catheter shaft 79. The pulmonary treatment device 13 is deliverable over a guidewire 78. The balloon body 80 is inflated by a gas or fluid that include water, saline, silicone or other biocompatible fluid or air, nitrogen, oxygen or other biocompatible gas that is communicated through the balloon inflation hose 91. The gas or fluid may be maintained at a constant pressure by adjusting a pressure regulator 92. The pressure may be supplied using a pump 93. The pump may be powered using alternating current energy and the source may be from a power system grid such as the power commonly found at wall outlets. As illustrated in FIG. 7C, the energy is supplied using an electrical cable 135 and electrical wall plug 100. The abrasive media that is bonded to the balloon body 80 is a band comprising abrasive grit of mixed size 103. The abrasive grit of mixed size 103 may be bonded on the balloon body 80 as an irregular sized band of abrasive grit 104 so the point of contact with the airway epithelium layer (e.g. epithelium layer 83 as depicted in FIG. 6) may vary as the expanded balloon body 80 is rotated. The abrasive grit of mixed size 103 contact the airway wall epithelium layer (e.g. airway wall epithelium layer 83 as depicted in FIG. 6) to abrade the wall so that only the exposed basement membrane (e.g. exposed basement membrane 85 as depicted in FIG. 6) remains. In some cases, an abrasion effect can be created or enhanced by moving the balloon body 80 in a linear fashion as indicated by arrow A, and/or in a rotationally oscillatory fashion as indicated by arrow B. In some cases, the abrasive grit 104 can be referred to as an abrasion feature.

In some cases, the size, distribution, and/or composition of the abrasive grit of mixed size 103 can be selected so as to provide for a depth control feature. For example, some grit 103 compositions may provide for deeper abrading, whereas other grit 103 compositions may provide for shallower abrading. If the grit 103 size is too small, little or no abrading may occur. If the grit 103 size is too large, the grit may unduly dig into and damage the airway wall surface.

As depicted in FIG. 7C, the band of abrasive grit 104 occupies a relatively small percentage (e.g. less than 30%) of the surface area of the balloon 80. In some cases, the percentage of surface area of the balloon body 80 which the band of abrasive grit 104 occupies can impact the abrading depth of the device 13, for example when the uncovered portion of the balloon body 80 contacts and/or presses against the airway wall and the band of abrasive grit 104 is stretched or contracted due to inflation/deflation of the balloon body 80. In some instances, the uncovered proximal surface 86 and/or distal surface 87 of the balloon body 80 can operate as a bearing surface against the airway wall. In some cases, the uncovered proximal surface 86 and/or distal surface 87 of the balloon body 80 can operate to limit the depth to which the band of abrasive grit 104 penetrates into the airway wall. The embodiment depicted in FIG. 7C includes a single band of abrasive grit 104. In some embodiments, a treatment device may include multiple bands of abrasive grit.

Figure 7D:
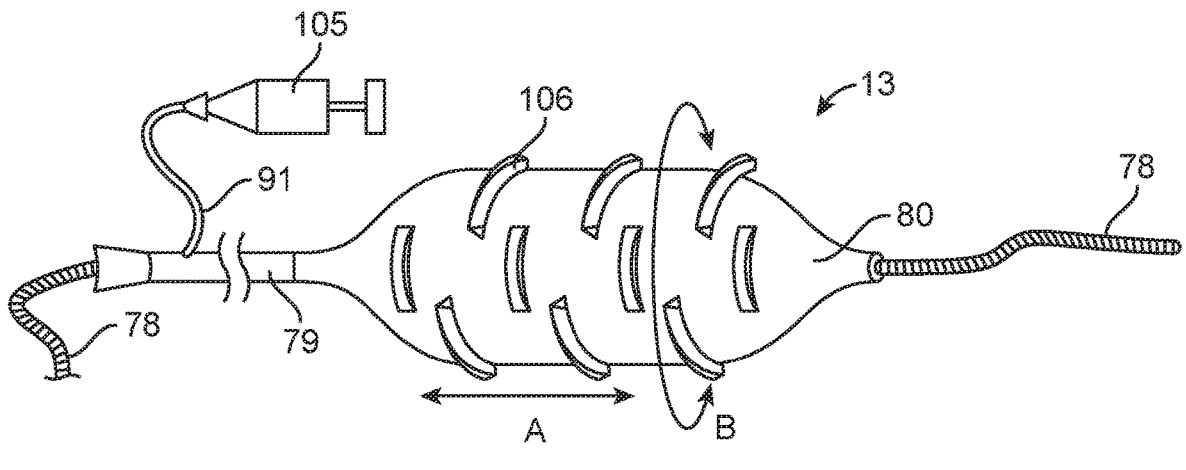

FIG. 7D illustrates a pulmonary treatment device 13 comprising a balloon body 80 that is bonded to a balloon catheter shaft 79. The pulmonary treatment device 13 is deliverable over a guidewire 78. The balloon body 80 is inflated by a gas or fluid that include water, saline, silicone or other biocompatible fluid or air, nitrogen, oxygen or other biocompatible gas that is communicated through the balloon inflation hose 91. The gas or fluid pressure may be supplied using a syringe pressure source 105. In some cases, the syringe pressure source 105 is a hand operated device. In use, the syringe 105 could be pumped or actuated one or more times so as to inflate the balloon body 80, the pressure source 105 could be locked so as to retain a certain amount of pressure in the balloon body 80, and the balloon body 80 could be pulled through the airway and/or oscillated in a rotary and/or linear fashion (e.g. via a motor drive operatively coupled with the balloon catheter shaft 79). The abrasive media that is bonded to the balloon body 80 is a series of metal, plastic, ceramic, hard rubber, rope, glass, or other biocompatible materials that provide raised edges 106 that scrape the epithelium layer (e.g. epithelium layer 83 as depicted in FIG. 6) as the balloon body 80 is expanded, rotated or moved in a linear fashion. The raised edges 106 contact the airway wall epithelium layer (e.g. airway wall epithelium layer 83 as depicted in FIG. 6) to abrade the wall so that only the exposed basement membrane (e.g. exposed basement membrane 85 as depicted in FIG. 6) remains. In some cases, an abrasion effect can be created or enhanced by moving the balloon body 80 in a linear fashion as indicated by arrow A, and/or in a rotationally oscillatory fashion as indicated by arrow B. In some cases, raised edges 106 can be features of a blade element that is attached to the balloon exterior and that act as scrapers during balloon expansion or while the balloon is dragged along a longitudinal axis of the airway. In some cases, the raised edges 106 can be referred to as an abrasion feature.

According to some embodiments, balloon bodies (e.g. balloon body 80) can be compliant, non-compliant (i.e. rigid), or semi-compliant (i.e. semi-rigid). Subjected to a given amount of atmospheric pressure, a compliant balloon body will assume a larger diameter as compared with a non-compliant balloon which will assume a smaller diameter. Hence, in devices where the balloon body is relatively more compliant, the bonded abrasive grit 82, the abrading grit pattern 95, the abrasive mesh 101, the band of abrasive grit 104, the raised edges 106, or other abrasive feature or elements disclosed herein may be pushed further into or with greater force against the airway wall, as compared with devices where the balloon body is relatively less compliant.

In some cases, when the balloon body 80 is inflated, only the abrasive element or feature contacts and penetrates the airway wall. That is to say, the proximal surface 86 and distal surface 87 of the balloon body 80 do not contact the airway wall, until the desired abrading depth, as determined by the depth of the abrasive element or feature, is achieved.

Figure 8A:
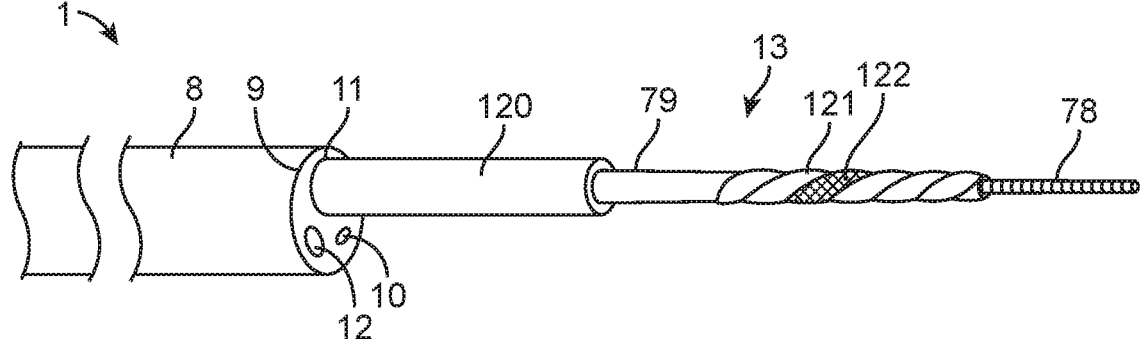
FIG. 8A illustrates a pulmonary treatment device in an easily deliverable undeployed configuration.

FIG. 8A illustrates aspects of a pulmonary treatment device 13 according to embodiments of the present invention. As shown here, treatment device 13 can be inserted through a flexible trunk 8 of a bronchoscope 1, and advanced until it exits out a channel exit port 11 of a distal scope tip 9 of the scope 1. As shown here, scope 1 includes a camera 10 and a light source 12. The treatment device 13 includes or can be positioned within a guide catheter 120, and can include a balloon catheter shaft 79, an uninflated balloon 121, and a folded abrasive mesh 122 coupled with the balloon 121. The treatment device 13 can also include or be positioned along a guidewire 78. In some cases, the guidewire 78 is optional. Guide catheter 120 can operate to guide placement of the balloon 121. In some cases, the bronchoscope 1 can be used as a catheter, to cross the vocal cords, when the treatment device 13 is delivered to a treatment location within the patient lung airway. In some cases, the bronchoscope 1 can be left in place during a treatment procedure, and a bronchoscopist, physician, surgeon, or other operator may exchange the treatment device 13 with a different device during the procedure. In some cases, a radiologist can perform a treatment procedure, without using a bronchoscope 1.

As depicted in FIG. 8A, a guidewire 78 can be placed through the guide catheter 120. In this way, the surgeon or operator can advance the catheter 120 deeply into the airway tree, and place the balloon catheter shaft 79 onto the guidewire 78, and advance the balloon catheter shaft 79 through the guide catheter 120. Such techniques can help to preserve the airway walls from being damaged.

Figure 8B:
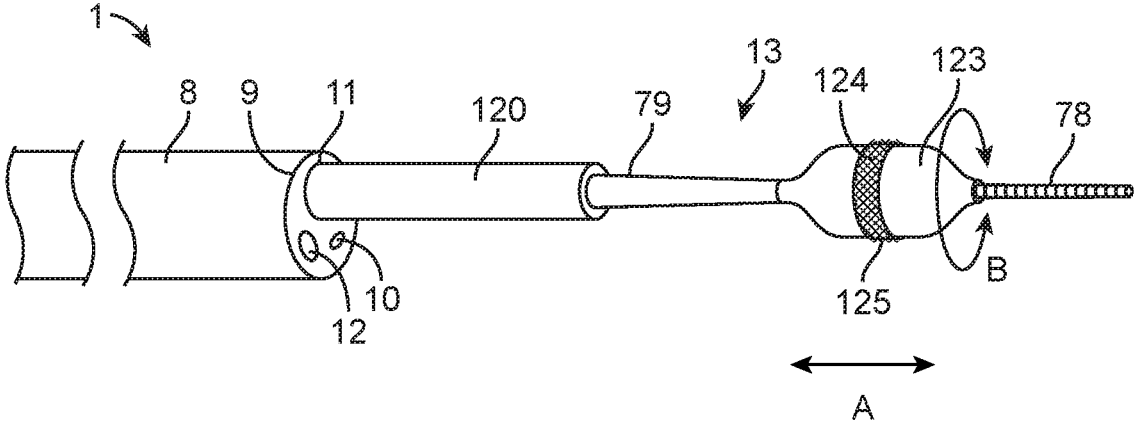
FIG. 8B illustrates a pulmonary treatment device in a deployed configuration.

FIG. 8B illustrates aspects of a pulmonary treatment device 13 according to embodiments of the present invention. As shown here, treatment device 13 is inserted through a flexible trunk 8 of a bronchoscope 1, and advanced until it exits out a channel exit port 11 of a distal scope tip 9 of the scope 1. As shown here, scope 1 includes a camera 10 and a light source 12. The treatment device 13 includes or can be positioned within a guide catheter 120, and can include a balloon catheter shaft 79, an inflated balloon 123, and an expanded abrasive mesh 124 coupled with the balloon 123. The expanded abrasive mesh 124 includes raised edges 125 of abrasive media. The treatment device 13 can also include or be positioned along a guidewire 78. In some cases, the guidewire 78 is optional. A visual inspection of FIGS. 8A and 8B shows that the uninflated balloon 121 of FIG. 8A can be inflated to become the inflated balloon 123 of FIG. 8B, and as a result, the folded abrasive mesh 122 of FIG. 8A can be unfolded and enlarged to become the expanded abrasive surface 124 of FIG. 8B. Expansion of the mesh can lead to abrasion of the airway wall epithelium layer. As illustrated in FIG. 8B, an abrasion effect can be created or enhanced by moving the inflated balloon 123 in a linear fashion as indicated by arrow A, and/or in a rotationally oscillatory fashion as indicated by arrow B. In some cases, a balloon catheter shaft 79 and/or balloon 123 (e.g. FIGS. 8A,B) may be referred to as an elongate member. In some cases, the expanded abrasive surface 124 can be referred to as an abrasion feature.

FIG. 9 illustrates aspects of a system 200 for treating a patient. System 200 includes a bronchoscope 1 having a flexible trunk 8 with a working channel exit port 11. As shown here, a treatment device 13 (or other endobronchial tool) can be inserted into a channel insertion port 7 of a bronchoscope 1, through a flexible trunk 8 of a broncho-scope 1, and advanced until it exits out a channel exit port 11 of a distal scope tip of the scope 1. The bronchoscope 1 has a control handle 4 and is coupled with a video monitor 138 via a data cable 2. As shown here, monitor 138 can provide a bronchoscope image 137, which allows the operator to see what is happening within the patient (e.g. in the lung airways). Treatment device 13 includes a balloon 80 having an abrasive grit of mixed size 103 coupled thereto, which is positioned along a guidewire 78. The system 200 also includes a syringe pressure source 105 for the balloon 80, coupled with a balloon inflation hose 91. In some cases, balloon catheter shaft 79 includes a separate lumen through which the balloon 80 can be inflated and/or deflated. As shown here, system 200 includes a balloon catheter hub 130 and a motor assembly 131 having a trigger switch 132. In use, the operator can actuate the switch 132 so as to control the motor assembly 131. Such actuation can cause the balloon 80 to rotate, translate, and/or inflate/deflate in an oscillatory or vibrational manner, as described elsewhere herein. Guidewire 78 can extend proximally from the balloon catheter hub 130 and distally from the balloon 80. As shown here, balloon catheter hub 130 can be coupled with a balloon catheter shaft 78 which is inserted into a channel insertion port 7 of the bronchoscope 1. Motor assembly 131 is coupled with a battery 134 via a power cable 133. The battery 134 operates to energize the motor assembly 131. A wall outlet plug 136 can be coupled with the battery 134 via an electrical cable 135. In some cases, battery 134 is a rechargeable battery. In some cases, system 200 may include an AC/DC converter in place of the battery 134. When the wall outlet plug 136 is plugged into a wall outlet, electricity from the wall outlet can be used to recharge the battery 134 or to directly operate the motor assembly 131. In the embodiment depicted in FIG. 9, the system 200 does not include a guide catheter (e.g. such as guide catheter 120 depicted in FIGS. 8A and 8B). In some cases, a balloon catheter shaft 79 and/or balloon 80 (e.g. FIG. 9) may be referred to as an elongate member. In some cases, the band comprising abrasive grit of mixed size 103 can be referred to as an abrasion feature.

Figure 10:
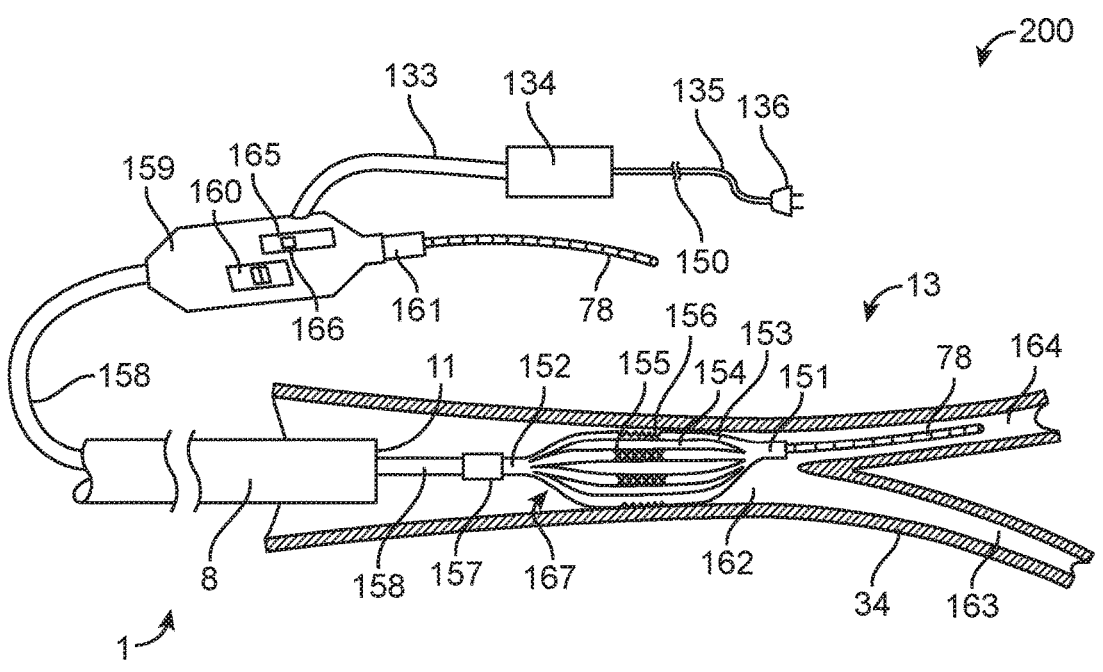
FIG. 10 illustrates a pulmonary treatment system with an expandable abrasive basket.

FIG. 10 illustrates aspects of a system 200 for treating a patient. System 200 includes a bronchoscope 1 having a flexible trunk 8 with a working channel exit port 11. As shown here, treatment device 13 can be inserted through a flexible trunk 8 of a bronchoscope 1, and advanced until it exits out a channel exit port 11 of a distal scope tip of the scope 1. Treatment device 13 includes an expandable abrading device 167 having a distal end 151, a proximal end 152, and a plurality of elastic spring elements 153 disposed between the distal end 151 and the proximal end 152. The expandable abrading device 167 also includes gaps 154 between adjacent elastic spring elements 153, and abrasive material 155 disposed on the elastic spring elements 153. In some cases, abrasive material 155 is glued to or bonded with the elastic spring elements 153. The abrasive material 155 provides raised abrasive edges 156. In some cases, abrasive edges 156 can be provided by cutting or etching shapes or patterns in the spring elements 153 (e.g. without requiring the presence of a separate abrasive material 155). For example, such abrasive shapes or patterns for the abrasive edges 156 can be created by cutting or arc welding the spring elements 153. In some cases, the patterning or etching can cause craters on the spring elements 153 which are sharp. The expandable abrading device 167 is placed within an airway lumen 162, proximal to an airway branch 163 and a next generation airway 164. The proximal end 152 of the expandable abrading device 167 is coupled with an abrader catheter shaft 158 via a connector hub 157. The abrader catheter shaft 158 is coupled with a motion driving hand-piece 159. The abrader catheter shaft 158 can include a metallic or polymeric material, according to some embodiments. In some cases, a handpiece 159 is graspable by a user so as to manually applying a linear and/or rotational force.

As shown here, the motion driving handpiece 159 includes a slider switch 160, a guidewire exit port 161, and a pull wire actuator switch 165 having an actuator switch button or slider 166. In use, the operator can actuate the switch 165 so as to control the motor driving handpiece 159. Such actuation can cause the expandable abrading device 167 to rotate, translate, and/or expand/contract in an oscillatory or vibrational manner, as described elsewhere herein. In some cases, actuation of the button or slider 166 can adjust the frequency, amplitude, and/or direction in which the expandable abrading device 167 oscillates, vibrates, or moves.

A guidewire 78 can extend proximally from the guidewire exit port 161 of the motion driving handpiece 159 and distally from the distal end 151 of the expandable abrading device 167. The motion driving handpiece 159 is coupled with a battery 134 via a power cable 133. The battery 134 operates to energize the motion driving handpiece 159. A wall outlet plug 136 can be coupled with the battery 134 via one or more electrical cables 135. In some cases, electrical cables 135 can include or be joined by connectors 150. In some cases, battery 134 is a rechargeable battery. In some cases, system 200 may include an AC/DC converter in place of the battery 134. When the wall outlet plug 136 is plugged into a wall outlet, electricity from the wall outlet can be used to recharge the battery 134 or to directly operate the motion driving handpiece 159.

In some cases, the spring elements 153 can be made from round wire and in some embodiments the round wire has been flattened at one or more locations. Likewise, in other embodiments, the spring elements are made from ribbon which already has a flattened shape. In such instances, the ribbon can optionally be twisted. In some cases, the spring elements 153 can be provided by a laser cut tube (e.g. a slitted tube), a nitinol material, a spring steel material, or any shape memory material. As shown here, when expandable abrading device 167 is expanded, the shape of device 167 is similar to that of an expanded or inflated balloon as disclosed elsewhere herein. In some cases, a balloon catheter shaft 79 and/or balloon body 123 (e.g. FIGS. 8A,B) may be referred to as an elongate member. In some cases, the abrasive material 155 or abrasive edges 156 can be referred to as an abrasion feature.

Figure 11:
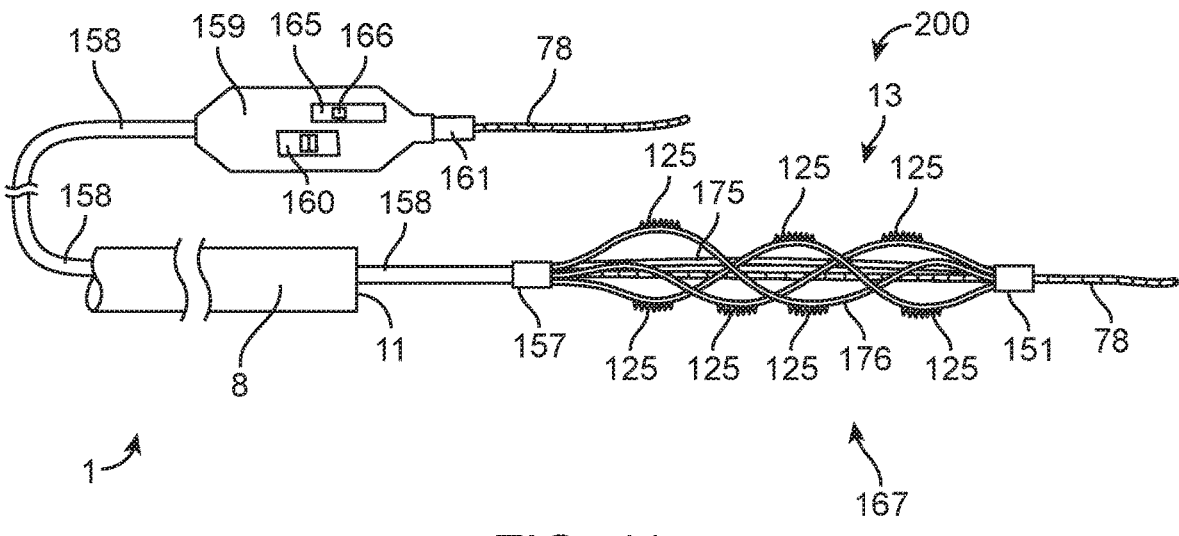
FIG. 11 illustrates a pulmonary treatment system with twisted elastic strands and expansion pull wire.

FIG. 11 illustrates aspects of a system 200 for treating a patient. System 200 includes a bronchoscope 1 having a flexible trunk 8 with a working channel exit port 11. As shown here, treatment device 13 can be inserted through a flexible trunk 8 of a bronchoscope 1, and advanced until it exits out a channel exit port 11 of a distal scope tip of the scope 1. Treatment device 13 includes a connector hub 157, an expandable abrading device 167, and a pull wire 175. The expandable abrading device 167 has a distal end 151, a plurality of abrasive strands 176 disposed between the distal end 151 and the connector hub 157, and raised edges of abrasive media 125 disposed along the abrasive strands 176. The abrasive strands 176 are coupled with an abrader catheter shaft 158 via the connector hub 157. The abrader catheter shaft 158 is coupled with a motion driving handpiece 159. As shown here, the motion driving handpiece 159 includes a slider switch 160, a guidewire exit port 161, and a pull wire actuator switch 165 having an actuator switch button 166 that controls operation of the pull wire 175. A guidewire 78 can extend proximally from the guidewire exit port 161 of the motion driving handpiece 159 and distally from the distal end 151 of the expandable abrading device 167. The motion driving handpiece 159 can be coupled with a battery (e.g. a rechargeable battery) or an AC/DC converter, as discussed elsewhere herein. In some cases, a handpiece 159 is graspable by a user so as to manually applying a linear and/or rotational force.

According to some embodiments, the abrading device 167 can be provided as a nitinol wire basket. In some cases, abrasive strands 176 can include abrasive edges provided by cutting or etching shapes or patterns in the strands 176 (e.g. without requiring the presence of a separate abrasive media 125). For example, such abrasive shapes or patterns for the abrasive edges can be created by cutting or arc welding the strands 176. In some cases, the patterning or etching can cause craters on the strands 176 which are sharp. The strands 176 can be made from round wire and in some embodiments the round wire has been flattened at one or more locations. Likewise, in other embodiments, the strands 176 are made from ribbon which already has a flattened shape. In such instances, the ribbon can optionally be twisted. Strands 176 can also be fashioned from wire, such as round-section wire, or square or rectangular section ribbon. According to some embodiments, the strands 176 can be provided in any of a variety of geometric configurations, including helical shapes, random shapes, egg-beater shapes, sinusoidal shapes, troposkein shapes, and the like. Operation of the pull wire 175 can change the overall shape and/or diameter of the abrading device 167. In some embodiments, the pull wire 175 can be actuated to expand the diameter of the abrading device 167, for example by drawing distal end 151 toward connector hub 157, and the abrading device 167 could then be oscillated and/or drawn proximally along the airway, as described elsewhere herein.

As shown here, the motion driving handpiece 159 includes a slider switch 160, a guidewire exit port 161, and a pull wire actuator switch 165 having an actuator switch button or slider 166. In use, the operator can actuate the switch 165 so as to control the motor driving handpiece 159. Such actuation can cause the expandable abrading device 167 to rotate, translate, and/or expand/contract in an oscillatory or vibrational manner, as described elsewhere herein. In some cases, actuation of the button or slider 166 can adjust the frequency, amplitude, and/or direction in which the expandable abrading device 167 oscillates, vibrates, or moves.

The strands 176 of the abrading device 167 may be constructed of or include any of a variety materials, including without limitation metallic wire (such as stainless steel, titanium, nitinol, or other nickel based alloys), monofilament or multifilament fibers, braids, polymer or ceramic or glass fiber (such as Kevlar®, carbon fiber, nylon, polyurethane, polypropylene or other durable material), or organic materials such as carbon fiber, ceramic, plastic, glass or a combination of these materials. In some cases, catheter shaft 158 (e.g. FIGS. 10, 11) may be referred to as an elongate member. In some cases, the strands 176 and/or abrasive media 125 can be referred to as an abrasion feature.

Figure 12:
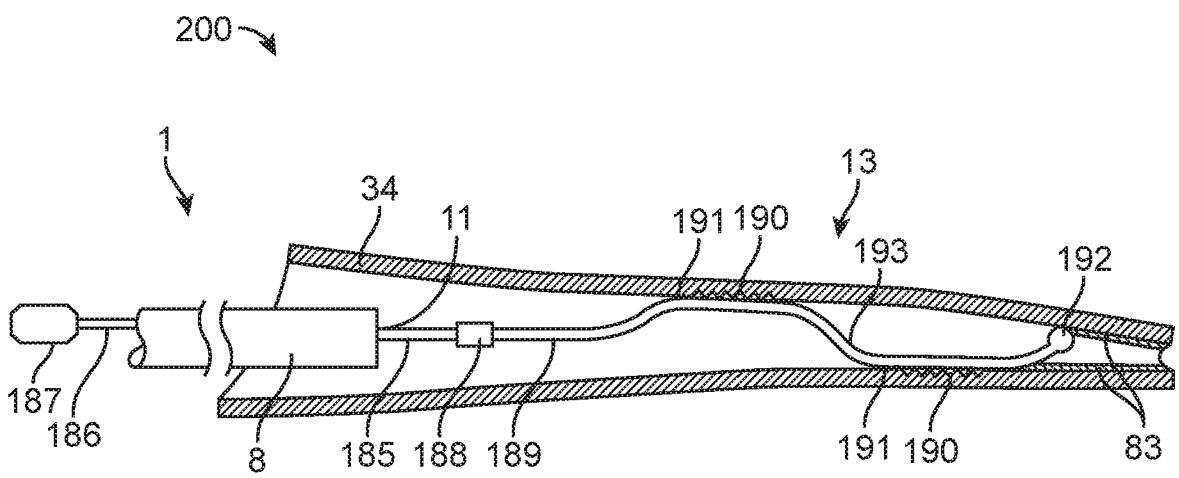
FIG. 12 illustrates a side view of a pulmonary treatment device with an abrasive spring element.
Figure 13:
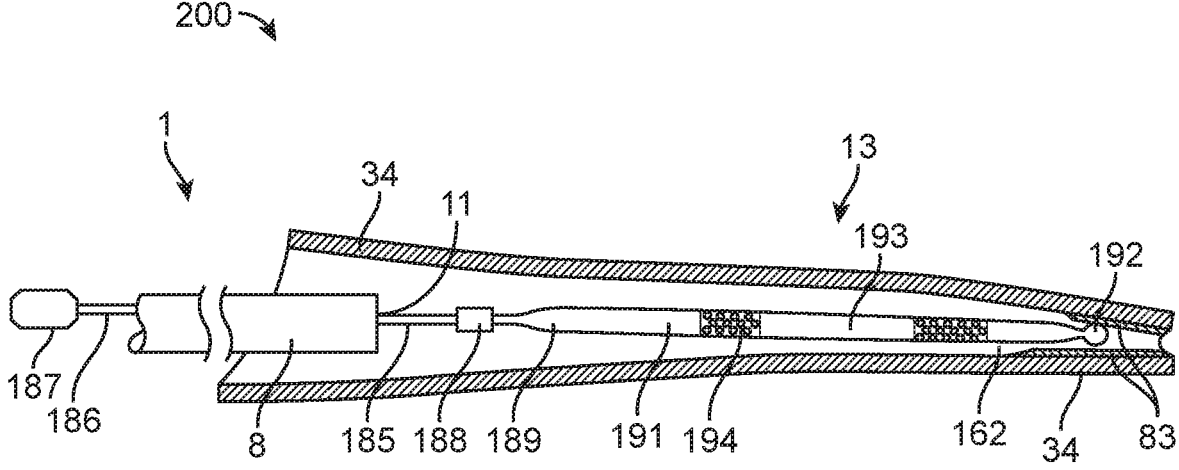
FIG. 13 illustrates a top view of a pulmonary treatment device with an abrasive spring element.

FIG. 12 illustrates aspects of a system 200 for treating a patient. System 200 includes a bronchoscope 1 having a flexible trunk 8 with a working channel exit port 11. As shown here, treatment device 13 can be inserted through a flexible trunk 8 of a bronchoscope 1, and advanced until it exits out a channel exit port 11 of a distal scope tip of the scope 1. The treatment device 13 includes, as shown here in a proximal to distal direction, a motion drive hub 187, a proximal abrader body 186, a distal abrader body 185, a crimp hub 188, a ribbon 189, a flat bearing surface 191, raised abrasive edges 190 (provided by an abrasive media 194 as depicted in FIG. 13), a transition 193, a flat bearing surface 191, raised abrasive edges 190, and a distal support 192. In use, the raised abrasive edges 190 can operate to contact and abrade the airway wall epithelium layer 83. In this way, the airway lumen wall (depicted here as airway wall cross section 34) can be stripped of the epithelium layer 83. The distal support 192 may have a variety of shapes including a coil, ball, end loop, cone shape, cylinder shape, or other blunt or atraumatic end shape that will minimize tissue agitation during the treatment process. According to some embodiments, the treatment device 13 can be configured to expand within the patient airway. For example, the treatment device 13 may be equipped with a pull wire coupled with the distal support 192. As another example, treatment device 13 may be biased in a spring-like fashion, so as to expand outwardly in diameter and press against the airway walls. Motion drive hub 187 can be coupled with a motor coupler as described elsewhere herein. In some cases, treatment device 13 is provided as a disposable device. In some cases, distal abrader body 185 may be referred to as an elongate member. In some cases, the raised abrasive edges 190 can be referred to as an abrasion feature.

FIG. 13 provides a plan view (e.g. top or bottom side) corresponding to the elevation view (e.g. right or left side) of FIG. 12. As shown in FIG. 13, system 200 includes a bronchoscope 1 having a flexible trunk 8 with a working channel exit port 11. As shown here, treatment device 13 can be inserted through a flexible trunk 8 of a bronchoscope 1, and advanced until it exits out a channel exit port 11 of a distal scope tip of the scope 1. The treatment device 13 includes, as shown here in a proximal to distal direction, a motion drive hub 187, a proximal abrader body 186, a distal abrader body 185, a crimp hub 188, a ribbon 189, a flat bearing surface 191, an abrasive media 194 (which provides raised abrasive edges 190 as depicted in FIG. 12), a transition 193, and a distal support 192. In use, the treatment device 13 can be advanced into an airway lumen 162, and the abrasive media 194 can operate to contact and abrade the airway wall epithelium layer 83. In this way, the airway lumen wall (depicted here as airway wall cross section 34) can be stripped of the epithelium layer 83. In some cases, distal abrader body 185 may be referred to as an elongate member. In some cases, the abrasive media 194 can be referred to as an abrasion feature.

FIG. 14 depicts aspects of a system 300 for treating a patient. System 300 includes a treatment device 13 having an abrader element shaft 225, and a vacuum hub 226 coupled with a hollow catheter 238. The distal end 239 of the catheter 238 can be inserted into a proximal airway lumen 76, and the abrader element shaft 225 can extend through the catheter 238 and into the proximal airway lumen 76. A proximal end 240 of the catheter 238 is coupled with the vacuum hub 226 via a joint 237. A proximal end 235 of the abrader element shaft 225 is coupled with a motion drive hub 187, the motion drive hub 187 is coupled with a motor coupler 195, and the motor coupler 195 is coupled with a motion driving handpiece 159. As shown here, the motion driving handpiece 159 includes a slider switch 160. The motion driving handpiece 159 is coupled with a battery 134 via a power cable 133 (or multiple power cables 133 coupled via one or more connectors 150). The battery 134 operates to energize the motion driving handpiece 159. A wall outlet plug 136 can be coupled with the battery 134 via one or more electrical cables 135. In some cases, electrical cables 135 can include or be joined by connectors 150. In some cases, battery 134 is a rechargeable battery. In some cases, system 300 may include an AC/DC converter in place of the battery 134. When the wall outlet plug 136 is plugged into a wall outlet, electricity from the wall outlet can be used to recharge the battery 134 or to directly operate the motion driving handpiece 159. In some cases, a handpiece 159 is graspable by a user so as to manually applying a linear and/or rotational force.

Vacuum hub 226 further includes a seal 227. As shown here, the abrader element shaft 225 extends through the seal 227 and a bearing 234. The abrader element shaft 225 can be coupled to or fixed with the bearing 234. Hence, in operation, the abrader element shaft 225 and the bearing 234 can be introduced into the vacuum hub, for example until the bearing 234 contacts or approaches the proximal end of the catheter 238, and the seal 227 can be placed over the abrader element shaft 225 and coupled with a distal portion of the vacuum hub 226. System 300 also includes a filter 230 that is coupled with the vacuum hub 226 via a hose 229 and a Luer hub 228. As shown here, Luer hub 228 can be coupled with a Luer tapered connection 241 of the vacuum hub 226. The filter 230 can be connected with a vacuum source 233 via the hose 229 and a coupler 232. The filter 230 can contain collected material 231. In some cases, the vacuum source 233 may be operated by a physician or operator using a foot pedal.

In use, a distal end 236 of the abrader element shaft 225 is placed in a distal airway lumen 77, and suction is applied through the vacuum hub 226 so as to constrict a section of the airway distal to the distal end 239 of the catheter 238, thereby drawing the epithelium 83 against the raised edges 125 of the abrasive grit or media 82. The raised abrasive edges 125 can operate to contact and abrade the airway wall epithelium layer 83. In this way, the airway lumen wall (depicted here as airway wall cross section 34) can be stripped of the epithelium layer 83, which leaves the exposed basement membrane 85. The operator can control the motor driving handpiece 159 so as to cause the abrader element shaft 225 to rotate and/or translate in an oscillatory or vibrational manner, as described elsewhere herein. In some cases, actuation of the button or slider 166 can adjust the frequency, amplitude, and/or direction in which the abrader element shaft 225 oscillates, vibrates, or moves. In some cases, simply pulling the catheter 238 in the proximal direction may be sufficient to abrade the airway surface as desired, without oscillating the abrader element shaft 225. Suction from the vacuum source 233 draws the abraded epithelium through the hollow catheter 238, through the vacuum hub 226, through the hose 229, and into the filter or filter trap 230 where it resides as collected material 231. In some cases, the vacuum source 233 may be operated by a physician or operator using a foot pedal. As discussed elsewhere herein (e.g. with regard to FIGS. 27 and 28), in some cases a system 300 may include a foam mechanism instead or in addition to the abrasive edges 125 and/or abrasive grit 82. In some cases, abrader element shaft 225 may be referred to as an elongate member. In some cases, the raised abrasive edges 125 can be referred to as an abrasion feature.

FIG. 15 depicts aspects of a system 300 for treating a patient. System 300 includes a treatment device 13 having an abrasive catheter 250 and a motion driving handpiece 159, a vacuum hub 226, and a filter 230. The abrasive catheter 250 includes a distal end 251, a distal port 258, raised abrasive edges 125, a proximal port 257, a distal bearing 255, a hub port 259, a proximal bearing 254, a motion drive shaft 253, a proximal end 252, and a motion drive hub 187. The distal bearing 255 and proximal bearing 254 can operate to keep the treatment device 13 from detaching from the vacuum hub 226. The motion drive hub 187 is coupled with a motor coupler 195, and the motor coupler 195 is coupled with a motion driving handpiece 159. As shown here, the motion driving handpiece 159 includes a slider switch 160. The motion driving handpiece 159 is coupled with a battery 134 via a power cable 133 (or multiple power cables 133 coupled via one or more connectors 150). The battery 134 operates to energize the motion driving handpiece 159. A wall outlet plug 136 can be coupled with the battery 134 via one or more electrical cables 135. In some cases, electrical cables 135 can include or be joined by connectors 150. In some cases, battery 134 is a rechargeable battery. In some cases, system 300 may include an AC/DC converter in place of the battery 134. When the wall outlet plug 136 is plugged into a wall outlet, electricity from the wall outlet can be used to recharge the battery 134 or to directly operate the motion driving handpiece 159. In some cases, a handpiece 159 is graspable by a user so as to manually applying a linear and/or rotational force.

Vacuum hub 226 further includes seals 256 (e.g. O-rings). As shown here, the abrader element shaft 225 extends through the seals 256. The filter 230 is coupled with the vacuum hub 226 via a hose 229 and a Luer hub 228. The filter 230 can be connected with a vacuum source 233 via the hose 229 and a coupler 232. The filter 230 can contain collected material 231. In some cases, the vacuum source 233 may be operated by a physician or operator using a foot pedal. As the abrasive catheter 250 is pulled in a proximal direction, or otherwise during operation of the treatment device 13, abraded debris can be removed and aspirated from the patient airway, and vacuumed into the filter 230.

In use, the distal end 251 of the abrasive catheter 250 is placed in a distal airway lumen 77, and suction is applied through the vacuum hub 226 so as to constrict a section of the airway toward the abrasive catheter 250 between the proximal port 257 and the distal port 258, thereby drawing the epithelium 83 against the raised edges 125 of the abrasive catheter 250. The raised abrasive edges 125 can operate to contact and abrade the airway wall epithelium layer 83. In this way, the airway lumen wall (depicted here as airway wall cross section 34) can be stripped of the epithelium layer 83, which leaves the exposed basement membrane 85. The operator can control the motor driving handpiece 159 so as to cause the catheter 250 to rotate and/or translate in an oscillatory or vibrational manner, as described elsewhere herein. In some cases, actuation of the button or slider 166 can adjust the frequency, amplitude, and/or direction in which the catheter 250 oscillates, vibrates, or moves. In some cases, simply pulling the catheter 250 in the proximal direction may be sufficient to abrade the airway surface as desired, without oscillating the catheter 250. Suction from the vacuum source 233 draws the abraded epithelium through the abrasive catheter 250, through the hub port 159, through the hose 229, and into the filter or filter trap 230 where it resides as collected material 231. In some cases, raised abrasive edges 125 can include abrasive edges provided by cutting or etching shapes or patterns in the catheter 250. For example, such abrasive shapes or patterns for the abrasive edges can be created by cutting or arc welding the catheter 250. In some cases, the patterning or etching can cause craters on the catheter 250 which are sharp. By spacing the distal port 258 and the proximal port 257 apart from each other, the force with which the raised abrasive edges 125 bears against and abrades the epithelium layer 83. By spacing the ports farther apart, the pressure is reduced. Closer spacing of the ports increases the pressure and abrasive action. According to some embodiments, the ports can be spaced at least 0.01 mm and up to 50 mm apart from each other, and in exemplary embodiments they can be spaced between 1 mm and 35 mm apart. The catheter may contain from one to 3000 ports. The ports may be 0.010 mm diameter up to 6 mm in diameter. In some cases, catheter 250 may be referred to as an elongate member. In some cases, the raised abrasive edges 125 can be referred to as an abrasion feature.

Figure 16:
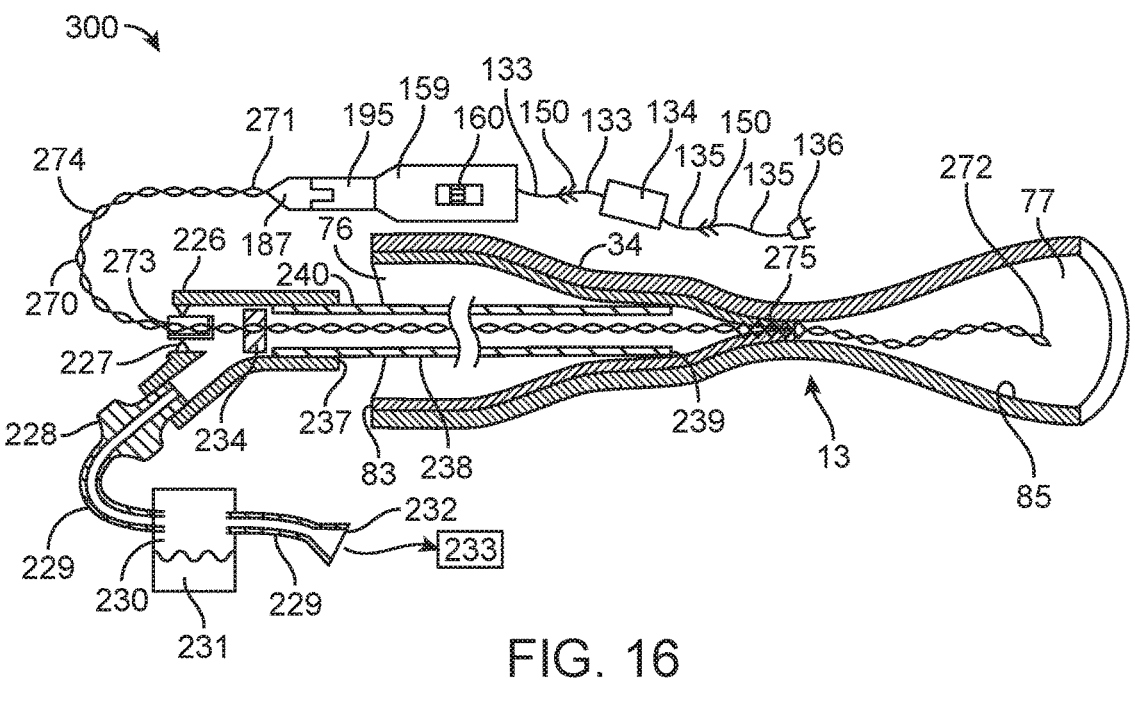
FIG. 16 illustrates a pulmonary treatment system with an abrasive brush and suction catheter.

FIG. 16 depicts aspects of a system 300 for treating a patient. System 300 includes a treatment device 13 having an abrasive brush 270 and a motion driving handpiece 159, a vacuum hub 226 coupled with a hollow catheter 238, and a filter 230. The abrasive brush 270 includes a distal end 272, an abrasive bristle 275, a proximal end 271, and a motion drive hub 187. As shown here, the abrasive brush 270 can include a wire with a twist 274 in the brush wire. The motion drive hub 187 is coupled with a motor coupler 195, and the motor coupler 195 is coupled with a motion driving handpiece 159. As shown here, the motion driving handpiece 159 includes a slider switch 160. The motion driving handpiece 159 is coupled with a battery 134 via a power cable 133 (or multiple power cables 133 coupled via one or more connectors 150). The battery 134 operates to energize the motion driving handpiece 159. A wall outlet plug 136 can be coupled with the battery 134 via one or more electrical cables 135. In some cases, electrical cables 135 can include or be joined by connectors 150. In some cases, battery 134 is a rechargeable battery. In some cases, system 300 may include an AC/DC converter in place of the battery 134. When the wall outlet plug 136 is plugged into a wall outlet, electricity from the wall outlet can be used to recharge the battery 134 or to directly operate the motion driving handpiece 159. In some cases, a handpiece 159 is graspable by a user so as to manually applying a linear and/or rotational force.

Vacuum hub 226 further includes a seal 227, a seal bearing 273, and a bearing 234. A distal end 239 of the catheter 238 can be inserted into a proximal airway lumen 76, and the abrasive brush 270 can extend through the catheter 238 and into the proximal airway lumen 76. A proximal end 240 of the catheter 238 is coupled with the vacuum hub 226 via a joint 237. As shown here, the abrasive brush 270 extends through the seal bearing 273 and the bearing 234. The filter 230 is coupled with the vacuum hub 226 via a hose 229 and a Luer hub 228. The filter 230 can be connected with a vacuum source 233 via the hose 229 and a coupler 232. The filter 230 can contain collected material 231. In some cases, the vacuum source 233 may be operated by a physician or operator using a foot pedal.

In use, the distal end 272 of the abrasive brush 270 is placed in a distal airway lumen 77, and suction is applied through the vacuum hub 226 so as to constrict a section of the airway distal to the distal end 239 of the catheter 238, thereby drawing the epithelium 83 against the abrasive bristle 275. The abrasive bristle 275 can operate to contact and abrade the airway wall epithelium layer 83. In this way, the airway lumen wall (depicted here as airway wall cross section 34) can be stripped of the epithelium layer 83, which leaves the exposed basement membrane 85. Suction from the vacuum source 233 draws the abraded epithelium through the hollow catheter 238, through the vacuum hub 226, through the hose 229, and into the filter or filter trap 230 where it resides as collected material 231. In some cases, the vacuum source 233 may be operated by a physician or operator using a foot pedal. In some cases, abrasive brush 270 may be referred to as an elongate member. In some cases, the abrasive bristle 275 can be referred to as an abrasion feature.

Figure 17:
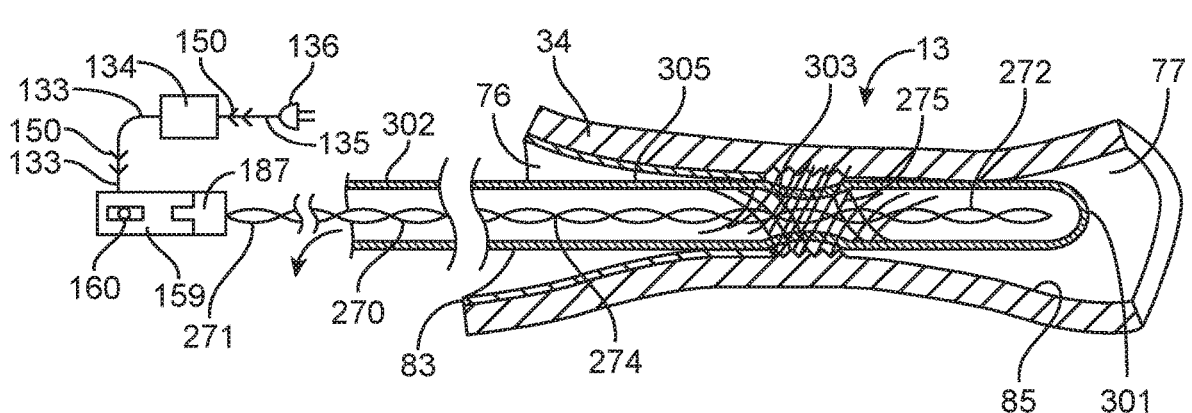
FIG. 17 illustrates a pulmonary treatment system with an abrasive brush and brush guide catheter.

FIG. 17 depicts aspects of a system 300 for treating a patient. System 300 includes a treatment device 13 having an abrasive brush 270 and a motion driving handpiece 159, and a brush guide catheter 305. In some embodiments, system 300 may also include a vacuum hub, a filter, and other related elements, for example as depicted in FIG. 15. The brush guide catheter 305 includes a distal end 301, a port 303, and a proximal end 302. The abrasive brush 270 includes a distal end 272, an abrasive bristle 275, a proximal end 271, and a motion drive hub 187. As shown here, the abrasive brush 270 can include a wire with a twist 274 in the brush wire. The motion drive hub 187 is coupled with a motor coupler 195, and the motor coupler 195 is coupled with a motion driving handpiece 159. As shown here, the motion driving handpiece 159 includes a slider switch 160. The motion driving handpiece 159 is coupled with a battery 134 via a power cable 133 (or multiple power cables 133 coupled via one or more connectors 150). The battery 134 operates to energize the motion driving handpiece 159. A wall outlet plug 136 can be coupled with the battery 134 via one or more electrical cables 135. In some cases, electrical cables 135 can include or be joined by connectors 150. In some cases, battery 134 is a rechargeable battery. In some cases, system 300 may include an AC/DC converter in place of the battery 134. When the wall outlet plug 136 is plugged into a wall outlet, electricity from the wall outlet can be used to recharge the battery 134 or to directly operate the motion driving handpiece 159. In some cases, a handpiece 159 is graspable by a user so as to manually applying a linear and/or rotational force. In some cases, the treatment device 13 is configured so that the strands of the abrasive bristle 275 extend radially beyond the outer circumference defined by the catheter 305. In some cases, the treatment device 13 is configured so that the strands of the abrasive bristle 275 do not extend radially beyond the outer circumference defined by the catheter 305.

In use, the distal end 301 of the brush guide catheter 305 is placed in a distal airway lumen 77. The abrasive bristle 275 can operate to contact and abrade the airway wall epithelium layer 83. In this way, the airway lumen wall (depicted here as airway wall cross section 34) can be stripped of the epithelium layer 83, which leaves the exposed basement membrane 85. Suction from a vacuum source can draw the abraded epithelium through the brush guide catheter 305, and through a vacuum hub, a hose, and into a filter or filter trap where it resides as collected material, for example as depicted in FIG. 15. As discussed elsewhere herein (e.g. with regard to FIGS. 27 and 28), in some cases a system 300 may include a foam mechanism instead or in addition to the abrasive bristle 275. In some cases, abrasive brush 270 may be referred to as an elongate member. In some cases, the abrasive bristle 275 can be referred to as an abrasion feature.

Figure 18:
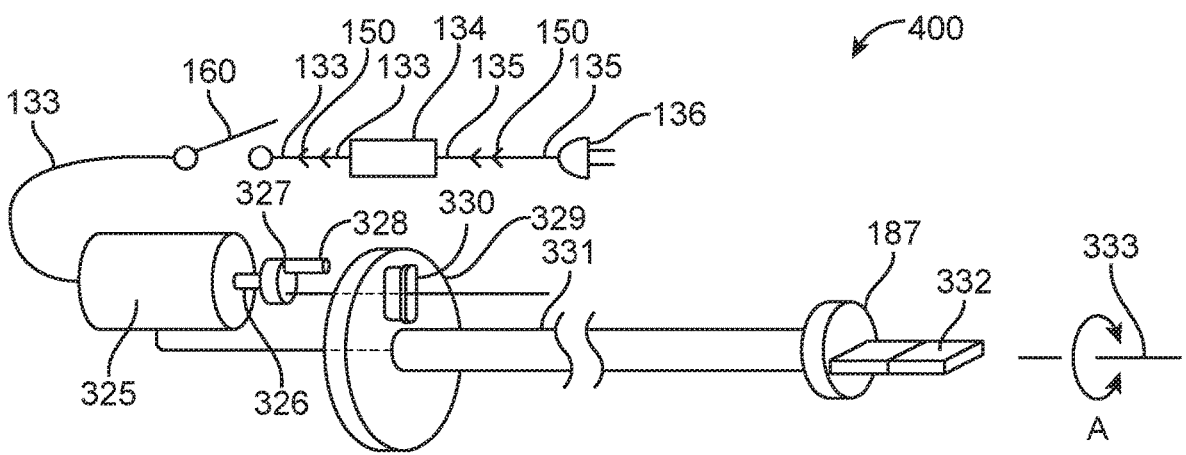
FIGS. 18 and 18A illustrate aspects of a motor drive assembly to produce oscillatory rotation.
Figure 19:
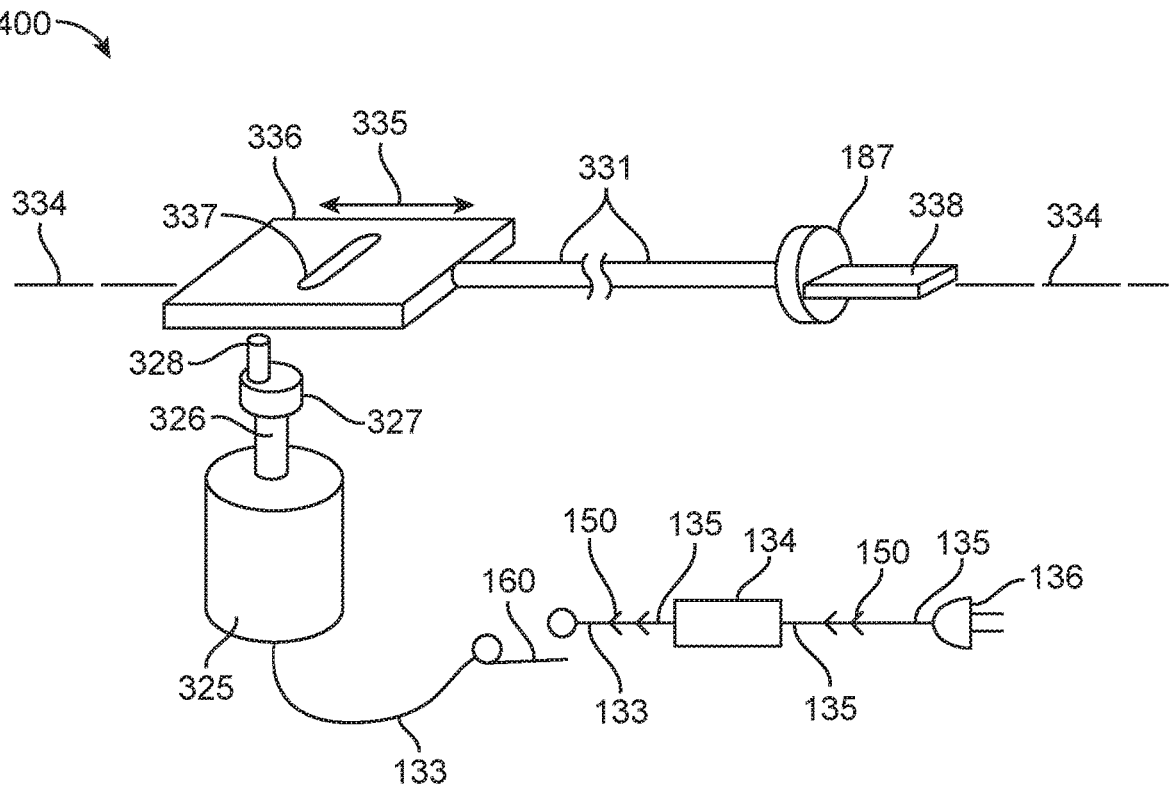
FIG. 19 illustrates a motor drive assembly to produce oscillatory linear motion.

Any of the embodiments depicted in FIGS. 1 and 6-17 can incorporate any of the oscillatory control mechanism features illustrated in FIGS. 18-19. In some embodiments, a control mechanism or oscillatory control mechanism can include any one or more features disclosed herein pertaining to a motor assembly or a handpiece (e.g. motion driving handpiece).

FIG. 18 depicts aspects of a system 400 for treating a patient. System 400 includes a motor 325, a motor drive shaft 326, an eccentric drive hub 327 (e.g. a rotating disk), an eccentric drive pin 328, a rotary oscillation hub 329, a rotary drive slot 330, an output shaft 331, a motion drive hub 187, and a rotary oscillation coupler key 332. As shown here, system 400 further includes a power cable 133 disposed between the motor 325 and a slider switch 160. What is more, system 400 includes a battery 134 coupled with the slider switch 160. In some cases, the slider switch 160 is coupled with the battery 134 via a power cable 133 (or multiple power cables 133 coupled via one or more connectors 150). The battery 134 operates to energize the motor 325. A wall outlet plug 136 can be coupled with the battery 134 via one or more electrical cables 135. In some cases, electrical cables 135 can include or be joined by connectors 150. In some cases, battery 134 is a rechargeable battery. In some cases, system 300 may include an AC/DC converter in place of the battery 134. When the wall outlet plug 136 is plugged into a wall outlet, electricity from the wall outlet can be used to recharge the battery 134 or to directly operate the motor 325. As shown here, operation of the motor 325 can cause the rotary oscillation coupler key 332 to rotate in an oscillatory manner about rotation axis 333, as depicted by arrow A.

Figure 18A:
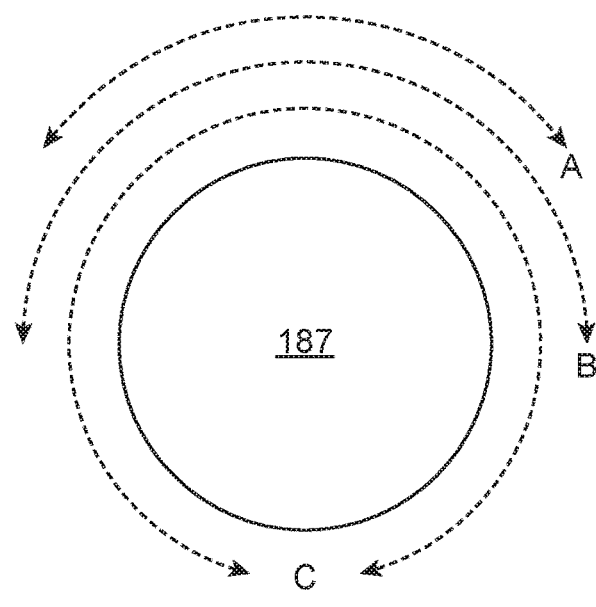

FIG. 18A illustrates exemplary aspects of oscillatory motion that can be achieved by motion drive hub 187. As depicted by arrow A, the motion drive hub 187 can rotationally oscillate throughout a range of motion of about 60 degrees. Similarly, as depicted by arrow B, the motion drive hub 187 can rotationally oscillate throughout a range of motion of about 180 degrees. Likewise, as depicted by arrow C, the motion drive hub 187 can rotationally oscillate throughout a range of motion of about 350 degrees. A treatment system can be configured to provide any value or range of values for the rotational oscillation. In some cases, the drive hub 187 (or abrasive balloon or device) may oscillate throughout a rotation range of 5 degrees. In some cases, the drive hub 187 (or abrasive balloon or device) may oscillate throughout a rotation range of 10 degrees. In some cases, the drive hub 187 (or abrasive balloon or device) may oscillate throughout a rotation range having a value between 0 degrees and 360 degrees. Advantageously, such oscillatory motions allow the abrasive treatment devices to abrade a controlled portion of the airway wall, ranging from a small area (e.g. corresponding to a 1 degree range of oscillatory motion) to an entire inner circumference of the airway wall (e.g. corresponding to a 360 degree range of oscillatory motion) without having to manually rotate the treatment device itself.

FIG. 19 depicts aspects of a system 400 for treating a patient. System 400 includes a motor 325, a motor drive shaft 326, an eccentric drive hub 327, an eccentric drive pin 328, an oscillation drive slide 336, a linear drive slot 337, an output shaft 331, a motion drive hub 187, and a linear oscillation coupler key 338. As shown here, system 400 further includes a power cable 133 disposed between the motor 325 and a slider switch 160. What is more, system 400 includes a battery 134 coupled with the slider switch 160. In some cases, the slider switch 160 is coupled with the battery 134 via a power cable 133 (or multiple power cables 133 coupled via one or more connectors 150). The battery 134 operates to energize the motor 325. A wall outlet plug 136 can be coupled with the battery 134 via one or more electrical cables 135. In some cases, electrical cables 135 can include or be joined by connectors 150. In some cases, battery 134 is a rechargeable battery. In some cases, system 300 may include an AC/DC converter in place of the battery 134. When the wall outlet plug 136 is plugged into a wall outlet, electricity from the wall outlet can be used to recharge the battery 134 or to directly operate the motor 325. As shown here, operation of the motor 325 can cause the linear oscillation coupler key 338 to translate linearly in an oscillatory manner along an axis of translation 334, as depicted by the direction of motion arrow 335.

Accordingly, when considering FIGS. 18 and 19 either alone or in combination, it can be seen that any of a variety of oscillatory motions can be achieved. In some cases, elements of FIG. 18 can be employed to achieve a rotational oscillatory motion. In some cases, elements of FIG. 19 can be employed to achieve a linear translational oscillatory motion. In some case, elements of FIGS. 18 and 19 can be employed in combination to achieve both a rotational oscillatory motion and a linear translational oscillatory motion. In some cases, any of these three options can be combined with pulling and/or pushing of the treatment device along a central longitudinal axis of the airway. A combination device may include components shown in FIG. 18 combined with components shown in FIG. 19, for example a rotary drive motor (e.g. motor 325 of FIG. 18) could be placed upon a linear drive slide (e.g. drive slide 336 of FIG. 19). In this way, the rotary drive motor (and the distal components connected thereto) could be oscillated in a linear fashion.

It may be appreciated that FIGS. 6-19 may not be drawn to scale; rather, the distal and proximal ends of the delivery and/or treatment devices or other system elements may be prominent for focus and detail. It may be appreciated that, for example, a catheter and/or treatment device may be much longer than depicted to allow for advancement through the trachea to various airways, including advancement along airways past the 4th generation. Likewise, it may be appreciated that the airway may be illustrated as bisected for the purpose of clear viewing of the device and delivery devices disposed therein.

Figure 20:
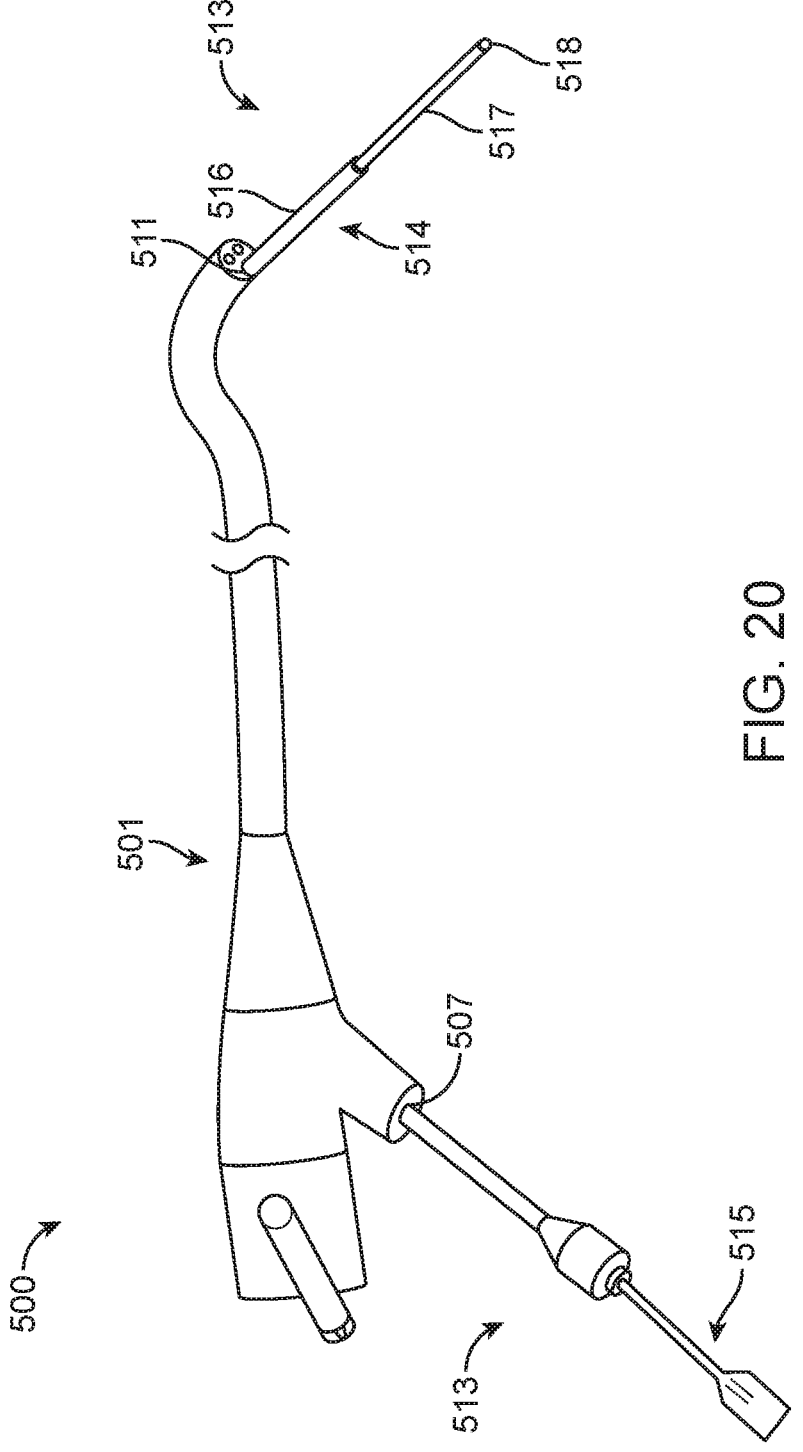
FIG. 20 illustrates a bronchoscope and pulmonary treatment device.

FIG. 20 depicts aspects of a system 500 for treating a patient. System 500 includes a pulmonary treatment device 513 and a delivery device 501 such as a bronchoscope. The pulmonary treatment device 513 can be sized and configured to be delivered by the delivery device 501. The delivery device 501 can be configured to be inserted into the lung. In some embodiments, the pulmonary treatment device 513 is configured to be delivered through a lumen in the delivery device, such as by pushing the treatment device through a lumen of a scope, catheter, introducer, sheath, sleeve or similar device. In some cases, the treatment device 513 can be loaded into a port 507 and the delivery device 501 can be advanced through the tracheobronchial tree to a target location within the lung. In some cases, the device 513 is loaded within the bronchoscope port 507 so that the distal end 514 of the device 513 is directed distally through the channel exit port 511 and the proximal end 515 of the device 513 extends proximally through the bronchoscope port 507.

As shown here, the treatment device 513 can include a catheter 516, and a guidewire or dilator 517 can be introduced, so that the guidewire or dilator 517 operates to lead the catheter 516. This configuration can help to prevent the catheter 516 from gouging the airway wall or lung tissue when the catheter 516 is advanced within the airway lumen. Deployment of the guidewire or dilator 517 can also help to steer the catheter 516 to the desired anatomical location, for example into a particular branch, airway branch, airway lumen, or the like. In some cases, a distal tip 518 of the guidewire or dilator 517 can have a curved portion. In some cases, the curved portion can be torqued and steered into a branch to allow the catheter 516 to be advanced into the branch. In some cases, a rounded end of a distal tip 518 can help to guide a larger tube, such as the catheter 516. In some cases, the distal tip 518 of the guidewire or dilator 517 can include a radiopaque material. In some cases, a distal tip of the catheter can include a radiopaque material.

Figure 21:
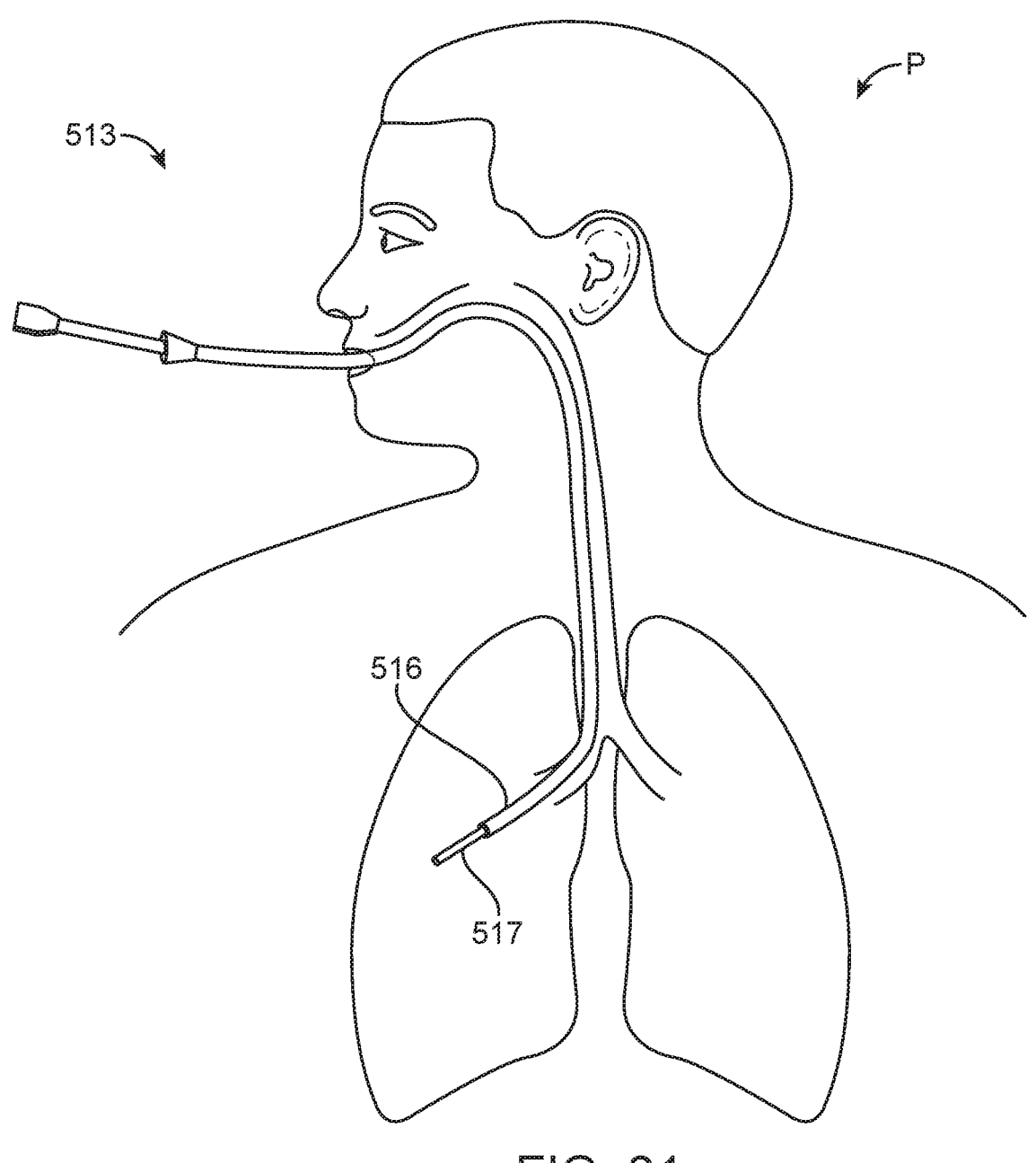
FIG. 21 illustrates a treatment device for treating a patient without the use of a bronchoscope.

In some cases, the treatment device 513 can be introduced into a patient P without the use of a bronchoscope, as illustrated in FIG. 21. In some cases, the catheter 516 can be introduced into the patient P using a guidewire or dilator 517. In some cases, the catheter 516 can be introduced into the patient P without using a guidewire or dilator. Any of the treatment devices disclosed herein, for example including treatment device 513, can be delivered through a bronchoscope, or only using the lumen of a trachea tube (e.g. such as a trachea tube which is typically used to ventilate a patient, or to gain access within a patient airway past the vocal cords), or only guided over a guidewire, or without guidance by any tube or wire. In some cases, a rounded end of a distal tip of the guidewire or dilator 517 can help to guide a larger tube, such as the catheter 516.

Figure 22:
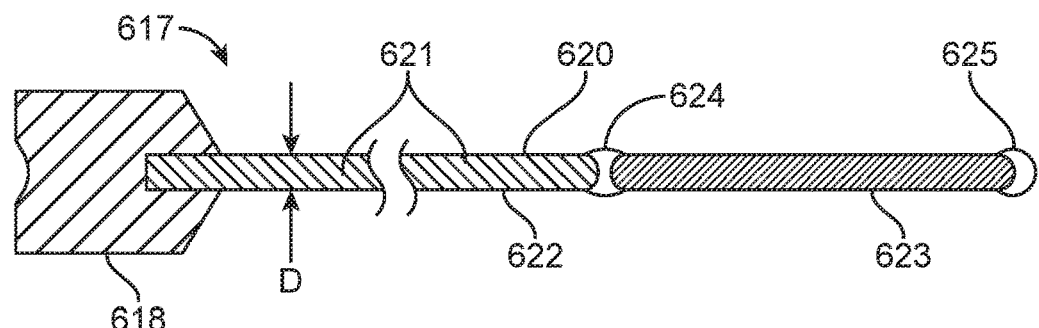
FIG. 22 illustrates a guidewire having multiple wire configurations.

FIG. 22 depicts aspects of an exemplary guidewire 617, according to embodiments of the present invention. In some cases, guidewire 617 includes twisted cable wire, a braided wire, counter rotated twisted wire, or any combination thereof. In some cases, the wire 620 can have a diameter D with a value within a range from about 1 mm to about 10 mm. In some cases, the wire 620 is constructed so that gaps do not open up between individual strands 621 of the wire 620 when the wire is bent (e.g. around corners or other obstructions or anatomical features) which may occur when the wire 620 is advanced or retracted within the patient's airways. In this way, there are no gaps that can catch tissue when the wire 620 is pulled back and straightened out, which may otherwise occur during the course of a treatment procedure. If gaps were to develop between individual wire strands 621, then such could close, catching tissue and locking the wire 620 in the patient, or causing tissue to be torn out upon removal of the guidewire 617. In the continuous wire embodiment illustrated in FIG. 22, the wire 620 doesn't open up upon bending. Such gaps can be a drawback associated with some small core wire guidewires. In some cases, the wire 620 can have a diameter D with a value of about 1.5 mm. In some cases, the wire 620 is comprised of multiple individual wire strands or wire cables 621. Such multi-strand or multi-cable wire construction can provide a wire that is very flexible and smooth. In some cases, the wire 620 can have about 375 individual wire strands or cables 621. In some cases, a wire 620 or portion thereof having fewer strands or cables 621 can confer a greater degree of pushability. For example, a proximal portion 622 of the wire 620 can have a number of cables or strands with a value within a range from about 4 to about 50 wires or strands. In some cases, a wire 620 or portion thereof having more strands or cables 621 can confer a greater degree of flexibility. For example, a distal portion 623 of the wire 620 can have a number of cables or strands with a value within a range from about 50 to about 1000 wires or strands. Hence, the guidewire 617 depicted in FIG. 22 is a hybrid design that includes two different sections having two different pushability/flexibility profiles. Guidewire 617 includes a proximal hub 618, a pushable proximal section 622, a flexible distal section 623, a connection 624 between the proximal section 622 and distal section 623, and a distal termination 625. In some cases, the connection 624 is a welded connection. In some cases, the distal termination 625 is a distal welded termination. In some cases, the distal termination 625 can be cast into a shape during welding. In some cases, the distal termination 625 can have a ball shape. In some cases, the ball shape can have a diameter with a value of about 2 mm. In some cases, the ball shape can have a diameter with a value within a range from about 1 mm to about 10 mm. The wire 620 can operate to transmit torque without wind up, which may be a drawback associated with some small core wire guidewires. In some cases, the wire 620 can be torqued from the hub 618. In some cases, the wire 620 can be torqued from any portion along the shaft of the wire 620. This is in contrast to small core wire guidewires, which need to be torqued from a hub because the outer coil floats over the core. Advantageously, the wire 620 can be torqued as desired, without having to reach back to the proximal end every time the user wishes to apply torque to the wire. In some cases, a rounded end of a distal termination 625 can help to guide a larger tube, such as a catheter. In some cases, the distal termination 625 can include a radiopaque material.

Figure 23:
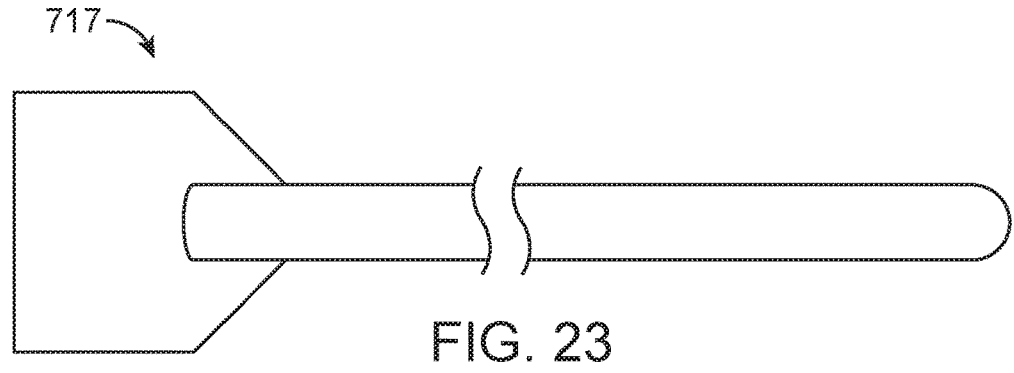
FIG. 23 illustrates a dilator.
Figure 24:
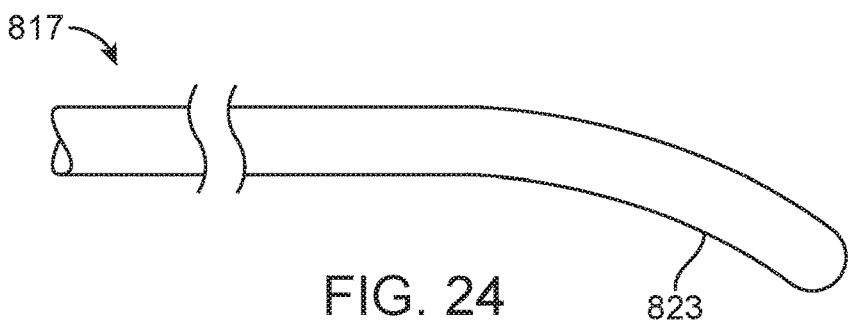
FIG. 24 illustrates a dilator with a curved distal end.
Figure 25:
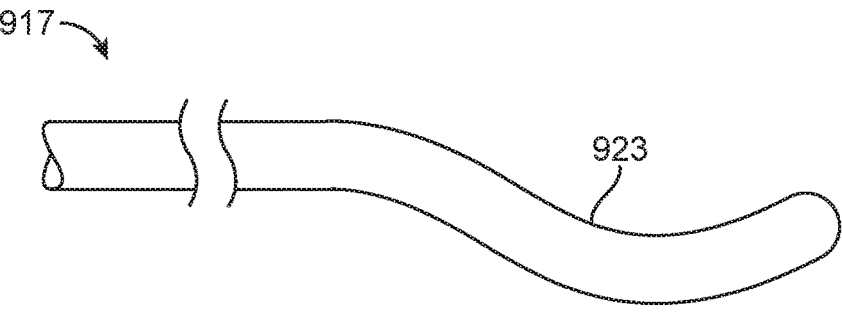
FIG. 25 illustrates a dilator with a multi-curved distal end.

FIG. 23 depicts aspects of an exemplary dilator 717, according to embodiments of the present invention. In some embodiments, dilator 717 is provided as a solid plastic dilator. In some cases, a rounded end of a distal tip of the dilator 717 can help to guide a larger tube, such as a catheter. FIG. 24 depicts aspects of an exemplary dilator 817 according to embodiments of the present invention. As shown here, dilator 817 can have a distal section 823 having a curve shape. In some cases, a rounded end of a distal tip of the dilator 817 can help to guide a larger tube, such as a catheter. FIG. 25 depicts aspects of an exemplary dilator 917 according to embodiments of the present invention. As shown here, dilator 917 can have a distal section 923 having a two direction curve in the same plane. In some cases, a rounded end of a distal tip of the dilator 917 can help to guide a larger tube, such as a catheter.

Figure 26:
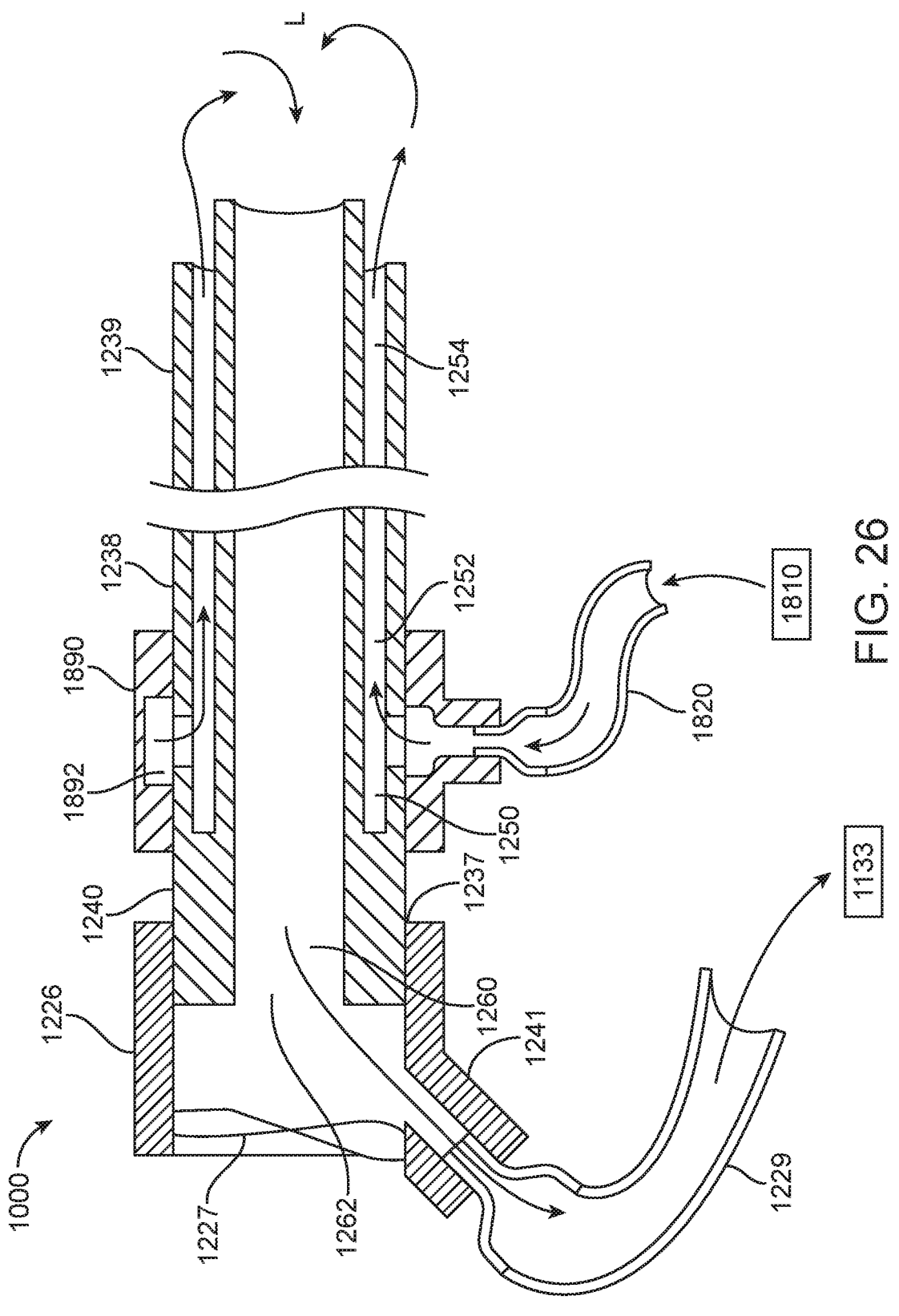
FIG. 26 illustrates aspects of a pulmonary treatment system with a multi-lumen catheter.

FIG. 26 depicts aspects of a system 1000 for treating a patient. System 1000 includes a treatment device (not shown) and a vacuum hub 1226 coupled with a catheter 1238. The treatment device can include one or more features of any of the treatment devices disclosed herein, for example the treatment devices shown in FIGS. 6-14, 16, 17, 27, and 28. A distal end 1239 of the catheter 1238 can be inserted into an airway lumen, and the treatment device can extend through the catheter 1238 and into the airway lumen. A proximal end 1240 of the catheter 1238 can be coupled with the vacuum hub 1226 via a joint 1237. System 1000 may also include a filter that is coupled with the vacuum hub 1226 via a hose 1229 and a vacuum source. Aspects of exemplary filters and/or vacuum sources that can be incorporated in system 1000 are depicted in FIGS. 14-16. In use, a treatment device can be placed within the catheter 1238, a wash fluid can be delivered from a wash fluid source 1810, through a wash fluid conduit 1820, through a port conduit 1892 of a wash fluid port 1890, into a proximal section 1252 of an outer lumen 1250 of the catheter 1238, and out of a distal section 1254 of the outer lumen, so that the wash fluid flows into the airway lumen L. Suction can be applied through the vacuum hub 1226, for example from vacuum source 1133 via hose 1229, so as to draw the wash fluid into an inner lumen 1260 of the catheter 1238. Suction from the vacuum source 1133 can also operate to draw abraded epithelium and/or other tissue or debris from the airway through the catheter inner lumen 1260, through the hose 1229, and into a filter or filter trap where it resides as collected material, as described elsewhere herein. In some cases, the vacuum source 1133 may be operated by a physician or operator using a foot pedal.

Hence, it is understood that embodiments of the present invention encompass double lumen or multiple lumen catheter configurations that allow for suction and fluid delivery. Such embodiments enable for the delivery of treatment or therapy devices into and through the inner lumen 1260 (e.g. via passage through seal 1227. In some cases, seal 1227 operates to close the back opening or proximal section 1262 of the inner lumen 1260 until the treatment device is introduced therethrough. In this way, wash fluid can be infused via the fluid delivery port 1890 and outer lumen 1250, and thereafter the wash fluid can be aspirated back out of the patient via operation of the inner lumen 1260, suction port 1241 of vacuum hub 1226, hose 1229, and vacuum source 1133. In some embodiments, the system 1000 can operate to infuse saline or other fluids to provide a wash fluid within the patient airway that is then aspirated back out of the patient, for example while drawing vacuum to pull the airway tissue or wall down to the catheter 1238 and/or vacuuming out debris from the airway lumen L.

According to some embodiments, systems such as system 2000 can be used to infuse the lung with fluid that can include antibiotic, antifungal or other agents to minimize infection relating to agitation of the airway walls and the predisposed mucus in the airway. Other agents such as steroid agents, wound healing agents, and the like, may also be introduced through the catheter 1238 (or secondary lumen 1250) to reduce or control the rate of inflammatory response to the scrubbing, abrading, or treatment of the airway wall. Infusing such fluid or saline while aspirating can also set up a flow path into and back out of the patient airway that can help move debris and other contaminants out of the airway to improve healing, airway wall remodeling and breathing. In some cases, the infused fluid can have a desired or predetermined temperature. For example, the fluid may be heated to a certain temperature prior to infusion, or cooled to a certain temperature prior to infusion.

Figure 27:
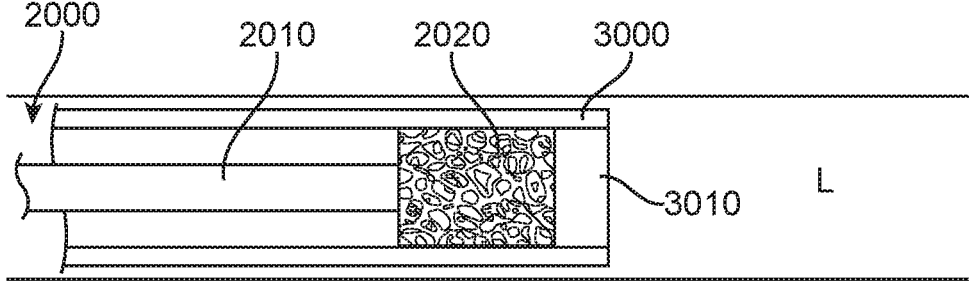
FIG. 27 illustrates a treatment device with an expandable foam scrubber.
Figure 28:
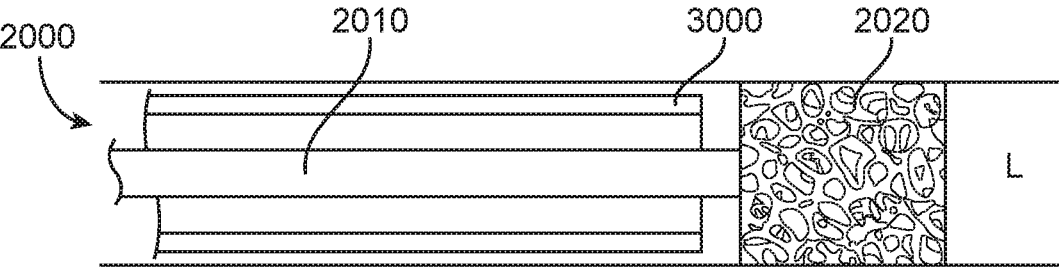
FIG. 28 illustrates a treatment device with an expanded foam scrubber.

FIGS. 27 and 28 depict aspects of a treatment device 2000 according to embodiments of the present invention. As shown here, treatment device 2000 includes an elongate element 2010 coupled with a distal section 2020. The treatment device 2000 can be delivered to a desired location within a patient, for example within an airway lumen L of the patient's lung, via a catheter 3000. In some embodiments, distal section 2020 includes or is comprised of a material that is expandable and compressible. For example, the distal section 2020 can include an expanding foam material. In exemplary embodiments, the distal section performs a scrubbing function. In some cases, the distal section performs a brushing function. In some cases, the distal section 2020 includes an expandable open cell foam or scrubbing material, which may resemble a plastic dish scrubbing material. In some cases, the distal section material is sufficiently hard to abrade the epithelium. In some cases, the distal section 2020 includes any of a variety of silicones, nylons, and/or other open cell plastics. As shown in FIG. 28, when the distal section 2020 is advanced distal to a distal opening 3010 of the catheter 3000, the distal section 2020 can expand in size and/or diameter. For example, the diameter of the distal section can expand by an amount within a range from about 2 mm to about 10 mm Upon or after expanding, the distal section 2020 can be moved in an axial motion, rotated, or a combination of both, either slowly or cycling by hand or using a motor to move as fast as 100 Hz. The delivery catheter can aspirate at the same time while scrubbing with the distal section 2020 or the procedure may involve aspirating mucus before deploying the distal section 2020 or scrubber, then optionally during scrubbing, and then after the distal section 2020 or scrubber has been removed (e.g. retracted proximally) from the catheter 3000. In some cases, elongate element 2010 may be referred to as an elongate member. In some cases, the distal section 2020 can be referred to as an abrasion feature.

In some embodiments, the distal section 2020 includes any of a variety of expandable polymers, metallic meshes of ferrous and non-ferrous metals, and/or composites that may be a combination of metal and polymers to be used as an expandable element. In some cases, the distal section 2020 can be advanced out of the distal opening 3010 of the catheter and allowed to be expanded against the airway wall, and then used to scrub the airway to remove epithelium and goblet cells. Depth of action control can be provided by following a controlled motion pattern and by controlling the abrasive nature of the abrasive material. In some cases, depth control can be achieved or modulated by performing micromotion of a treatment device.

In some cases, the distal section 2020 can include any of a variety of polymers, including any crystalline or amorphous forms of thermoplastic, thermoset, and elastomer materials. Exemplary materials which can be used in the manufacture of the distal section 2020 include, without limitation, low-density polyethylene (LDPE), high-density polyethylene (HDPE), polypropylene (PP), polyvinyl chloride (PVC), polystyrene (PS), nylon, nylon 6, nylon 6,6, Teflon® (polytetrafluoroethylene), thermoplastic polyurethanes (TPU), silicones, vinylpolysiloxane (PVS), or natural polymers, which may be made from proteins and nucleic acid that occur in human body, such as cellulose, natural rubber, silk, and wool, starch, and natural rubber from latex.

In some cases, material of the distal section 2020 can include looped strands or filaments. In some cases, such looped strands or filaments can provide edges which enhance the scraping action of the distal section. In exemplary embodiments, the distal section 2020 includes a material that allows fluid, tissue particles, and/or debris to flow therethrough. In some cases, distal section 2020 may include one or more types of abrasive material.

In some cases, the treatment device 2000 and/or catheter 3000 can be introduced into the patient P using a guidewire or dilator. In some cases, the treatment device 2000 and/or catheter 3000 can be introduced into the patient P without using a guidewire or dilator. Any of the treatment devices disclosed herein can be delivered through a bronchoscope, or only using the lumen of a trachea tube (e.g. such as a trachea tube which is typically used to ventilate a patient, or to gain access within a patient airway past the vocal cords), or only guided over a guidewire, or without guidance by any tube or wire. In some cases, treatment device 2000 can introduced into the patient airway using only the catheter 3000. In some cases, the catheter 3000 can be coupled with, or can be introduced by, a bronchoscope. In some cases, treatment device 2000 can be introduced into the patient airway using only a bronchoscope, without the use of a catheter.

In some cases, the catheter 2000 has an inner lumen diameter with a value within a range from about 6 mm to about 10 mm. Any of the catheter or flexible trunk embodiments disclosed herein may have an inner lumen with similar dimensions.

In some cases, distal section 2020 has a cylindrical shape or profile. In some cases, distal section 202 has a spherical shape or profile. In some case, distal section 2020 has a cone shape or profile. In some cases, distal section has a wider distal diameter or cross-section and a narrower proximal diameter or cross-section.

In some cases, the expansion ratio of the distal section can have a value that is about 10:1 (e.g. uncompressed dimension as depicted in FIG. 28 vs. compressed dimension as depicted in FIG. 27).

In some cases, the elongate element 2010 can be a twisted cable, a braided cable, or any embodiment described herein with reference to FIG. 22. In some cases, the distal section 2020 can be disposed more toward a proximal or central section of the elongate element, for example at or near a connection 624 as depicted in FIG. 22. In some cases, the distal section 2020 can be glued to the elongate element 2010. In some cases, a distal portion of the elongate element 2010 can include a radiopaque material.

In some embodiments, a foam (e.g. expandable foam material of distal section 2020) may be produced with open cell pores having a diameter with a value within a range from about 10 µm to about 5 mm. In some cases, the open cell pores can have one or more dimensions (e.g. width, length, or height) with a value within a range from about 10 µm to about 5 mm in diameter.

In some cases, a densely compressed foam or coarse sponge structure (e.g. FIG. 27) is expandable to a less compressed or uncompressed foam or coarse sponge structure (e.g. FIG. 28). In FIG. 27, it can be seen that the foam or coarse sponge is held in a compressed state because it is confined within the interior of catheter 3000. As shown in FIG. 28, the foam structure of the distal section 2020 can include a connected network of intact expanded loops (or circles) in the central or interior area, and cut strands or edges that project outwardly from the peripheral edges or surfaces of the foam structure. The cut strands can perform as bristles, and can provide add additional scrubbing action, Exposed edges of the loops or circles (e.g. defining the open cell pores) that are disposed on the exterior of the distal section 2020 can also perform a scraping action.

In some cases, the foam element or distal section 2020 may be made from or include strands of ribbon that have been tangled in an organized or non-organized bundle. The ribbon may include or be manufactured from or plated with any of a variety of materials, including without limitation ferrous or non ferrous metal alloys such as stainless steel, aluminum, tantalum, tungsten, silver (or other bacteriostatic or bactericidal materials), gold (or other high radiopacity materials), titanium, Nitinol or other memory shape alloys like this, carbon, polymer, synthetic or natural fibers such as silk or a combination of any of the above. According to some ribbon bundle embodiments, as the bundles are deflected within the elastic range of deformation for any given material (e.g. material used in the manufacture of the ribbon), the bundle can be capable of expanding from a first diameter to a second diameter, after the bundle has been released from a lumen of the catheter 3000. In some cases, the bundle can be capable of expanding from 2 mm diameter inside the guide catheter up to 15 mm diameter or larger, after the bundle has been released from the catheter lumen.

Embodiments of the present invention can take into account the vast tissue damage of advanced COPD sufferers and provides treatment methods and devices designed specifically to treat these patients and the particularly compromised lung tissues that are present in these patients. Such tissue damage has not been identified or acknowledged by previous treatment plans which has led to insufficient treatment and undesired outcomes in many cases. In particular, the present invention includes assessment of the degree of tissue damage and the locations that the damage manifests in a lobe or lobes in the determination of the treatment plan. The extent and distribution of tissue damage is utilized in determining the most optimal locations that the treatment methods should be performed. These same data may also be used to assess the patient over time to determine if more treatments should be performed at the same locations as was targeted in a previous procedure to enhance or restore the improvement brought on in the first procedure or if treatment procedures might be best performed in new locations that were not previously treated in order to restore the benefit brought on by an original treatment.

Overall, the patient typically has a variety of symptomatic improvements, including reduced coughing (e.g. due to trapped air and mucus), increased ability to clear mucus due to passageways opening larger and for longer periods of time, increased mobility (e.g. as measured by currently standard 6-min walk test), reduced inspiratory effort, reduced dysthymia, decreased breathing rate, reduced glottis closure sensitivity (by clearing mucus, inflammation is reduced and coughing is reduced), reduced incidence of respiratory failure and increase time between COPD exacerbation events, to name a few.

Embodiments of the pulmonary treatment device have various features and design elements to achieve the above described treatment effects and clinical goals. In addition, such features and design elements may have varying alternatives, a variety of which will be set forth herein.

Herein various aspects of a pulmonary treatment device are described in more detail. It may be appreciated that although a variety of aspects and features are described, embodiments of the device may include any combination of these aspects and features. Likewise, some embodiments may not include all of the aspects and features described.

In some embodiments, one or more components of a treatment system can be configured to provide controlled delivery of an agent, such as a drug. In some instances, such delivery reduces the rate of wound healing, tissue remodeling, inflammation, generation of granular tissue, and hyperplasia, to name a few.

It may be appreciated that a variety of approaches have been described herein, including treatment devices which are introduced through a lumen in a delivery device (including being pushed or pulled through the lumen by itself, within an introducer or mounted on an additional device such as a catheter or guidewire which is advanceable within the lumen), and treatment devices which are introduced by mounting on an exterior portion of a delivery device, such as the insertion cord tip of a bronchoscope or on a catheter, wherein the treatment device is pushed or pulled from the mounted position by an external or internal sleeve or device.

It may be appreciated that a guidewire is configured to be compatible with advancement within lung tissue, particularly to contact lung tissue with minimal or no incident or injury. In some embodiments, the guidewire is comprised of a wire cable, wire bundles, continuous braid, twisted wire, or twisted wire bundle shaft structure with blunt tip (typically formed by crimping, gluing or welding the tip of the guidewire shaft structure). In some embodiments, the guidewire has a diameter in a range of 0.005 to 0.100 inches, preferably in a range of 0.018 to 0.070 inches. Typically, the guidewire fills the catheter lumen in a way that presents no gaps or very minimal gapping while the guidewire is curved or bent during delivery. In some embodiments, the guidewire is configured so that no portion of the guidewire which contacts tissue creates a gap which opens more than 0.030 inches, preferably in a range of 0 and 0.020 inches during bending around a radius that is 0.5 inches or smaller, to minimize catching tissue in the gaps.

Aspects of these and related guidewire features can be further understood with reference to any one or more of the guidewire embodiments disclosed herein (e.g. FIGS. 6, 7A-7D, 8A-B, 9, 10, 11, and 20-25). In some cases, a guidewire as disclosed herein can include or be manufactured from or plated with any of a variety of materials, including without limitation ferrous or non ferrous metal alloys such as stainless steel, aluminum, tantalum, tungsten, silver (or other bacteriostatic or bactericidal materials), gold (or other high radiopacity materials), titanium, Nitinol or other memory shape alloys like this, carbon, polymer, synthetic or natural fibers such as silk or a combination of any of the above.

Medical imaging techniques may be used to visualize delivery or operation of any of the system or device embodiments disclosed herein. Medical imaging includes the use of all forms of equipment that allows for real time imaging, recording or computer processing that outputs an image of devices, organs or tissue within the human body without needing to expose the devices, organs or tissue to be visualized using a direct line of site by the human eye. These medical imaging techniques may typically benefit by the emission of low to high frequency electro-magnetic energy or sound energy which may include the use of one or more video cameras such as the ones bronchoscopes are equipped with, computed tomography, biplane imaging, fluoroscopy, ultrasound or standard planar x-ray machines. In some embodiments, a pulmonary treatment device is positioned in the lung by a surgical procedure, such as a minimally invasive video assisted portal procedure or an open procedure. Many of the pulmonary treatment devices described herein may be placed in any lung, lobe, mainstem segment, segment, sub-segment or even farther down the airway tree. Likewise, many of the devices may be placed directly through the chest wall into the lung or through the wall of the main bronchi to access pockets of destroyed parenchyma. Many of the devices may be implanted via open chest procedure or with the use of any type of endoscope. The pulmonary function tests listed herein are excellent indicators of positive and adequate response.

All features of the described systems and devices are applicable to the described methods mutatis mutandis, and vice versa. Embodiments of the present invention encompass kits having one or more components of treatment systems as disclosed herein. In some embodiments, the kit includes one or more treatment systems, or one or more components of one or more treatment systems, along with instructions for using the system for example according to any of the methods disclosed herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detaching and removing an amount of mucus from an airway wall of a lung of a patient, comprising:

introducing an elongate member of a treatment device into the lung of the patient, the elongate member having an expandable abrasion feature comprising at least one strand or at least one spring element;

expanding the expandable abrasion feature until it makes contact with the airway wall of the lung, the airway wall comprising a basement membrane, a smooth muscle layer, and a cartilage layer;

detaching the amount of mucus from the airway wall of the lung of the patient with the at least one strand or the at least one spring element of the expandable abrasion feature, without separating the smooth muscle layer of the airway wall from the cartilage layer of the airway wall; and removing the amount of mucus from the airway wall of the lung of the patient while the smooth muscle layer of the airway wall remains supported by the cartilage layer of the airway wall;

wherein the at least one strand comprises a member selected from the group consisting of a metallic wire, a fiber, and a braid, or wherein the at least one spring element comprises a member selected from the group consisting of shape memory material, a ferrous metal, a non-ferrous metal, a polymer, an elastomer, and a ceramic.

2. The method according to claim 1, wherein the expandable abrasion feature comprises an abrasive mesh, an abrasive geometrical feature, or an abrasive media selected from the group consisting of as alumina, carbide, sand, quartz, glass, metal, ceramic, plastic, carbon, diamond, oxide, silicon carbide, polymer, aluminum oxide, co-fused alumina zirconia, garnet, flint, cubic boron nitride, tungsten carbide, cobalt, glass-like polysaccharide, sintered sol-gel, styrene acrylonitrile co-polymer, alumina-zirconia, emery, and chromium (III).

3. The method according to claim 2, wherein the abrasion feature comprises the abrasive media, and wherein the abrasive media has a grit size within a range from about 2 microns in average particle diameter to 3000 microns in average particle diameter.

4. The method according to claim 1, wherein the elongate member comprises an expandable mechanism, and the expandable abrasion feature is disposed on the expandable mechanism, the method further comprising expanding the expandable mechanism.

5. The method according to claim 1, further comprising drawing the amount of mucus into a filter trap using a vacuum source.

6. The method according to claim 1, wherein the expandable abrasion feature is mounted on a guidewire.

7. The method according to claim 6, wherein the guidewire comprises a blunt distal tip.

8. The method according to claim 6, wherein the guidewire is advanced within the patient's airway that is zero generation or higher.

9. The method according to claim 6, wherein the guidewire comprises a wire cable.

10. The method according to claim 6, wherein the guidewire has a diameter within a range of 0.005 inches to 0.100 inches.

11. The method according to claim 1, wherein the elongate member of the treatment device comprises a guidewire.

12. The method according to claim 1, wherein the expandable abrasion feature is delivered through a catheter.

13. The method according to claim 1, wherein the expandable abrasion feature comprises the at least one strand.

14. The method according to claim 13, wherein the at least one strand comprises the metallic wire.

15. The method according to claim 13, wherein the at least one strand comprises a cross-section selected from the group consisting of a round cross-section, a square cross-section, and a rectangular cross-section.

16. The method according to claim 13, wherein the at least one strand comprises a shape selected from the group consisting of a helical shape, a random shape, an egg-beater shape, a sinusoidal shape, and a troposkein shape.

17. The method according to claim 13, wherein the at least one strand comprises multiple strands.

18. The method according to claim 13, wherein the at least one strand comprises nitinol.

19. The method according to claim 13, wherein the at least one strand comprises a shape memory material.

20. The method according to claim 13, wherein the at least one strand has at least one etched surface.

21. The method according to claim 13, wherein the at least one strand comprises the metallic wire, and the metallic wire comprises a member selected from the group consisting of stainless steel, titanium, and a nickel based alloy.

22. The method according to claim 21, wherein the metallic wire comprises the nickel based alloy, and wherein the nickel based alloy comprises nitinol.

23. The method according to claim 13, wherein the at least one strand comprises the fiber, and wherein the fiber is a monofilament fiber or a multifilament fiber.

24. The method according to claim 13, wherein the at least one strand comprises the fiber, and wherein the fiber comprises a member selected from the group consisting of a polymer, a ceramic, and a glass.

25. The method according to claim 13, wherein the at least one strand comprises the fiber, and wherein the fiber comprises a member selected from the group consisting of a plastic, Kevlar®, a carbon fiber, nylon, polyurethane, and polypropylene.

26. The method according to claim 13, wherein the at least one strand is a component of a nitinol wire basket.

27. The method according to claim 13, wherein the at least one strand comprises a member selected from the group consisting of a round-section wire, a square-section wire, and a rectangular-section ribbon.

28. The method according to claim 13, wherein the at least one strand is coupled with and positioned between a connector hub and a distal end.

29. The method according to claim 1, wherein the expandable abrasion feature comprises the at least one spring element.

30. The method according to claim 29, wherein the at least one spring element has an abrasive edge that is provided in the absence of a separate abrasive material.

31. The method according to claim 29, wherein the at least one spring element comprises a round wire.

32. The method according to claim 29, wherein the at least one spring element comprises a flattened shape.

33. The method according to claim 1, wherein the expandable abrasion feature is operable to expand and press against the wall of the lung airway.

34. The method according to claim 1, wherein the expandable abrasion feature is operable to expand and press against the wall of the lung airway, and wherein the airway wall is of an airway having a diameter within a range from about 2 mm to about 25 mm.

35. The method according to claim 1, wherein the expandable abrasion feature is operable to change diameter from a first value to a second value that are within a range from 0.01 mm to 28 mm.

36. The method according to claim 1, wherein the expandable abrasion feature is operable to expand by actuation of a control mechanism.

37. The method according to claim 1, wherein the expandable abrasion feature is operable to expand by actuation of a pull wire of a control mechanism.

38. The method according to claim 1, wherein the patient presents with goblet cell hyperplasia.

39. The method according to claim 1, wherein the patient presents with bronchitis.

40. The method according to claim 1, wherein the patient presents with frequent coughing episodes.

41. The method according to claim 1, wherein the patient presents with a low arterial blood oxygen in the bloodstream.

42. The method according to claim 1, wherein the patient presents with a low walking distance in 6 minutes.

43. The method according to claim 1, wherein the patient presents with a low forced expiratory volume.

44. The method according to claim 1, wherein the patient presents with a high residual volume.

45. The method according to claim 1, wherein the patient presents with a high trapped lung gas volume during or after expiration.

46. The method according to claim 1, wherein the elongate member is received in a working channel exit port of a bronchoscope, and wherein the bronchoscope is steerable.

47. The method according to claim 46, wherein the bronchoscope has a working channel having a diameter that is 3.2 mm or smaller.

48. The method according to claim 46, wherein the bronchoscope is steerable by an electrical driver.

49. The method according to claim 1, wherein the expandable abrasion feature is operable to expand by actuation of a handle of a control mechanism.

50. The method according to claim 1, wherein the expandable abrasion feature is operable to expand by actuation of a motorized driver of a control mechanism.

51. The method according to claim 1, wherein the expandable abrasion feature is operable to expand via robot operation of a control mechanism.

52. The method according to claim 1, wherein the expandable abrasion feature is operable to move along or within the airway wall via robot operation of a control mechanism.

53. The method according to claim 1, wherein the expandable abrasion feature is operable to expand or move along or within the airway wall via robot motor or magnetic actuator operation of a control mechanism.

54. The method according to claim 1, wherein the expandable abrasion feature is operable to expand by actuation of a control mechanism having an electrically actuated driver.

55. The method according to claim 1, wherein the expandable abrasion feature is operable to expand driven by stored strain energy.

56. A method for detaching and enabling removal of an amount of mucus from an airway wall of a lung of a patient, comprising:

introducing an elongate member of a treatment device into the lung of the patient, the elongate member having an expandable abrasion feature comprising at least one strand or at least one spring element;

expanding the expandable abrasion feature until it makes contact with the airway wall of the lung, the airway wall comprising a basement membrane, a smooth muscle layer, and a cartilage layer; and detaching the amount of mucus from the airway wall of the lung of the patient with the at least one strand of the expandable abrasion feature or the at least one spring element of the expandable abrasion feature, without separating the smooth muscle layer of the airway wall from the cartilage layer of the airway wall, so as to enable removal of the amount of mucus from the airway wall of the lung of the patient while the smooth muscle layer of the airway wall remains supported by the cartilage layer of the airway wall;

wherein the at least one strand comprises a member selected from the group consisting of a metallic wire, a fiber, and a braid, or wherein the at least one spring element comprises a member selected from the group consisting of shape memory material, a ferrous metal, a non-ferrous metal, a polymer, an elastomer, and a ceramic.

57. A method for treating an airway wall of a lung of a patient to increase time between chronic obstructive pulmonary disease (COPD) exacerbation events, comprising:

introducing an elongate member of a treatment device into the lung of the patient, the elongate member having an expandable abrasion feature comprising at least one strand or at least one spring element;

expanding the expandable abrasion feature until it makes contact with the airway wall of the lung, the airway wall comprising a basement membrane, a smooth muscle layer, and a cartilage layer; and detaching an amount of mucus from the airway wall of the lung of the patient with the at least one strand of the expandable abrasion feature or the at least one spring element of the expandable abrasion feature, without separating the smooth muscle layer of the airway wall from the cartilage layer of the airway wall, so as to enable removal of the amount of mucus from the airway wall of the lung of the patient while the smooth muscle layer of the airway wall remains supported by the cartilage layer of the airway wall;

wherein the at least one strand comprises a member selected from the group consisting of a metallic wire, a fiber, and a braid, or wherein the at least one spring element comprises a member selected from the group consisting of shape memory material, a ferrous metal, a non-ferrous metal, a polymer, an elastomer, and a ceramic.

* * * * *